(12) United States Patent
Chen et al.

(10) Patent No.: US 10,239,872 B2
(45) Date of Patent: Mar. 26, 2019

(54) THERAPEUTIC AGENTS FOR THE TREATMENT OF HBV INFECTION

(71) Applicant: Newave Pharmaceutical Inc., Pleasanton, CA (US)

(72) Inventors: Yi Chen, Pleasanton, CA (US); Yan Lou, Pleasanton, CA (US)

(73) Assignee: Newave Pharmaceutical Inc., Pleasanton, CA (US)

( * ) Notice: Subject to any disclaimer, the term of this patent is extended or adjusted under 35 U.S.C. 154(b) by 0 days.

(21) Appl. No.: 15/896,285

(22) Filed: Feb. 14, 2018

(65) Prior Publication Data

US 2018/0170925 A1 Jun. 21, 2018

Related U.S. Application Data

(63) Continuation of application No. PCT/US2017/041350, filed on Jul. 10, 2017.

(60) Provisional application No. 62/516,569, filed on Jun. 7, 2017, provisional application No. 62/486,946, filed on Apr. 18, 2017, provisional application No. 62/418,684, filed on Nov. 7, 2016, provisional application No. 62/368,165, filed on Jul. 29, 2016.

(51) Int. Cl.
*C07D 455/06* (2006.01)
*C07D 471/04* (2006.01)
*A61P 31/20* (2006.01)
*C07D 498/04* (2006.01)

(52) U.S. Cl.
CPC .......... *C07D 455/06* (2013.01); *A61P 31/20* (2018.01); *C07D 471/04* (2013.01); *C07D 498/04* (2013.01)

(58) Field of Classification Search
CPC .................................................. C07D 455/06
USPC .......................................... 546/95; 514/294
See application file for complete search history.

(56) References Cited

U.S. PATENT DOCUMENTS

| 6,334,997 | B1 * | 1/2002 | Foster ............... | C07B 59/002 424/1.81 |
|---|---|---|---|---|
| 2004/0029879 | A1 | 2/2004 | Anderson et al. | |
| 2004/0253180 | A1 * | 12/2004 | Foster ............... | C07B 59/002 424/9.2 |
| 2011/0065687 | A1 | 3/2011 | Schwaebe et al. | |
| 2016/0122344 | A1 | 5/2016 | Han et al. | |

FOREIGN PATENT DOCUMENTS

| CN | 201610626628.1 | 2/2018 |
|---|---|---|
| CN | 201610671491.1 | 2/2018 |
| WO | 2015/113990 A1 | 8/2015 |
| WO | 2015/173164 A1 | 11/2015 |
| WO | 2016/071215 A1 | 5/2016 |
| WO | 2016/107832 A1 | 7/2016 |
| WO | 2016/128335 A1 | 8/2016 |
| WO | 2017/013046 A1 | 1/2017 |
| WO | 2017/016921 A1 | 2/2017 |
| WO | 2017/016960 A1 | 2/2017 |
| WO | 2017/017042 A1 | 2/2017 |
| WO | 2017/017043 A1 | 2/2017 |
| WO | 2017/108630 A1 | 6/2017 |
| WO | 2017/140821 A1 | 8/2017 |
| WO | 2017/216685 A1 | 12/2017 |
| WO | 2017/216686 A1 | 12/2017 |
| WO | 2018/019297 A1 | 2/2018 |

OTHER PUBLICATIONS

Yu et al., "Physical characterization of, etc.," PSTT, vl. 1(3), 118-127). (Year: 1998).*
Braga et al., "Making crystals from . . . . " J. Royal Soc. Chem. Commun. p. 3635-3645. (Year: 2005).*
Bernstein, "Polymorphism in . . . . " p. 115-118, 272. (Year: 2002).*
Davidovich et al., "Detection of polymorphism . . . . " Am. Pharm. Rev. v.&(1) p. 10, 12, 14, 16, 100). (Year: 2004).*
Dean "Analytical Chem . . . . " p. 10.24-10.26. (Year: 1995).*
Ivanisevic et al. "Use of X-ray . . . . " Pharm. Sci. Encycl. p. 1-42. (Year: 2010).*
Seddon "Pseudopolymorph . . . . " Crystal Growth & design v.4(6) p. 108 (2 pp. from internet) (Year: 2004).*
Jain et al., "Polymorphism in Pharmacy", Indian Drugs 23(6) 315-329. (Year: 1986).*
Jordan "Tamoxifen . . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*
Guillory (in Brittain ed.), "Polymorphism in Pharmaceutical Solids.," NY: Marcel Dekker, Inc., 1-2, 125-181, 183-226. (Year: 1999).*

(Continued)

*Primary Examiner* — Patricia L Morris
(74) *Attorney, Agent, or Firm* — McCarter & English, LLP; Yu Lu; Wei Song

(57) ABSTRACT

The disclosure includes compounds of Formula (I)

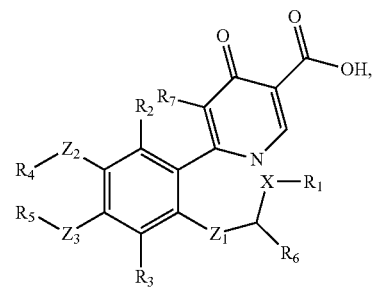

wherein $Z_1$, $Z_2$, $Z_3$, X, $R_1$, $R_2$, $R_3$, $R_4$, $R_5$, $R_6$, and $R_7$ are defined herein. Also disclosed is a method for treating HBV infection.

3 Claims, No Drawings

(56) References Cited

OTHER PUBLICATIONS

Fisher et al., "The complexities, etc.," Current Opininon in Drug Discovery & Development 2006, 9(1), 101-109.*
Wade, "Deuterium isotope, etc.," Chemico-Biological Interactions 117 (1999) 191-217.*
Foster, Deuterium isotope, etc., TIPS, Dec. 1984, 524-527.*
Blake, "Studies with, etc.," J of Pharmaceutical Sciences, 64(3), 1975, 367-391.*
PubChem CID: 101154546, 1-Fluoro-9,10-dimethoxy-6,7-dihydro-2H-benzo[a]quinolizine-2-one. Retrieved online at: https://pubchem.ncbi.nlm.nih.gov/compound/101154546. 8 pages, Aug. 26, 2017.
International Search Report and Written Opinion for Application No. PCT/US2017/041350, dated Sep. 26, 2017. 7 pages.

* cited by examiner

THERAPEUTIC AGENTS FOR THE TREATMENT OF HBV INFECTION

REFERENCE TO RELATED APPLICATIONS

This application is a continuation application of International Application No. PCT/US2017/041350, filed on Jul. 10, 2017, which claims the benefit of the filing date of U.S. Provisional Application No. 62/368,165, filed on Jul. 29, 2016; U.S. Provisional Application No. 62/418,684, filed on Nov. 7, 2016; U.S. Provisional Application No. 62/486,946, filed on Apr. 18, 2017; and U.S. Provisional Application No. 62/516,569, filed on Jun. 7, 2017. The entire contents of each of the aforementioned applications are incorporated herein by reference.

BACKGROUND OF THE INVENTION

Despite the availability of effective vaccines and antiviral therapies, hepatitis B is still a major global health problem, with one-third of all people on the planet having been at some time infected with the hepatitis B virus (HBV). In 2016, there are currently more than 240 million people with chronic hepatitis B, which leads to more than 780,000 deaths per year following development of liver disease, such as cirrhosis, liver cancer, or other complications. The therapeutic options for the patients with chronic hepatitis B include two forms of interferon-α (IFN-α) as immune system modulators and nucleos(t)ide analogues. IFN-α therapy is effective for up to 60% of patients but results in complete cures in only 7% and also is associated with a high rate of adverse side effects.

The hepatitis B virus (HBV) is an enveloped, partially double-stranded DNA virus. The virus particle is composed of a lipid enveloped studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core.

One of the classic hallmarks of chronic hepatitis B is the high levels of hepatitis B virus surface antigen (HBsAg) in the serum of patients, which may reach 400 μg/mL (0.4% of total serum protein). The antigenemia resulting from production of subviral particles is thought to play an important role in suppressing the HBV-specific immune response. In addition, recent reports have suggested that HBsAg acts directly on dendritic cells to limit cytokine production and adaptive immunity. Reduction of antigenemia with the experimental antiviral clevudine resulted in a partial restoration of virus-specific immune response. Thus, inhibitors of HBsAg secretion could potentially enable the therapeutic use of the HBV vaccine or be used as combination therapy with nucleos(t)ide drugs for the treatment of HBV infection.

WO/2015/113990 and WO/2016/107832 reported a class of HBsAg inhibitors for the treatment and prophylaxis of hepatitis b virus infection. The paper in J Med Chem. 2011, 54(16): 5660-5670 reported novel agents triazolo-pyrimidine derivatives as novel inhibitors of HBsAg secretion.

Although those agents have made a significant contribution to the art, there is a continuing search in this field of art for improved pharmaceuticals.

SUMMARY OF THE INVENTION

This invention provides compounds of the Formula (I) or an N-oxide thereof, or a pharmaceutically acceptable salt, solvate, polymorph or tautomer of said compound of formula (I) or N-oxide thereof:

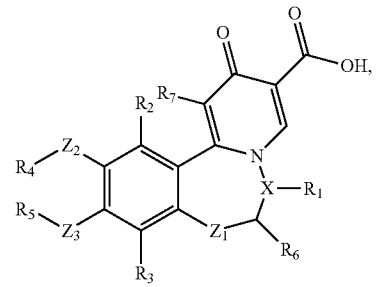

wherein $R_7$ is halo, low alkyl, $CF_3$, CN, nitro, OH, $OR_a$, or $NH_2$;

$Z_1$ is absent, O, $N(R_a)$, or $C(R_bR_c)$;

X is $C(R_0)$ or N, in which $R_0$ is H, D, or $CF_3$;

each of $Z_2$, and $Z_3$, independently, is absent, O, $(CH_2)_pO$, $O(CH_2)_pO$, $N(H)$, $(CH_2)_p$, S, C(O), $SO_2$, OC(O), C(O)O, $OSO_2$, $S(O)_2O$, C(O)S, SC(O), C(O)C(O), C(O)N(H), N(H)C(O), $S(O)_2N(H)$, $N(H)S(O)_2$, OC(O)O, OC(O)S, OC(O)N(H), N(H)C(O)O, N(H)C(O)S, N(H)C(O)N(H), $(CH_2)_pN(H)(CH_2)_q$, $(CH_2)_pO(CH_2)_q$, $(CH_2)_pN(H)C(O)(CH_2)_q$, $(CH_2)_pC(O)N(H)(CH_2)_q$, $OC(O)N(H)(CH_2)_{p+1}N(H)(CH_2)_q$, a bivalent alkenyl group, or a bivalent alkynyl group;

each of $R_1$, $R_2$, $R_3$, $R_4$, $R_5$, and $R_6$, independently, is H, alkyl, alkenyl, alkynyl, cycloalkyl, cycloalkenyl, heterocycloalkyl, heterocycloalkenyl, aryl, heteroaryl, halo, nitro, oxo, cyano, $—(CH_2)_pR_a$, $—OR_a$, $—SR_a$, $—NH(CH_2)_pR_a$, $—C(O)R_a$, $—S(O)R_a$, $—SO_2R_a$, $—C(O)OR_a$, $—OC(O)R_a$, $—NR_bR_c$, $—P(O)R_bR_c$, $—C(O)N(R_b)R_c$, $—N(R_b)C(O)R_c$, $—SO_2N(R_b)R_c$, or $—N(R_b)SO_2R_c$, in which said alkyl, cycloalkyl, cycloalkenyl, heterocycloalkyl, heterocycloalkenyl, aryl, heteroaryl is optionally substituted with one or more $R_d$;

each of p, and q, independently, is 0, 1, 2, 3, 4, 5, 6, 7, or 8;

$R_a$, $R_b$, $R_c$ and $R_d$, independently, is H, D, $CD_3$, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

$R_4$ and $R_5$, together with the atoms to which they are attached form an optionally substituted cycloalkyl or heterocycloalkyl; and $R_1$ and $R_6$, together with the atoms to which they are attached form an optionally substituted cycloalkyl or heterocycloalkyl.

In certain embodiments, the compound is represented by Formula (II):

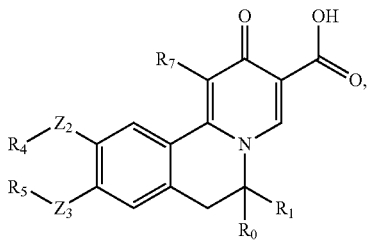

wherein R₁ is H, alkyl, alkenyl, alkynyl, cycloalkyl, cycloalkenyl, heterocycloalkyl, heterocycloalkenyl, aryl, or heteroaryl, in which said alkyl, alkenyl, alkynyl, cycloalkyl, cycloalkenyl, heterocycloalkyl, heterocycloalkenyl, aryl, heteroaryl is optionally substituted with one or more $R_d$.

In a more preferred embodiment, $R_0$ is H, or D; $R_1$ is alkyl, cycloalkyl, aryl, or heteroaryl, in which said alkyl, cycloalkyl, aryl, or heteroaryl is optionally substituted with one or more $R_d$; $Z_2$ is absent, or O; $R_4$ is H, halo, alkyl optionally substituted with one or more $R_d$; $Z_3$ is absent, O, or O(CH₂)$_p$O; $R_5$ is H, alkyl optionally substituted with one or more $R_d$; and $R_7$ is halo.

In a more preferred embodiment, $R_1$ is alkyl, or cycloalkyl, in which said alkyl, or cycloalkyl is optionally substituted with one or more $R_d$; $R_4$ is H, halo, alkyl optionally substituted with one or more D; $R_5$ is H, alkyl optionally substituted with one or more D; and $R_7$ is F.

In other certain embodiments, the compound is represented by Formula (III):

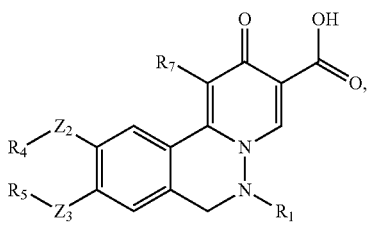

wherein R₁ is H, alkyl, alkenyl, alkynyl, cycloalkyl, cycloalkenyl, heterocycloalkyl, heterocycloalkenyl, aryl, or heteroaryl, in which said alkyl, alkenyl, alkynyl, cycloalkyl, cycloalkenyl, heterocycloalkyl, heterocycloalkenyl, aryl, heteroaryl is optionally substituted with one or more $R_d$.

In a more preferred embodiment, $R_1$ is alkyl, cycloalkyl, aryl, or heteroaryl, in which said alkyl, cycloalkyl, aryl, or heteroaryl is optionally substituted with one or more $R_d$; $Z_2$ is absent, or O; $R_4$ is H, halo, alkyl optionally substituted with one or more $R_d$; $Z_3$ is absent, O, or O(CH₂)$_p$O; $R_5$ is H, alkyl optionally substituted with one or more $R_d$; and $R_7$ is halo.

In a more preferred embodiment, $R_1$ is alkyl, or cycloalkyl, in which said alkyl, or cycloalkyl is optionally substituted with one or more $R_d$; $R_4$ is H, halo, alkyl optionally substituted with one or more D; $R_5$ is H, alkyl optionally substituted with one or more D; and $R_7$ is F.

In certain embodiments, the compound is represented by Formula (A):

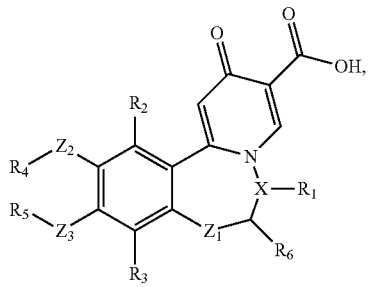

wherein

X is C($R_0$) or N, in which $R_0$ is H, D, or CF₃;

$Z_1$ is O, N($R_a$), or C($R_b R_c$), provided that if $Z_1$ is C($R_b R_c$) then X is N;

each of $Z_2$, and $Z_3$, independently, is absent, O, (CH₂)$_p$O, O(CH₂)$_p$O, N(H), (CH₂)$_p$, S, C(O), SO₂, OC(O), C(O)O, OSO₂, S(O)₂O, C(O)S, SC(O), C(O)C(O), C(O)N(H), N(H)C(O), S(O)₂N(H), N(H)S(O)₂, OC(O)O, OC(O)S, OC(O)N(H), N(H)C(O)O, N(H)C(O)S, N(H)C(O)N(H), (CH₂)$_p$N(H)(CH₂)$_q$, (CH₂)$_p$O(CH₂)$_q$, (CH₂)$_p$N(H)C(O)(CH₂)$_q$, (CH₂)$_p$C(O)N(H)(CH₂)$_q$, OC(O)N(H)(CH₂)$_{p+1}$N(H)(CH₂)$_q$, a bivalent alkenyl group, or a bivalent alkynyl group;

each of $R_1$, $R_2$, $R_3$, $R_4$, $R_5$, and $R_6$, independently, is H, alkyl, alkenyl, alkynyl, cycloalkyl, cycloalkenyl, heterocycloalkyl, heterocycloalkenyl, aryl, heteroaryl, halo, nitro, oxo, cyano, —(CH₂)$_p R_a$, —O$R_a$, —S$R_a$, —NH(CH₂)$_p R_a$, —C(O)$R_a$, —S(O)$R_a$, —SO₂$R_a$, —C(O)O$R_a$, —OC(O)$R_a$, —N$R_b R_c$, —P(O)$R_b R_c$, —C(O)N($R_b$)$R_c$, —N($R_b$)C(O)$R_c$, —SO₂N($R_b$)$R_c$, or —N($R_b$)SO₂$R_c$, in which said alkyl, cycloalkyl, cycloalkenyl, heterocycloalkyl, heterocycloalkenyl, aryl, heteroaryl is optionally substituted with one or more $R_d$;

each of p, and q, independently, is 0, 1, 2, 3, 4, 5, 6, 7, or 8;

$R_a$, $R_b$, $R_c$ and $R_d$, independently, is H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl;

$R_4$ and $R_5$, together with the atoms to which they are attached form an optionally substituted cycloalkyl or heterocycloalkyl; and $R_1$ and $R_6$, together with the atoms to which they are attached form an optionally substituted cycloalkyl or heterocycloalkyl.

In certain embodiments, the compound is represented by Formula (B):

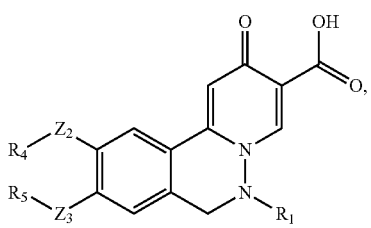

wherein

R$_1$ is fluoroalkyl, fluorocycloalkyl, aryl, or heteroaryl, in which said fluoroalkyl, fluorocycloalkyl, aryl, or heteroaryl is optionally substituted with one or more R$_d$;

each of Z$_2$, and Z$_3$, independently, is absent, O, (CH$_2$)$_p$O, O(CH$_2$)$_p$O, N(H), (CH$_2$)$_p$, S, C(O), SO$_2$, OC(O), C(O)O, OSO$_2$, S(O)$_2$O, C(O)S, SC(O), C(O)C(O), C(O)N(H), N(H)C(O), S(O)$_2$N(H), N(H)S(O)$_2$, OC(O)O, OC(O)S, OC(O)N(H), N(H)C(O)O, N(H)C(O)S, N(H)C(O)N(H), (CH$_2$)$_p$N(H)(CH$_2$)$_q$, (CH$_2$)$_p$O(CH$_2$)$_q$, (CH$_2$)$_p$N(H)C(O)(CH$_2$)$_q$, (CH$_2$)$_p$C(O)N(H)(CH$_2$)$_q$, OC(O)N(H)(CH$_2$)$_{p+1}$N(H)(CH$_2$)$_q$, a bivalent alkenyl group, or a bivalent alkynyl group;

each of R$_1$, R$_2$, R$_3$, R$_4$, and R$_5$, independently, is H, alkyl, alkenyl, alkynyl, cycloalkyl, cycloalkenyl, heterocycloalkyl, heterocycloalkenyl, aryl, heteroaryl, halo, nitro, oxo, cyano, —(CH$_2$)$_p$R$_a$, —OR$_a$, —SR$_a$, —NH(CH$_2$)$_p$R$_a$, —C(O)R$_a$, —S(O)R$_a$, —SO$_2$R$_a$, —C(O)OR$_a$, —OC(O)R$_a$, —NR$_b$R$_c$, —P(O)R$_b$R$_c$, —C(O)N(R$_b$)R$_c$, —N(R$_b$)C(O)R$_c$, —SO$_2$N(R$_b$)R$_c$, or —N(R$_b$)SO$_2$R$_c$, in which said alkyl, cycloalkyl, cycloalkenyl, heterocycloalkyl, heterocycloalkenyl, aryl, heteroaryl is optionally substituted with one or more R$_d$;

each of p and q, independently, is 0, 1, 2, 3, 4, 5, 6, 7, or 8;

R$_a$, R$_b$, R$_c$ and R$_d$, independently, is H, D, alkyl, alkenyl, alkynyl, halo, cyano, amine, nitro, hydroxy, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, heterocycloalkenyl, aryl, or heteroaryl; and R$_4$ and R$_5$, together with the atoms to which they are attached form an optionally substituted cycloalkyl or heterocycloalkyl.

In a more preferred embodiment, R$_1$ is

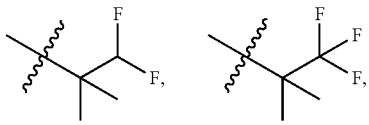

aryl, or heteroaryl.

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a disease, therapeutic uses thereof, and use of the compounds for the manufacture of a medicament for treating the disease/disorder.

The compounds of the invention can inhibit HBsAg or secretion and inhibit HBV gene expression. Accordingly, the compounds of the invention are useful for the treatment or prophylaxis of HBV infection.

The invention relates to the use of a compound of Formula (I) for the inhibition of HBsAg production or secretion.

The invention relates to the use of a compound of Formula (I) for the inhibition of HBV DNA production.

The invention relates to the use of a compound of Formula (I) for the inhibition of HBV gene expression.

The invention relates to the use of a compound of Formula (I) for the treatment or prophylaxis of HBV infection.

The use of a compound of Formula (I) for the preparation of medicaments useful in the treatment or prophylaxis diseases that are related to HBV infection is an object of the invention.

The invention relates in particular to the use of a compound of Formula (I) for the preparation of a medicament for the treatment or prophylaxis of HBV infection.

This invention also relates to a method of treatment or prophylaxis of HBV infection, by administering to a subject in need thereof an effective amount of one or more of the compounds, modifications, and/or salts, and compositions thereof described above.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc.) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

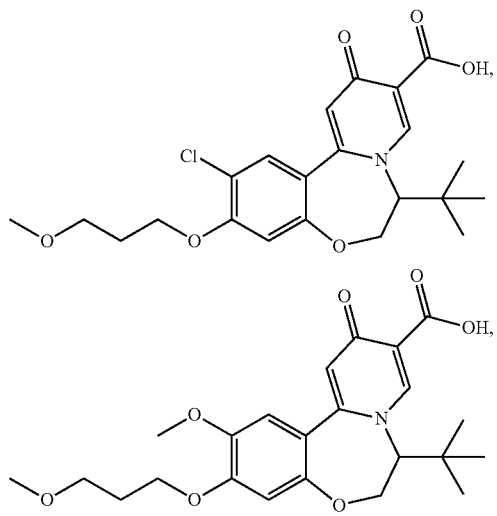

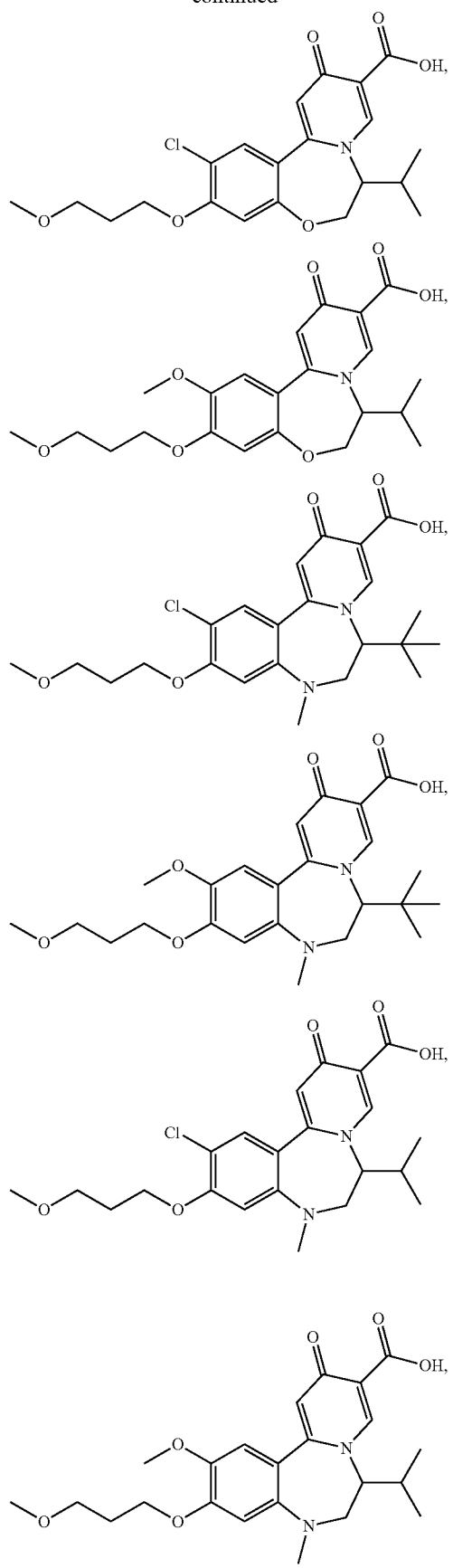
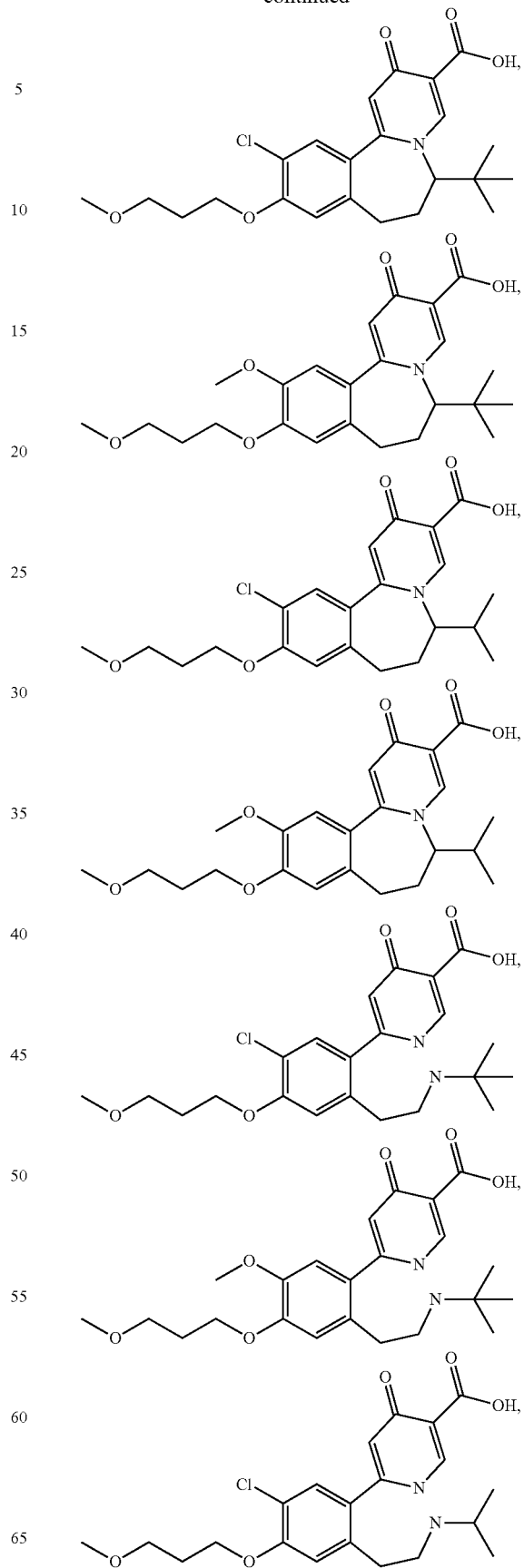

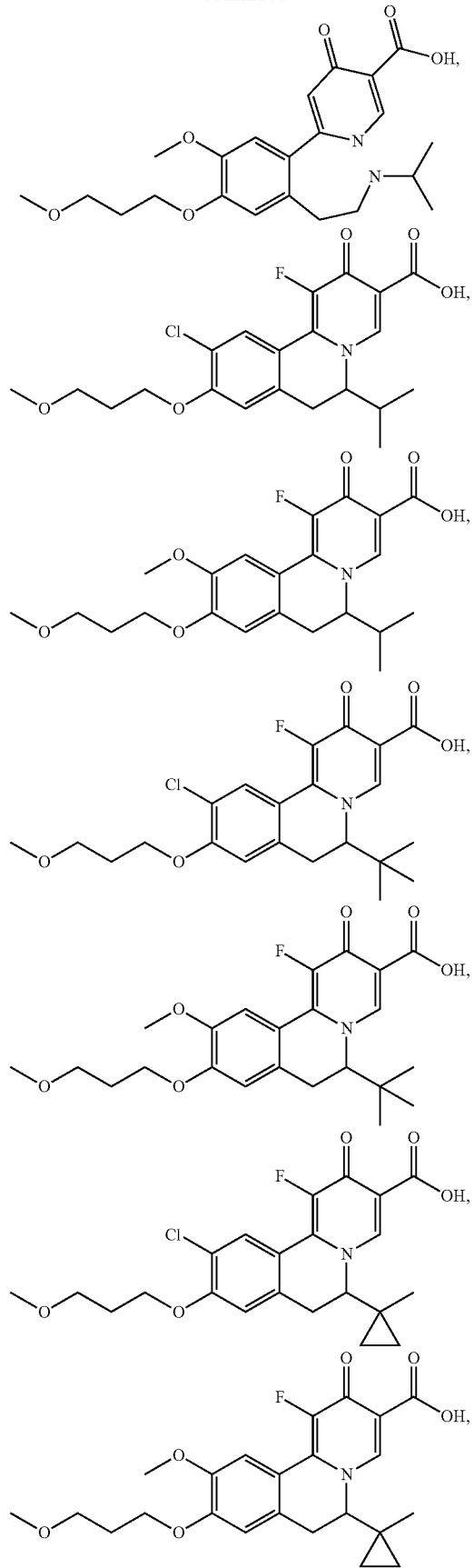
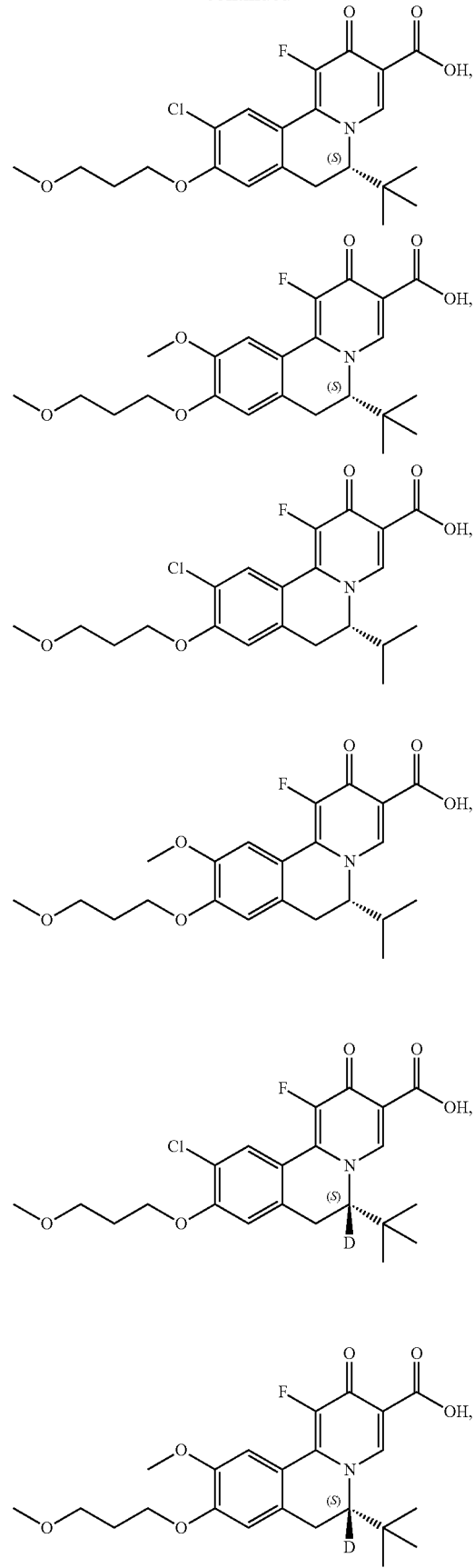

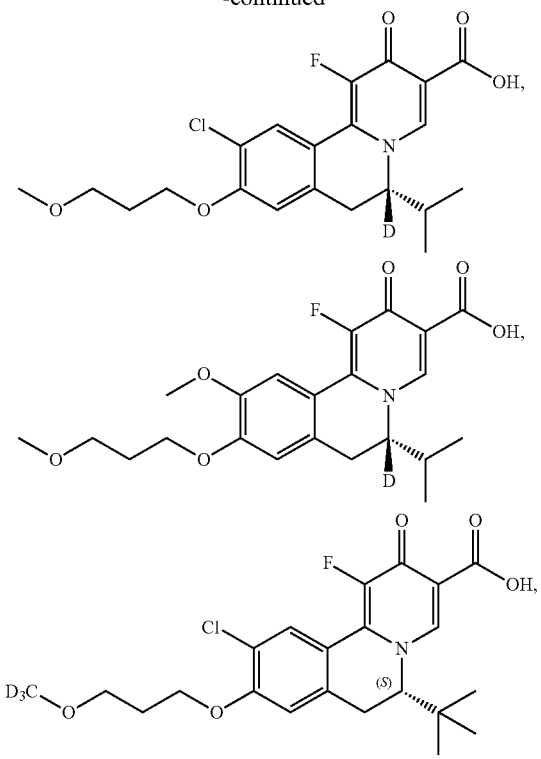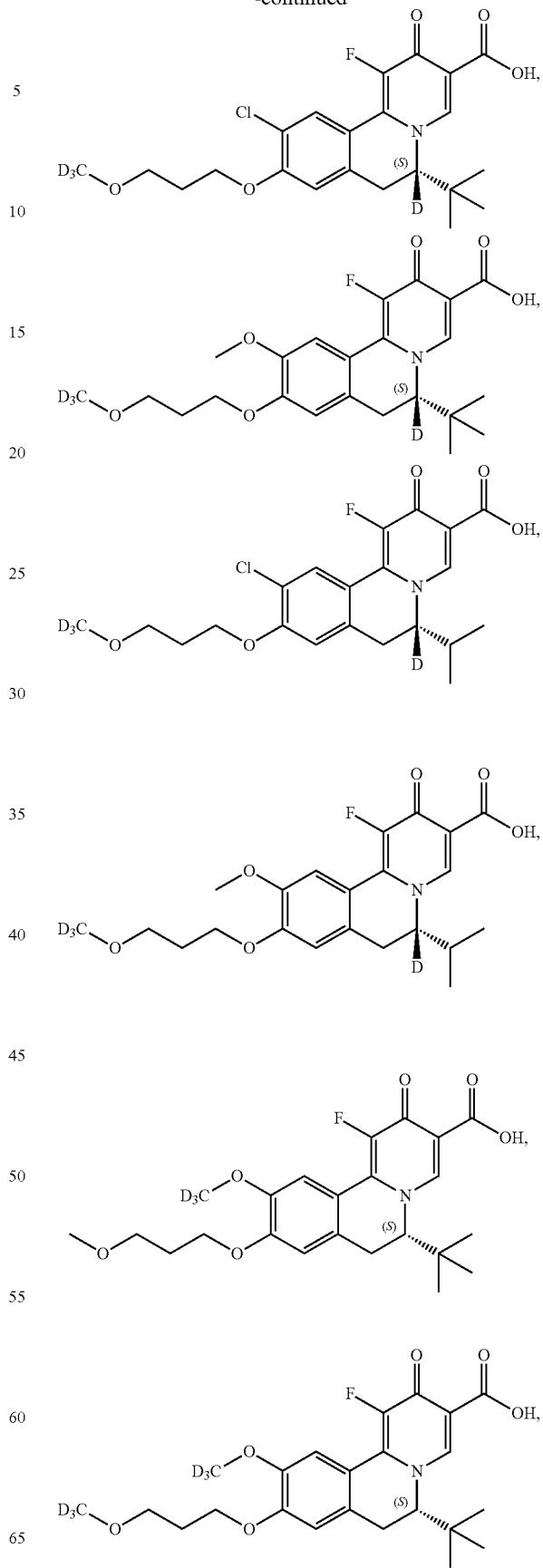

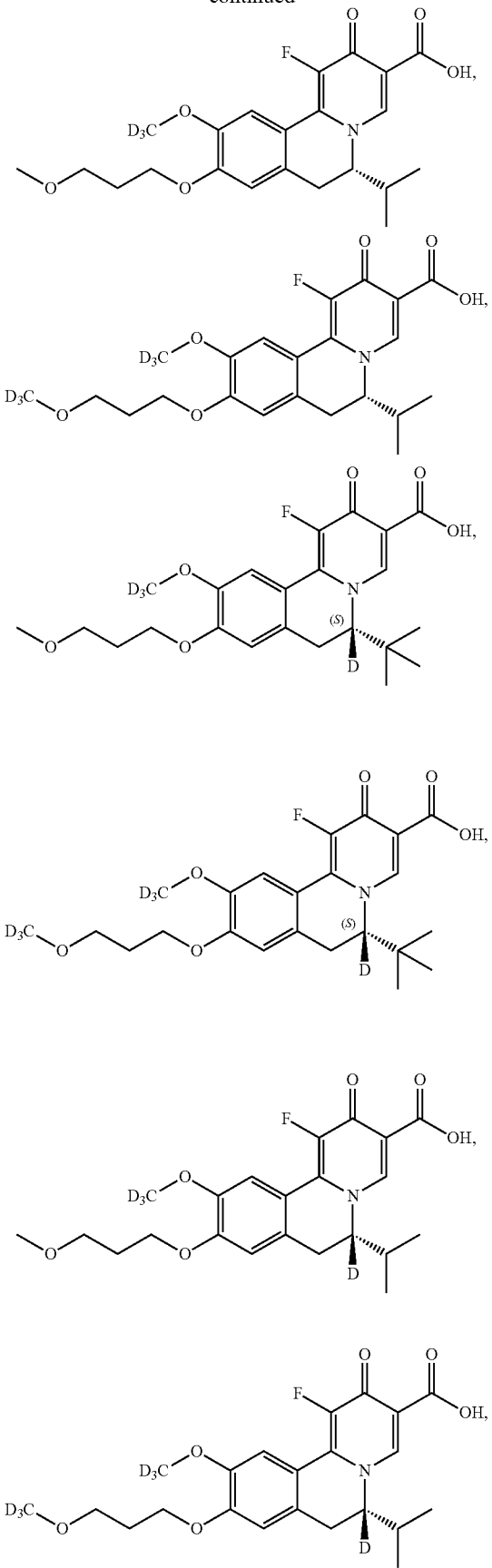
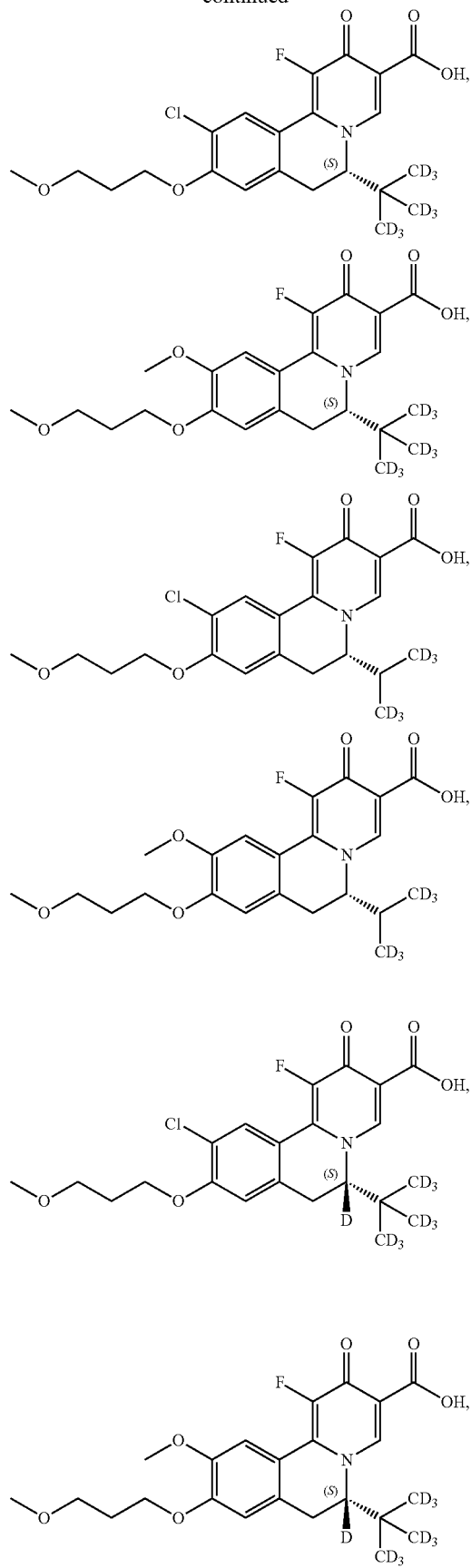

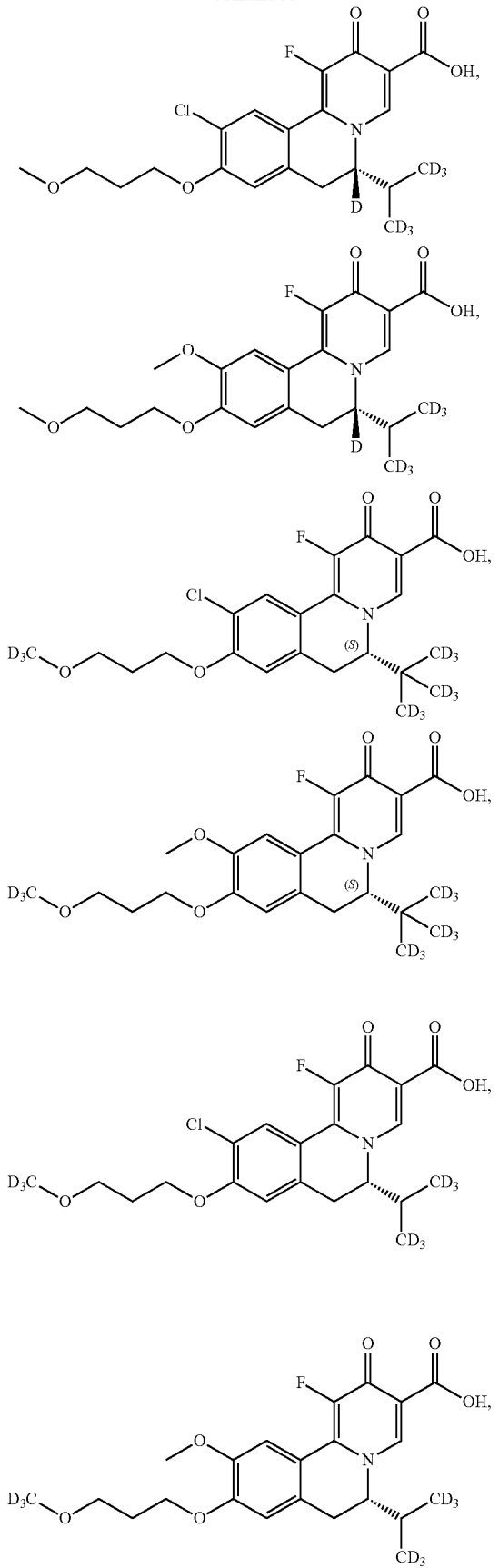
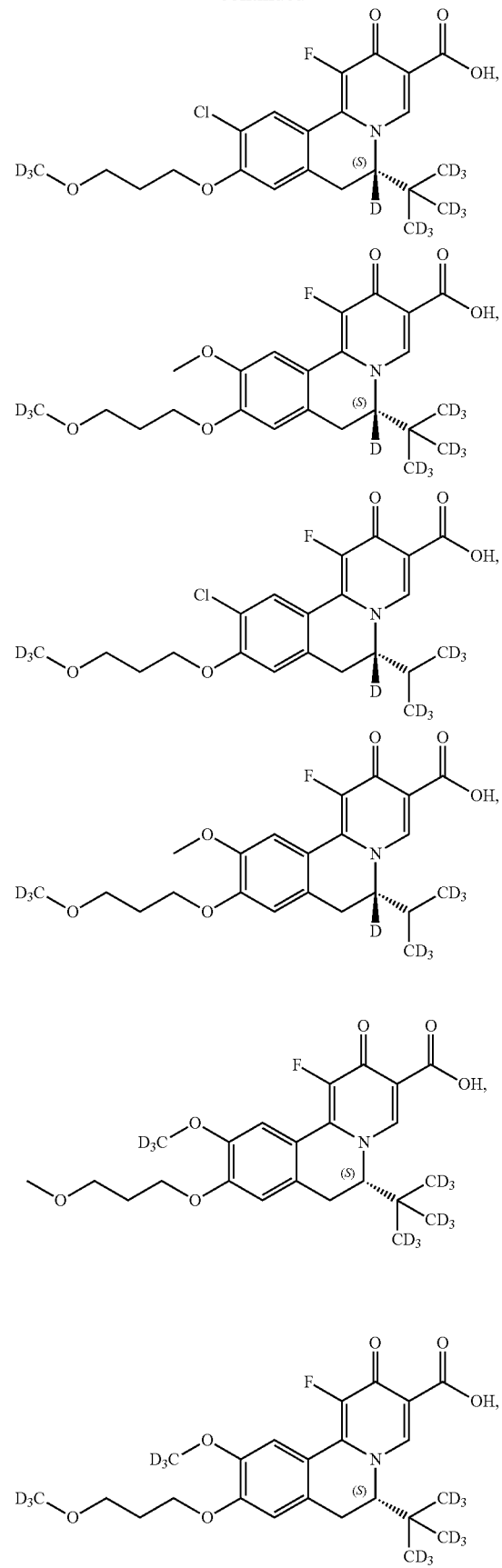

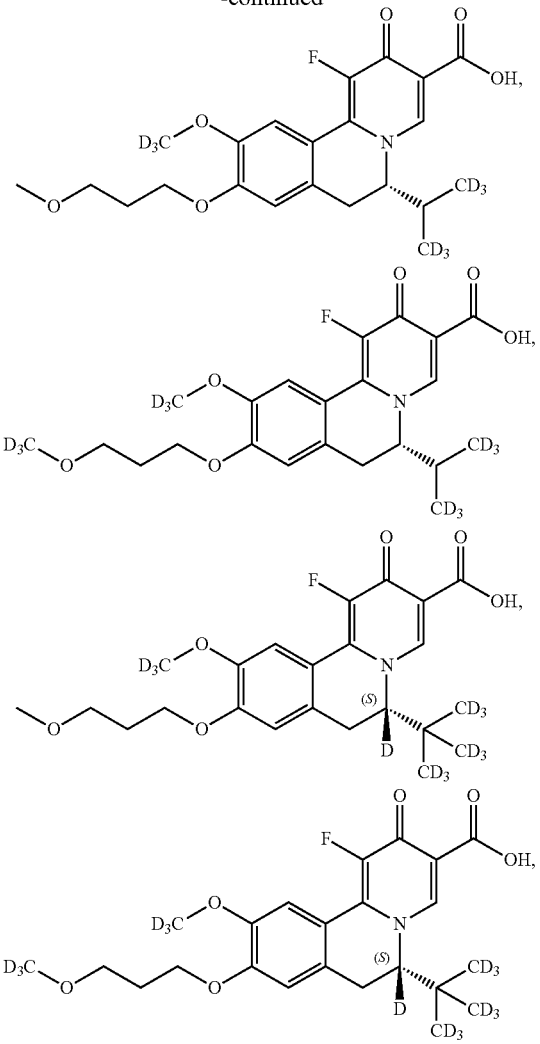
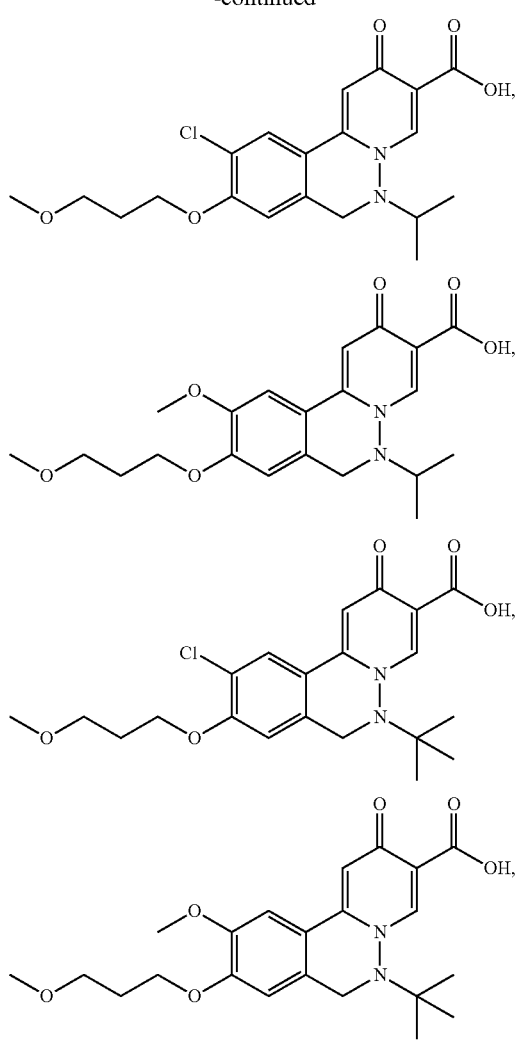
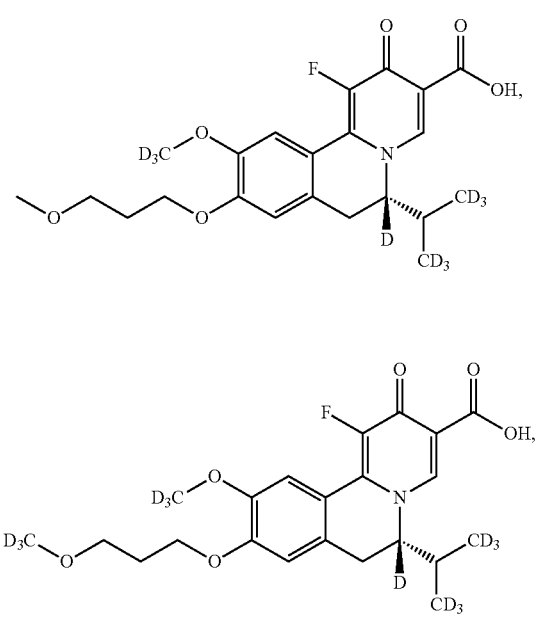

-continued

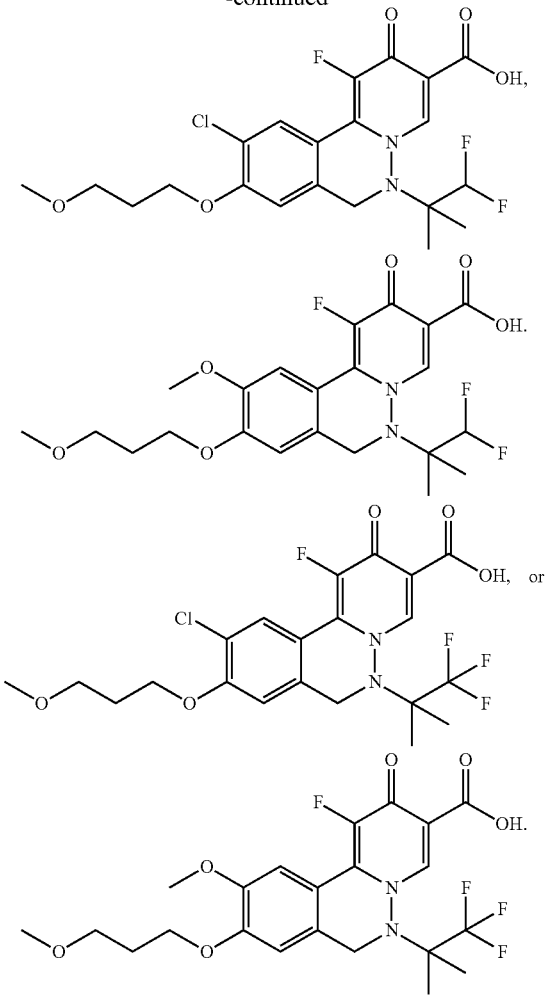

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art.

Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters*, 1994, Vol. 4, p. 1985.

Deuterium-enriched compounds: deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as ($C_{1-4}$) alkyl halides, e.g., methyl, ethyl, iso-propyl and tert-butyl chlorides, bromides and iodides; di-($C_{1-4}$) alkyl sulfates, e.g., dimethyl, diethyl and diamyl sulfates; alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3 (3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a HBV infection, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antin-HBV infection agent). For instance, The compounds of the invention can be combined with other anti HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti HBV agents such as HBV RNA replication inhibitor, HBsAg secretion inhibitors, HBV core protein allosteric modifiers, HBV capsid inhibitors, antisense oligomer, siRNA, HBV therapeutic vaccine, HBV prophylactic vaccine, HBV antibody therapy (monoclonal or polyclonal) and TLR 2, 3, 7, 8 and 9 agonists for the treatment or prophylaxis of HBV. The compounds of the invention can be administered simultaneously (as a single preparation or separate preparation) or sequentially to the other therapies. In general, a combination therapy envisions administration of two or more drugs/treatments during a single cycle or course of therapy.

The invention further provides methods for the prevention or treatment of a HBV infection disease. In one embodiment, the invention relates to a method of treating a HBV infection, in a subject in need of treatment comprising administering to said subject a therapeutically effective amount of a compound of the invention. In one embodiment, the invention further provides for the use of a compound of the invention in the manufacture of a medicament for halting or decreasing the HBV infection.

It should be understood that the invention is not limited to the particular embodiments shown and described herein, but that various changes and modifications may be made without departing from the spirit and scope of the invention as defined by the claims.

The compounds according to the present invention may be synthesized according to a variety of schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of the intermediate

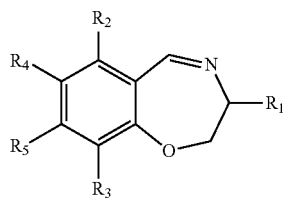

is described in Scheme 1. $R_1$, $R_2$, $R_3$, $R_4$, and $R_5$ in Scheme 1 are the same as those described in the Summary section above.

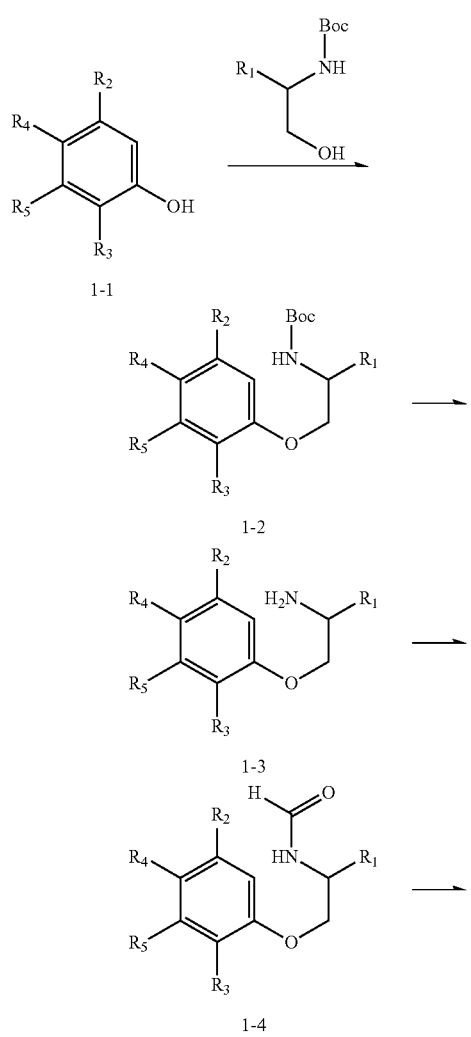

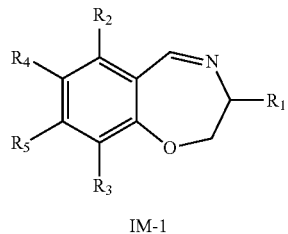

In Scheme 1, the appropriate starting material 1-1 can react with appropriate alcohol to to give intermediate 1-2, which can undergo a de-Boc process to yield the amine intermediate 1-3. After that, 1-3 is heated with ethyl formate or formic acid in a solvent such as ethanol or dioxane affords intermediate 1-4, which can undergo a cyclization reaction to form the imine intermediate IM-1.

A typical approach to synthesize of the intermediate

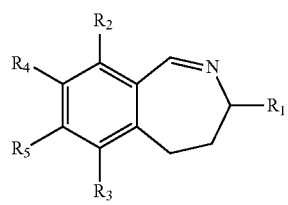

is described in Scheme 2. $R_1$, $R_2$, $R_3$, $R_4$, and $R_5$ in Scheme 2 are the same as those described in the Summary section above.

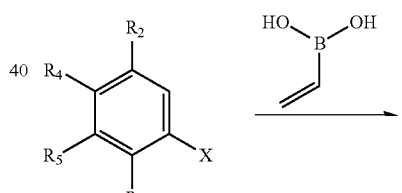

X is —Br
or
—OMs 2-1

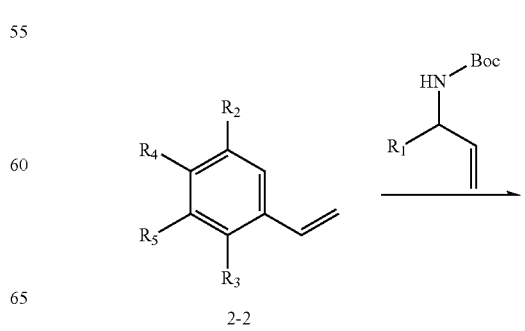

2-2

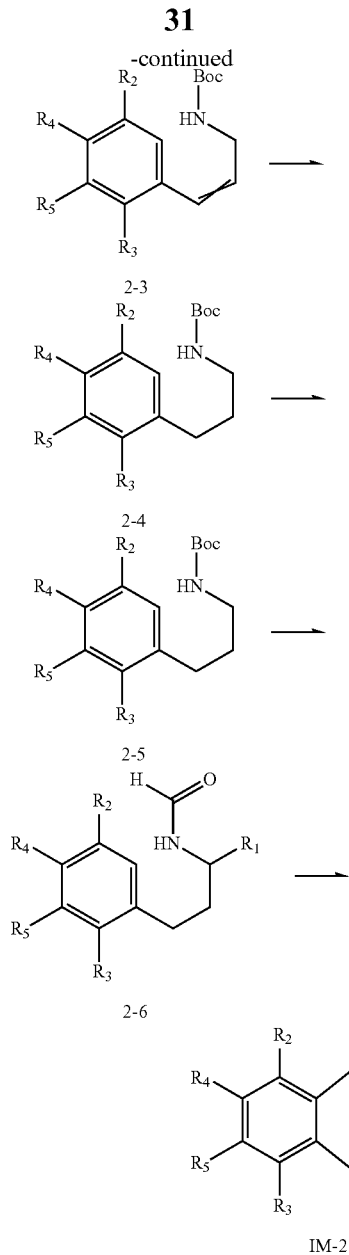

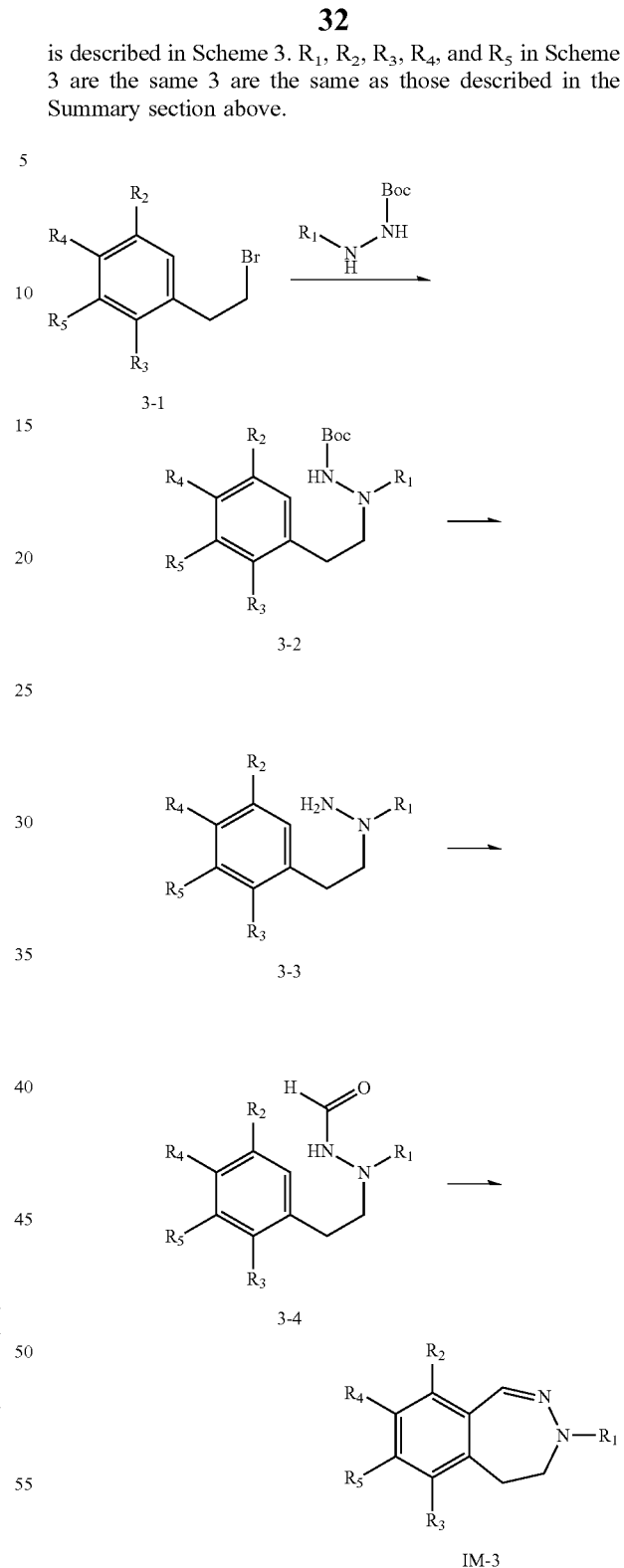

In Scheme 2, the appropriate starting material 2-1 can react with vinylboronic acid to give intermediate 2-2, which can undergo an olefin metathesis reaction to give intermediate 2-3. The reduction of 2-3 followed by a de-Boc process to yield the amine intermediate 2-5. After that, 2-5 is heated with ethyl formate or formic acid in a solvent such as ethanol or dioxane affords intermediate 2-6, which can undergo a cyclization reaction to form the imine intermediate IM-2.

A typical approach to synthesize of the intermediate is described in Scheme 3. $R_1$, $R_2$, $R_3$, $R_4$, and $R_5$ in Scheme 3 are the same 3 are the same as those described in the Summary section above.

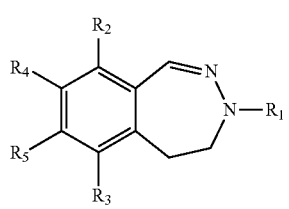

In Scheme 3, the appropriate starting material 3-1 can react with appropriate amine to give intermediate 3-2, which can undergo a de-Boc process to yield the amine intermediate 3-3. After that, 3-3 is heated with ethyl formate or formic acid in a solvent such as ethanol or dioxane affords intermediate 3-4, which can undergo a cyclization reaction to form the imine intermediate IM-3.

A typical approach to synthesize of the intermediate

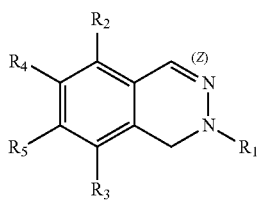

is described in Scheme 4. $R_1$, $R_2$, $R_3$, $R_4$, and $R_5$ in Scheme 4 are the same as those described in the Summary section above.

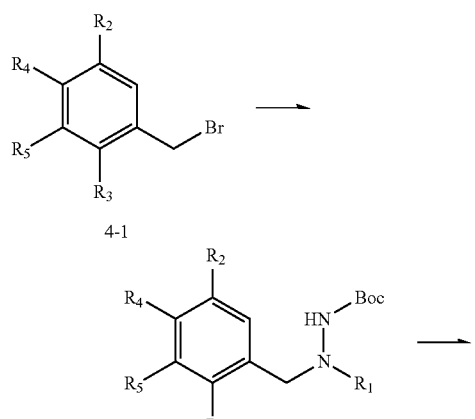

4-1

4-2

4-3

4-4

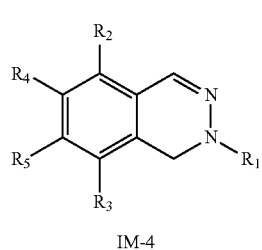

IM-4

In Scheme 4, the appropriate starting material 4-1 can react with appropriate amine to give intermediate 4-2, which can undergo a de-Boc process to yield the amine intermediate 4-3. After that, 4-3 is heated with ethyl formate or formic acid in a solvent such as ethanol or dioxane affords intermediate 4-4, which can undergo a cyclization reaction to form the imine intermediate IM-4.

A typical approach to synthesize of the intermediate

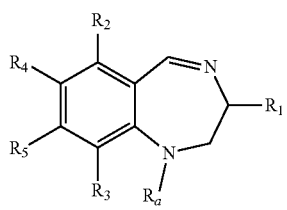

is described in Scheme 5. $R_1$, $R_2$, $R_3$, $R_4$, and $R_5$ in Scheme 5 are the same as those described in the Summary section above.

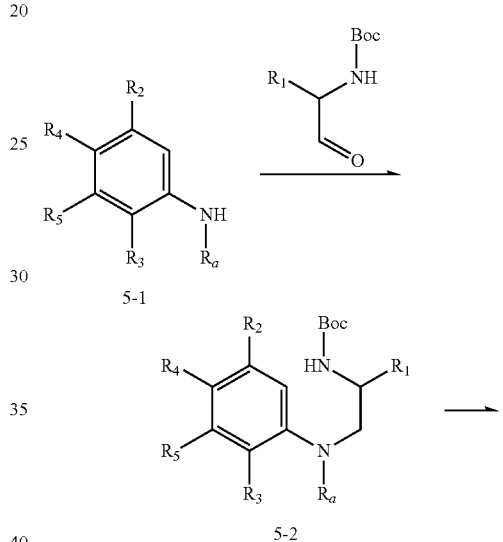

5-1

5-2

5-3

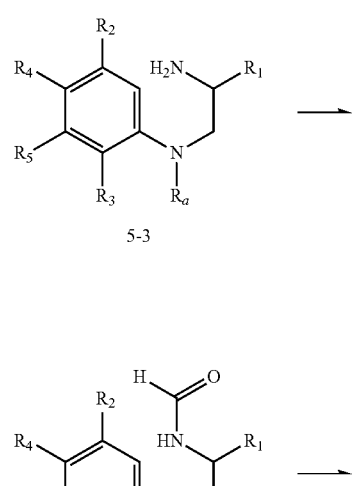

5-4

-continued

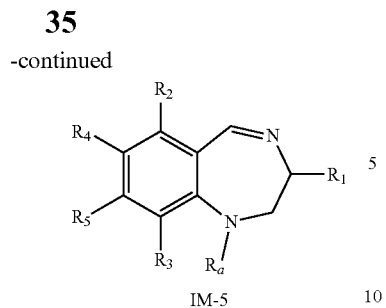

IM-5

In Scheme 5, the appropriate starting material 1-1 undergo a reductive animation reaction to give intermediate 5-2, which can undergo a de-Boc process to yield the amine intermediate 5-3. After that, 5-3 is heated with ethyl formate or formic acid in a solvent such as ethanol or dioxane affords intermediate 5-4, which can undergo a cyclization reaction to form the imine intermediate IM-5.

A typical approach to synthesize of the intermediate

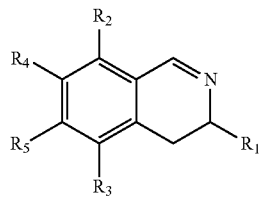

is described in Scheme 6. $R_1$, $R_2$, $R_3$, $R_4$, and $R_5$ in Scheme 4 are the same as those described in the Summary section above.

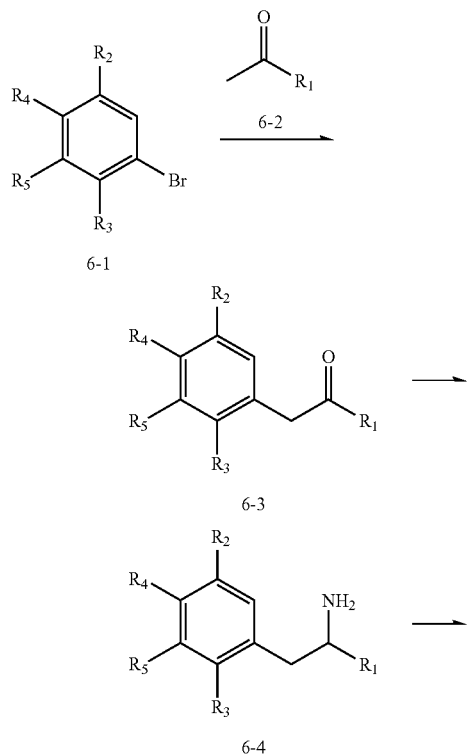

-continued

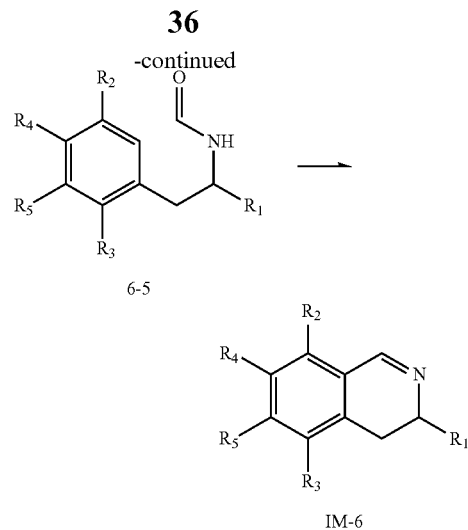

IM-6

In Scheme 6, the coupling reaction of 6-1 and 6-2 affords 6-3. The reaction can be carried out in the presence of Pd catalyst such as $Pd_2(dba)_3$, $Pd(PPh_3)_4$ or $PdCh(PPh_3)_2$, a ligand such as Xantphos, and a suitable base such as t-BuONa, $Na_2CO_3$ or $Cs_2CO_3$, in a suitable solvent such as THF, toluene or 1,4-dioxane at room temperature to 130° C. Reductive amination of 6-3 affords intermediate 6-4, which can be heated with ethyl formate or formic acid in a solvent such as ethanol or dioxane affords intermediate 6-5. After that, intermediate 6-5 is treated with oxalyl chloride followed by $FeCl_3$ at −10° C. to room temperature, and then after separation, the intermediate is heated with a solution of concentrated $H_2SO_4$ in methanol to give intermediate IM-6.

A typical approach to synthesize of the Formula (I) compounds

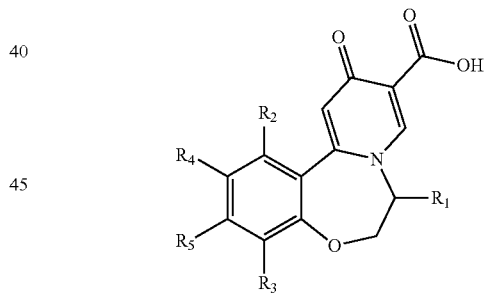

is described in Scheme A:

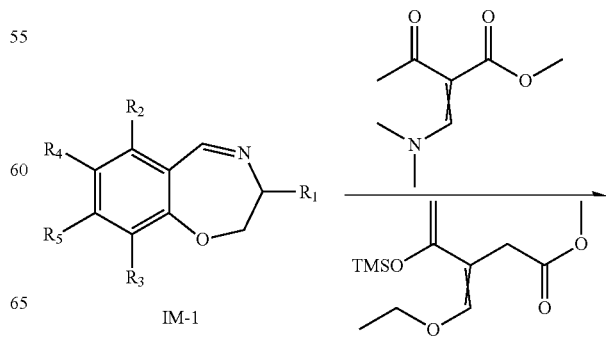

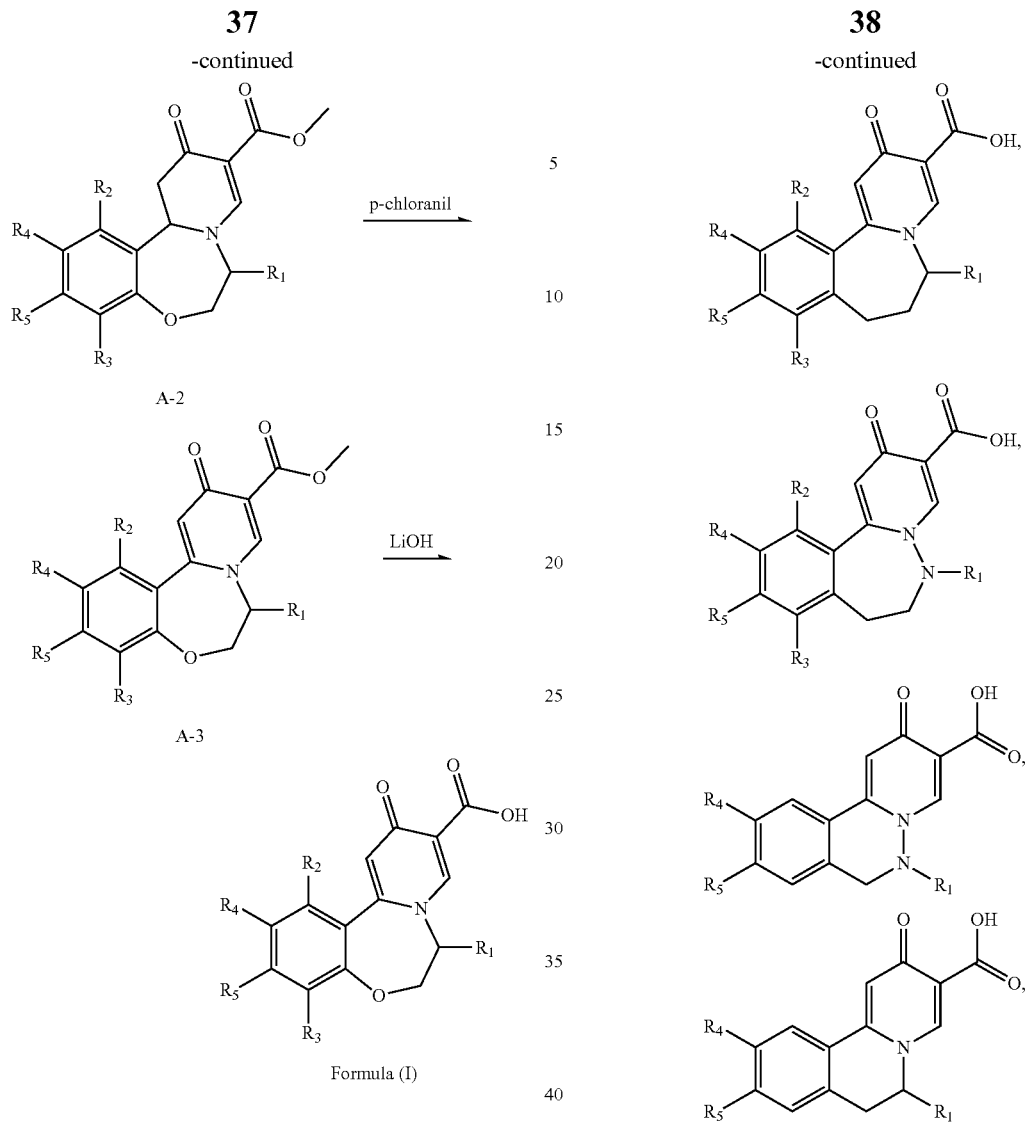

In Scheme A, IM-1 reacts with alkyl 2-(dimethylaminomethylene)-3-oxo-butanoate in a solvent such as DMSO, DMF, ethanol, or reacts with alkyl 3-(ethoxymethylene)-4-trimethylsilyloxy-pent-4-enoate, BF3-Et2O and TFA in DCM to give intermediate A-2. After dehydrogenation by p-chloranil, A-3 is obtained. Hydrolyzation of A-3 by lithium hydroxide or sodium hydroxide in a suitable solvent such as THF/H2O, EtOH/H2O or MeOH/H2O affords Formula (I) compound, which can be further separated by preparative HPLC and chiral HPLC to give isomers.

Similarly, the compounds as shown below

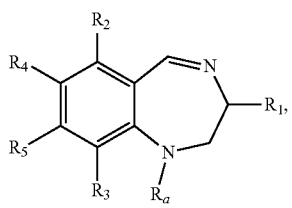

can be prepared by using the following appropriate intermediates, respectively.

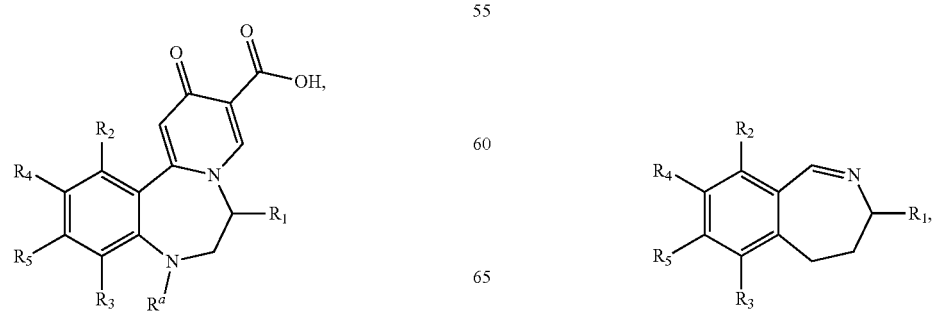

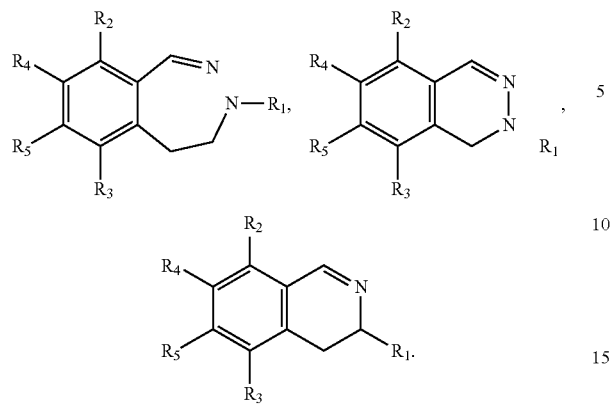

A typical approach to synthesize of the fluorized compounds

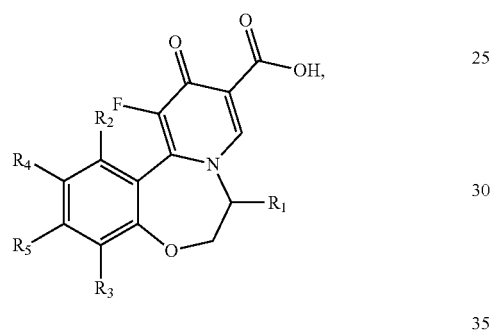

is described in Scheme B:

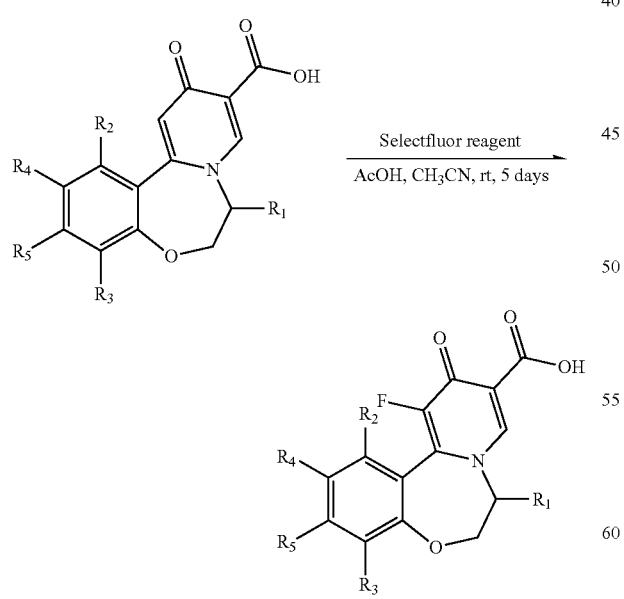

In Scheme B, the formula (I) compound can be one-step fluorized by a Selectfluor agent to afford the target compounds.

Similarly, the fluorized compounds as shown below

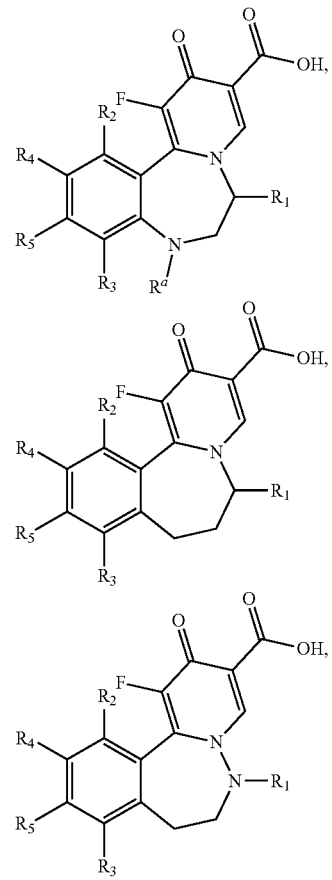

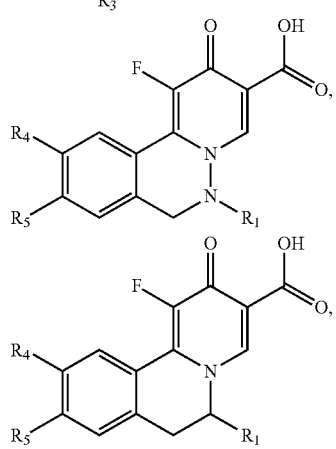

can be prepared by a fluorization reaction with a Selectfluor agent similar to Scheme B.

A preferred approach to synthesize of the compounds

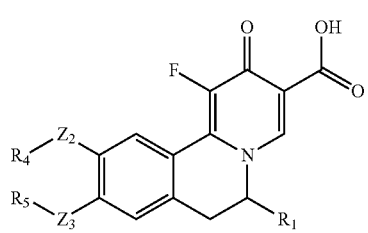

is described in Scheme I. $Z_2$, $Z_3$, $R_1$, $R_4$, and $R_5$ in Scheme I are the same as those described in the Summary section above.

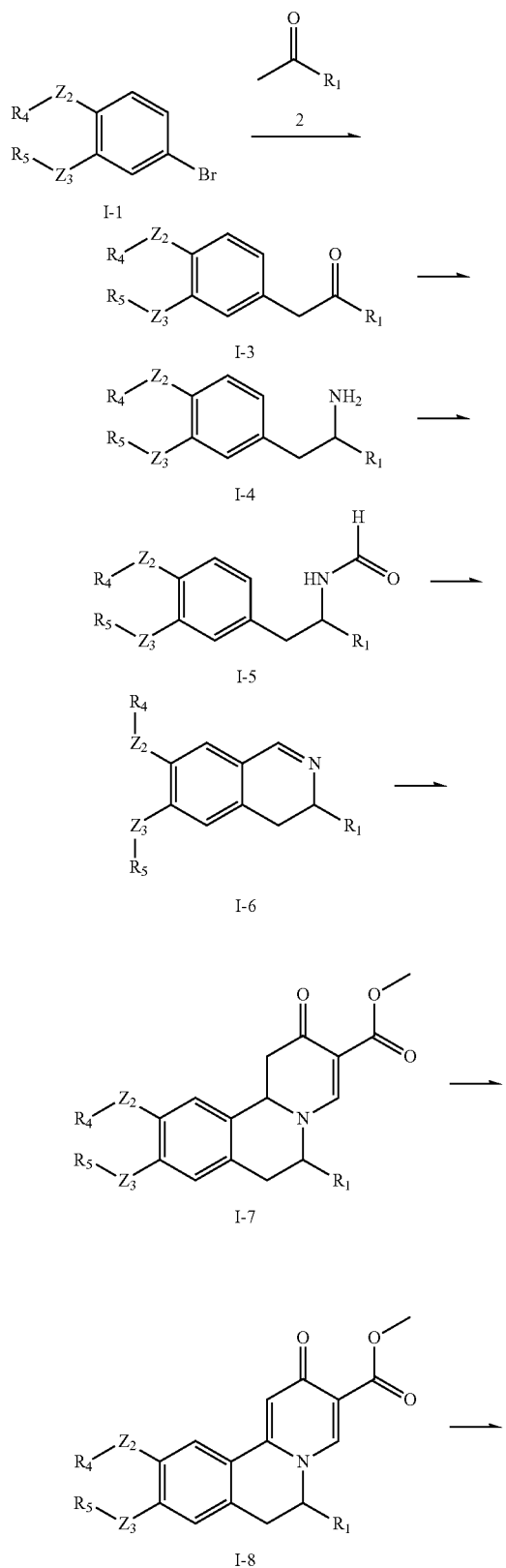

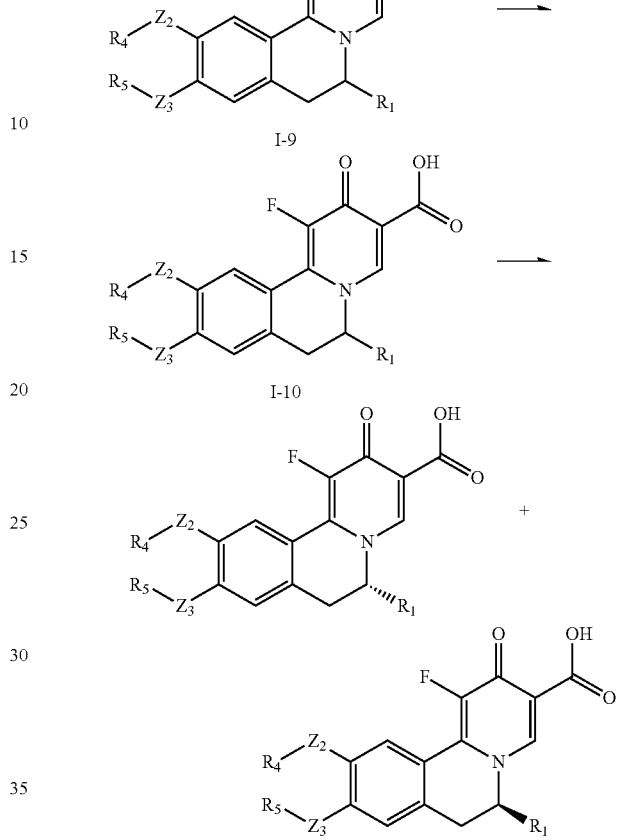

In Scheme I, the coupling reaction of appropriate staring material I-1 and I-2 affords I-3. The reaction can be carried out in the presence of Pd catalyst such as $Pd_2(dba)_3$, $Pd(PPh_3)_4$ or $PdCl_2(PPh_3)_2$, a ligand such as Xantphos, and a suitable base such as t-BuONa, $Na_2CO_3$ or $Cs_2CO_3$, in a suitable solvent such as THF, toluene or 1,4-dioxane at room temperature to 130° C. Reductive amination of 3 affords intermediate I-4, which can be heated with ethyl formate or formic acid in a solvent such as ethanol or dioxane affords intermediate I-5. After that, intermediate I-5 is treated with oxalyl chloride followed by $FeCl_3$ at −10° C. to room temperature, and then after separation, the intermediate is heated with a solution of concentrated $H_2SO_4$ in methanol to give intermediate I-6. Next, I-6 reacts with alkyl 2-(dimethylaminomethylene)-3-oxo-butanoate in a solvent such as DMSO, DMF, ethanol, or reacts with alkyl 3-(ethoxymethylene)-4-trimethylsilyloxy-pent-4-enoate, BF3-Et2O and TFA in DCM to give intermediate I-7. After dehydrogenation by p-chloranil, I-8 is obtained. Hydrolyzation of 8 by lithium hydroxide or sodium hydroxide in a suitable solvent such as THF/H2O, EtOH/H2O or MeOH/H2O affords intermediate I-9, which can be one-step fluorized by a Selectfluor agent to afford the target compound I-10. Finally I-10 can be further separated by preparative HPLC and chiral HPLC to give isomers.

A preferred approach to synthesize of the chiral compounds

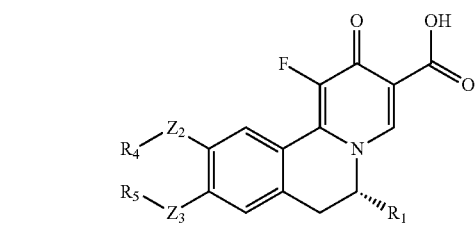

is described in Scheme II. $Z_2$, $Z_3$, $R_1$, $R_4$, and $R_5$ in Scheme II are the same as those described in the Summary section above.

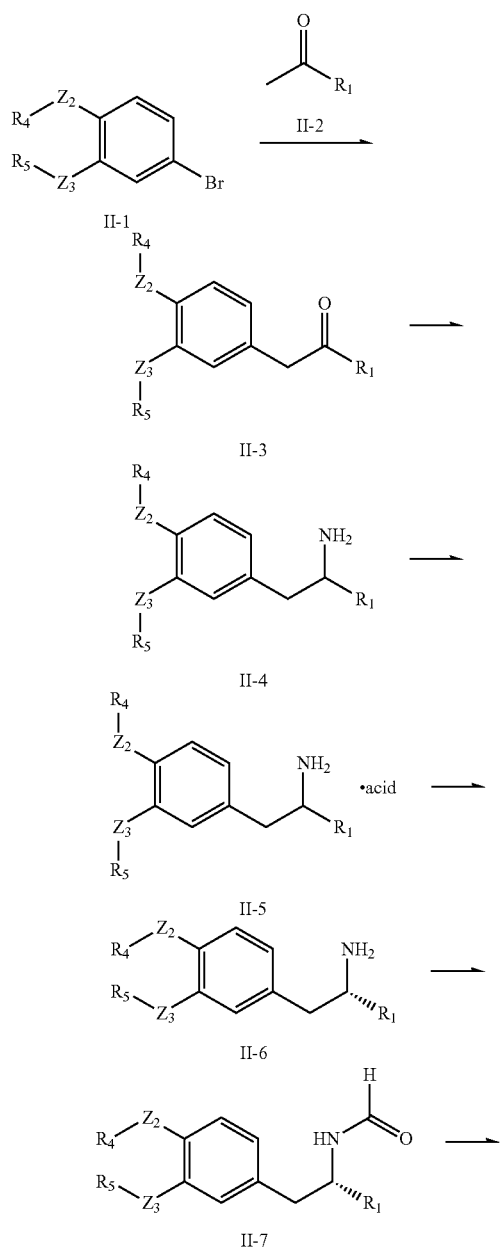

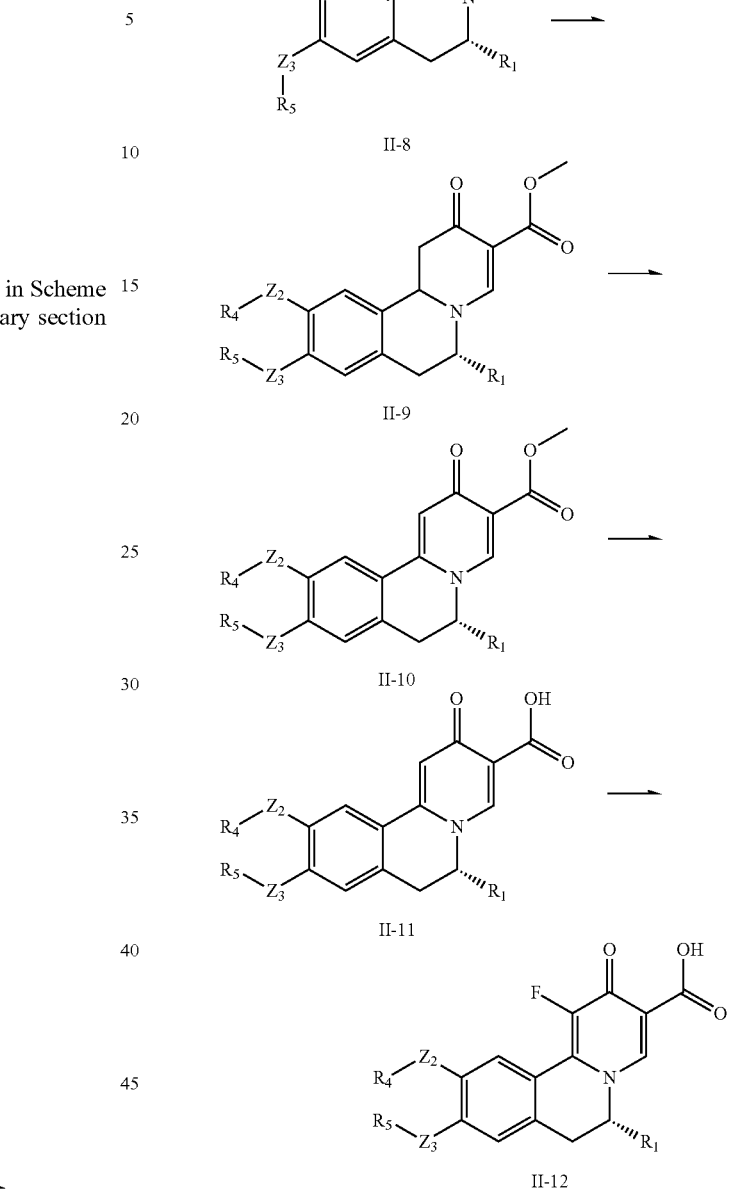

In Scheme II, the coupling reaction of appropriate staring material II-1 and II-2 affords II-3. The reaction can be carried out in the presence of Pd catalyst such as $Pd_2(dba)_3$, $Pd(PPh_3)_4$ or $PdCh(PPh_3)_2$, a ligand such as Xantphos, and a suitable base such as t-BuONa, $Na_2CO_3$ or $Cs_2CO_3$, in a suitable solvent such as THF, toluene or 1,4-dioxane at room temperature to 130° C. Reductive amination of 3 affords intermediate I-4, which can selectively form the enantiomeric salt II-5 with a suitable organic acid such as L-(+)-tartaric acid, L-(−)-DTTA, L-(−)-DBTA and (R)-mandelic acid in a suitable organic solvent such as MeOH, EtOH, IPA, IPAc, MIBK, EA, MTBE, DIPE, CPME and toluene. The other enantiomeric salt remains in the mother liquor. The recovery of enantiomeric salt II-5 leads to enantiomeric intermediate II-6, by reacting desired enantiomeric salt of II-5 with a suitable amount of base such as TEA, DIPEA, NaOH, $Na_2CO_3$, $NaHCO_3$ and a mixture thereof in a suitable solvent such as DCM, IPAc or MeTHF. After that, II-6 can be heated with ethyl formate or formic acid in a solvent such as ethanol or dioxane affords intermediate II-7, which can be treated with oxalyl chloride followed by FeCl₃ at −10° C. to room temperature, and then after separation, the intermediate is heated with a solution of concentrated H₂SO₄ in methanol to give intermediate II-8. Next, II-8 reacts with alkyl 2-(dimethylaminomethylene)-3-oxo-butanoate in a solvent such as DMSO, DMF, ethanol, or reacts with alkyl 3-(ethoxymethylene)-4-trimethylsilyloxy-pent-4-enoate, BF3-Et20 and TFA in DCM to give intermediate II-9. After dehydrogenation by p-chloranil, II-10 is obtained. Hydrolyzation of 10 by lithium hydroxide or sodium hydroxide in a suitable solvent such as THF/H20, EtOH/H20 or MeOH/H20 affords intermediate II-11, which can be one-step fluorized by a Selectfluor agent to afford the target compound II-12.

A preferred approach to synthesize the chiral Deuterium compounds

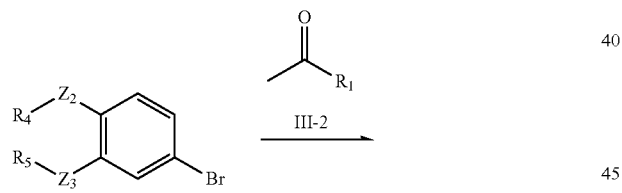

is described in Scheme III. $Z_2$, $Z_3$, $R_1$, $R_4$, and $R_5$ in Scheme III are the same as those described in the Summary section above.

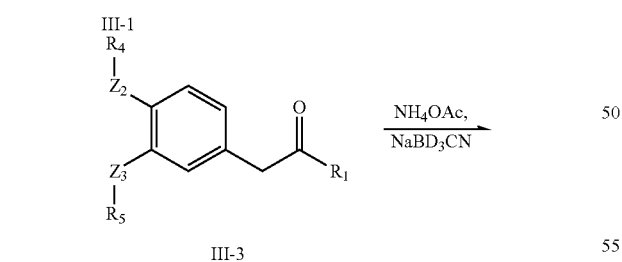

III-3

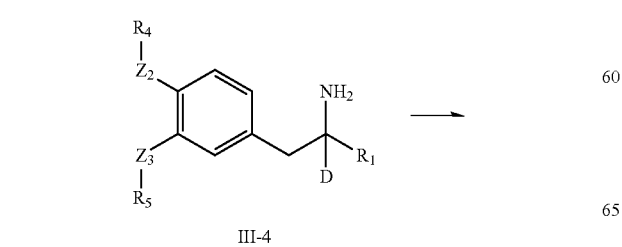

III-4

-continued

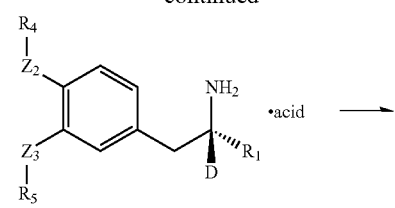

III-5

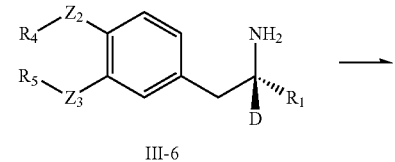

III-6

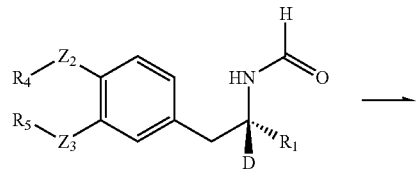

III-7

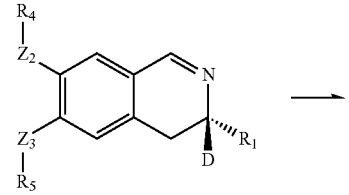

III-8

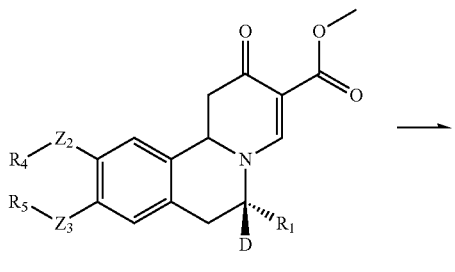

III-9

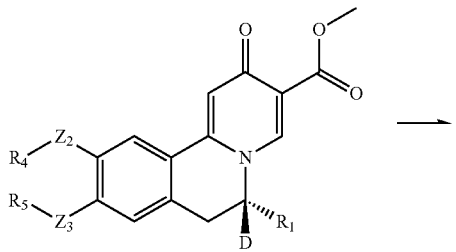

III-10

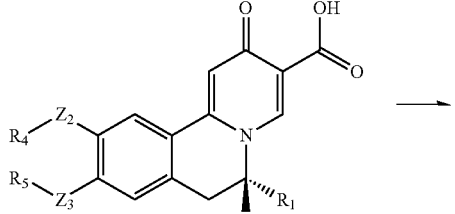

III-11

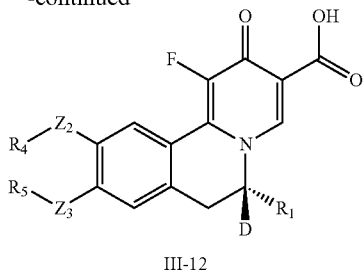

III-12

In Scheme III, the coupling reaction of appropriate staring material III-1 and III-2 affords III-3. The reaction can be carried out in the presence of Pd catalyst such as $Pd_2(dba)_3$, $Pd(PPh_3)_4$ or $PdCh(PPh_3)_2$, a ligand such as Xantphos, and a suitable base such as t-BuONa, $Na_2CO_3$ or $Cs_2CO_3$, in a suitable solvent such as THF, toluene or 1,4-dioxane at room temperature to 130° C. Reductive amination of 3 with appropriate Deuterium agent $NaBD_3CN$ affords intermediate I-4, which can selectively form the enantiomeric salt III-5 with a suitable organic acid such as L-(+)-tartaric acid, L-(-)-DTTA, L-(-)-DBTA and (R)-mandelic acid in a suitable organic solvent such as MeOH, EtOH, IPA, IPAc, MIBK, EA, MTBE, DIPE, CPME and toluene. The other enantiomeric salt remains in the mother liquor. The recovery of enantiomeric salt III-5 leads to enantiomeric intermediate III-6, by reacting desired enantiomeric salt of III-5 with a suitable amount of base such as TEA, DIPEA, NaOH, $Na_2CO_3$, $NaHCO_3$ and a mixture thereof in a suitable solvent such as DCM, IPAc or MeTHF. After that, III-6 can be heated with ethyl formate or formic acid in a solvent such as ethanol or dioxane affords intermediate III-7, which can be treated with oxalyl chloride followed by $FeCl_3$ at −10° C. to room temperature, and then after separation, the intermediate is heated with a solution of concentrated $H_2SO_4$ in methanol to give intermediate III-8. Next, III-8 reacts with alkyl 2-(dimethylaminomethylene)-3-oxo-butanoate in a solvent such as DMSO, DMF, ethanol, or reacts with alkyl 3-(ethoxymethylene)-4-trimethylsilyloxy-pent-4-enoate, BF3-Et20 and TFA in DCM to give intermediate III-9. After dehydrogenation by p-chloranil, III-10 is obtained. Hydrolyzation of 10 by lithium hydroxide or sodium hydroxide in a suitable solvent such as THF/H20, EtOH/H20 or MeOH/H20 affords intermediate III-11, which can be one-step fluorized by a Selectfluor agent to afford the target compound III-12.

A preferred approach to synthesize the chiral compounds

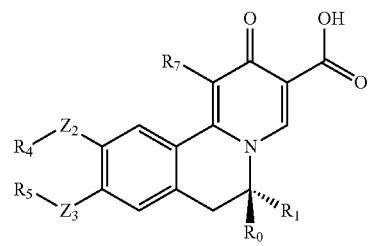

in which $R_0$ is H or D; and $R_7$ is halo, low alkyl, $CF_3$, CN, nitro, or $NH_2$, is described in Scheme IV. $Z_2$, $Z_3$, $R_1$, $R_4$, and $R_5$ in Scheme IV are the same as those described in the Summary section above.

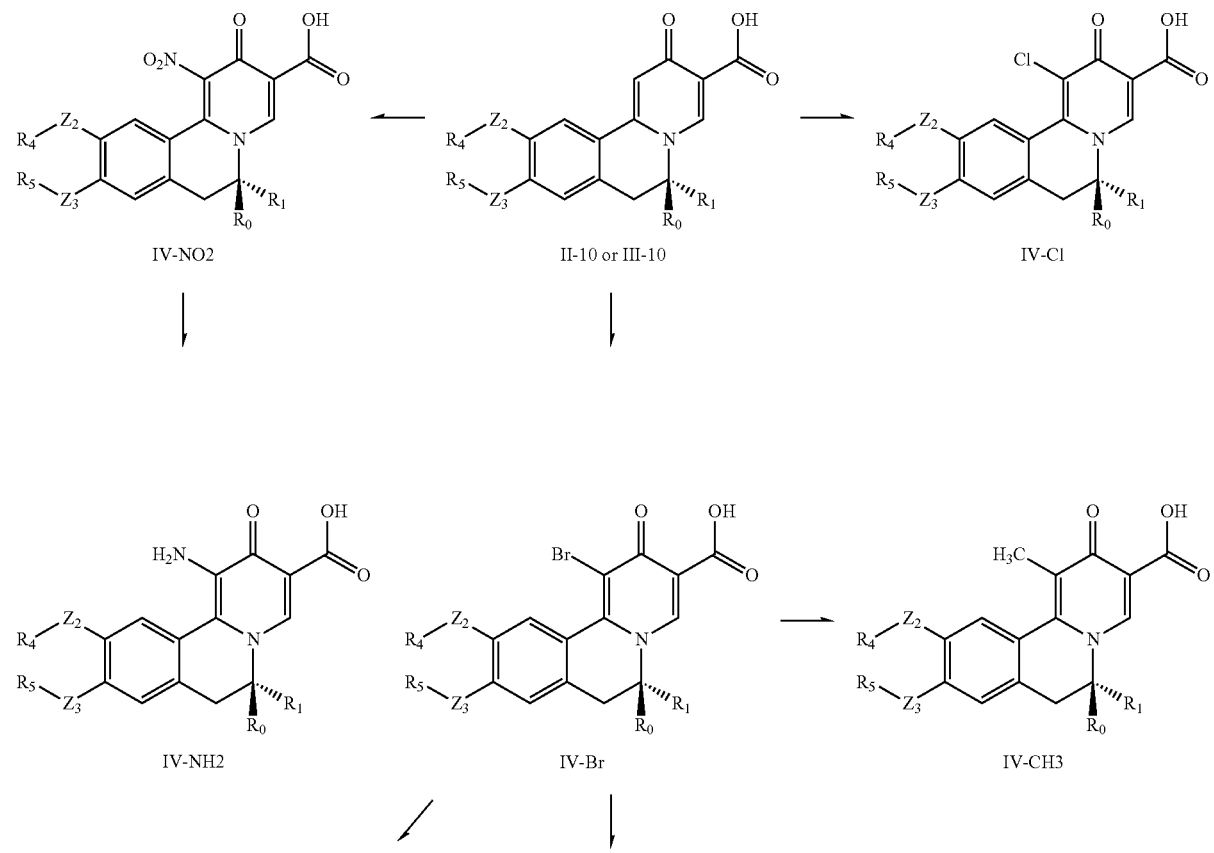

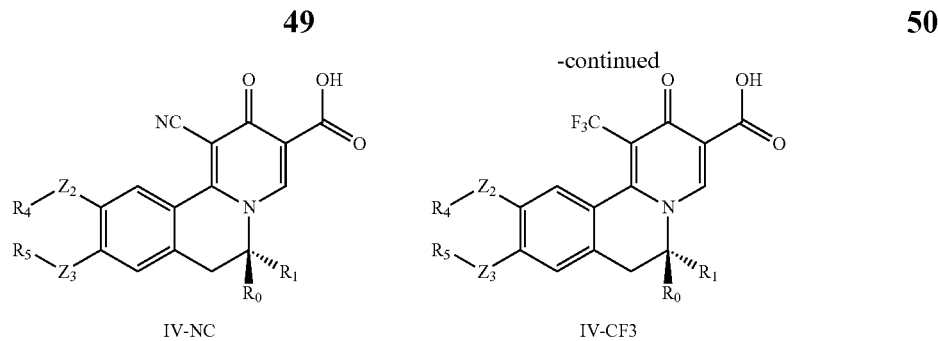

IV-NC        IV-CF3

In Scheme IV, the intermediate II-10 from Scheme II or III-10 from Scheme III can react with halogenation agents such as NCS or NBS to yield the compound IV-Cl or IV-Br (in which $R_7$ is Cl or Br); the compound IV-Br can be further one-step converted to IV-CN, IV-CF3, or IV-CH3 by standard organic reactions; in addition, the intermediate II-10 or III-10 can undergo a nitrosation reaction to yield the compound IV-NO$_2$ (in which $R_7$ is NO$_2$), which can be further reduced to yield IV-NH$_2$ (in which $R_7$ is NH$_2$).

A preferred approach to synthesize of the chiral compounds

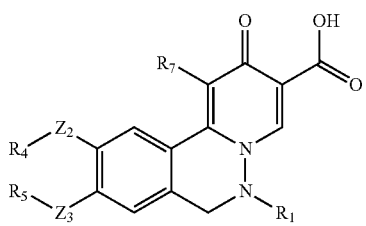

(in which $Z_2$ is O) is described in Scheme V. $Z_3$, $R_0$, $R_1$, $R_4$, $R_5$, and $R_7$ in Scheme V are the same as those described in the Summary section above.

A preferred approach to synthesize the compounds

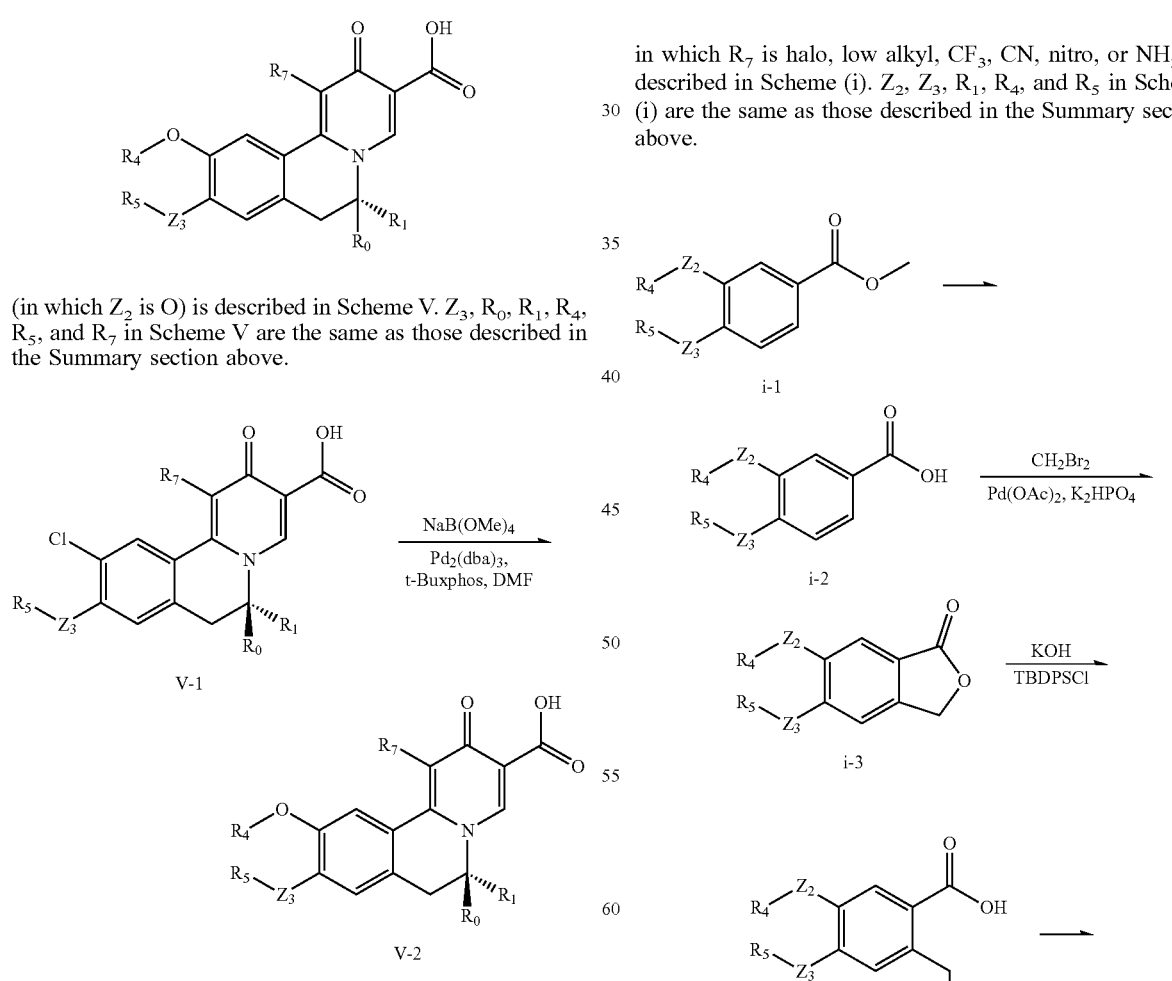

in which $R_7$ is halo, low alkyl, CF$_3$, CN, nitro, or NH$_2$, is described in Scheme (i). $Z_2$, $Z_3$, $R_1$, $R_4$, and $R_5$ in Scheme (i) are the same as those described in the Summary section above.

In Scheme V, V-1 (in which $R_4$—$Z_2$— is Cl) can be prepared by the methods similar to the Scheme I-III. After that, V-1 can react with the appropriate NaB(OR$_4$)$_4$ to afford the target compounds.

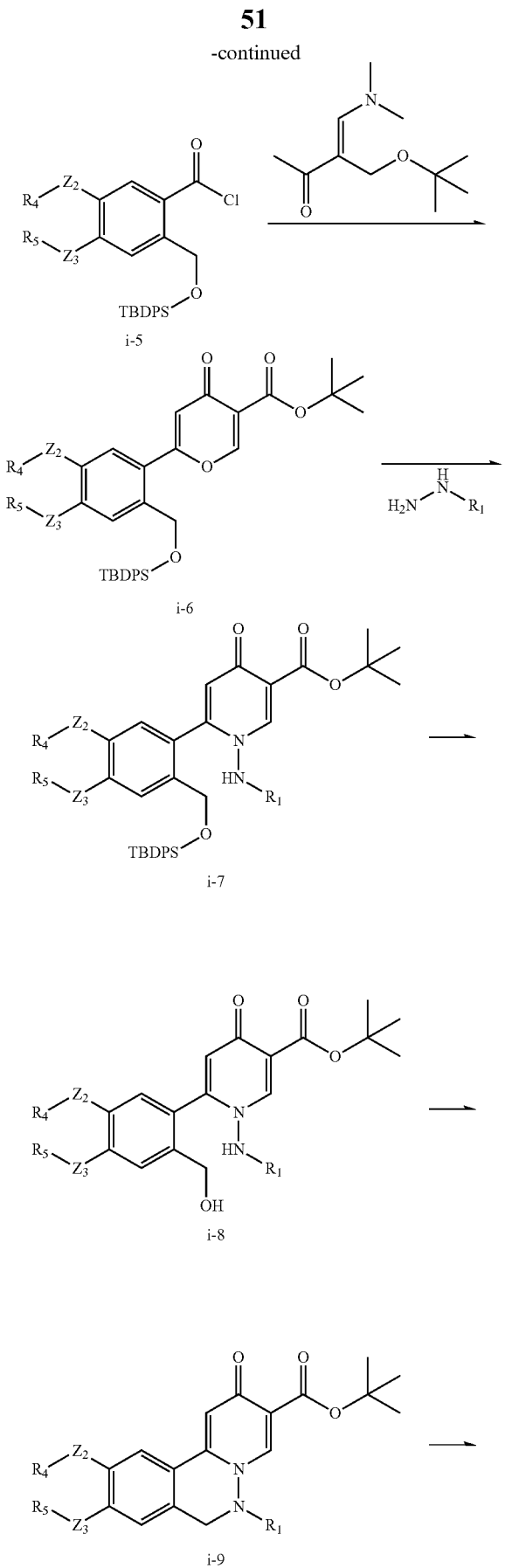
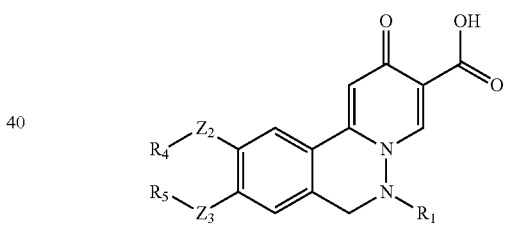

In Scheme (i), the staring material i-1 can undergo hydrolysis to yield carboxylic acid intermediate i-2, which is subsequently converted to lactone intermediate i-3. Lactone i-3 is hydrolyzed and protected to give carboxylic acid intermediate i-4, which is transformed into acid chloride intermediate i-5. Condensation with vinylic amine gives 4-pyranone intermediate i-6, which reacts with hydrazine to give intermediate i-7. Deprotection of i-7 and subsequent ring closure produces tricyclic intermediate i-9. Hydrolysis of i-9 gives carboxylic acid i-10, which can be finally functionalized using a method similar to Scheme I-IV wherein $R_7$ is not equal to H.

The compounds of in which $R_1$ is fluoroalkyl, fluorocycloalkyl, aryl, or heteroaryl, can be synthesized by a method similar to Scheme (i).

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column:

Example 1: Synthesis of 6-(tert-butyl)-10-chloro-1-fluoro-9-(3-methoxypropoxy)-2-oxo-6,7-dihydro-2H-pyrido[2,1-a]isoquinoline-3-carboxylic Acid

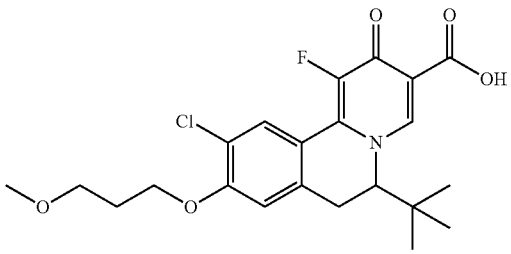

A mixture of 5-bromo-2-chloro-phenol (5.00 g, 24.10 mmol, 1.00 eq), 1-bromo-3-methoxy-propane (5.00 g, 32.68 mmol, 1.36 eq) and $K_2CO_3$ (9.99 g, 72.30 mmol, 3.00 eq) in DMF (50.00 mL) was stirred at 50° C. for 15 h. TLC (PE:EA=10:1) indicated the reaction completed. After filtration, the filtrate was concentrated under reduced pressure. The residue was purified by silica gel chromatography eluted with PE to PE:EA=5:1 to give 4-bromo-1-chloro-2-(3-methoxypropoxy)benzene (6.20 g, 22.18 mmol, 92.02% yield) as a colorless oil which was used directly in the next step.

A mixture of 4-bromo-1-chloro-2-(3-methoxypropoxy)benzene (4.00 g, 14.31 mmol, 1.00 eq), 3,3-dimethylbutan-2-one (4.30 g, 42.93 mmol, 5.31 mL, 3.00 eq), Pd(dba)$_2$ (411.42 mg, 715.50 umol, 0.05 eq), Xantphos (414.00 mg, 715.50 umol, 0.05 eq) and t-BuONa (4.54 g, 47.22 mmol, 3.30 eq) in THF (30.00 mL) was stirred at 50° C. for 3 h. After cooling to 30° C., the mixture was filtered. The filtrate was concentrated under reduced pressure to give crude 1-[4-chloro-3-(3-methoxypropoxy)phenyl]-3,3-dimethyl-butan-2-one (9.00 g, crude) as a brown oil which was used directly in the next step.

A mixture of crude 1-[4-chloro-3-(3-methoxypropoxy) phenyl]-3,3-dimethyl-butan-2-one (24.00 g, 56.22 mmol, 1.00 eq), $CH_3COONH_4$ (43.34 g, 562.20 mmol, 10.00 eq) and $NaBH_3CN$ (7.07 g, 112.44 mmol, 2.00 eq) in MeOH (300.00 mL) was stirred at 30° C. for 4 days. Sat. $K_2CO_3$ (100 mL) was added to the mixture, and the mixture was stirred at 30° C. for 20 min. The mixture was extracted with DCM (100 mL*3), and the combined organic layers were concentrated under reduced pressure. The crude product was purified by silica gel chromatography eluted with PE to PE:EA=1:1 to give 1-[4-chloro-3-(3-methoxypropoxy)phenyl]-3,3-dimethyl-butan-2-amine (13.20 g, 35.22 mmol, 62.64% yield, 80% purity) as a yellow oil which was confirmed by LC-MS and used directly in the next step.

A mixture of 1-[4-chloro-3-(3-methoxypropoxy)phenyl]-3,3-dimethyl-butan-2-amine (13.20 g, 30.82 mmol, 1.00 eq) and formic acid (1.70 g, 36.98 mmol, 1.40 mL, 1.20 eq) in HCOOEt (100.00 mL) was stirred at 90° C. for 15 h. After removal of the solvent, the residue was purified by silica gel chromatography eluted with PE to EA. N-[1-[[4-chloro-3-(3-methoxypropoxy)phenyl]methyl]-2,2-dimethyl-propyl] formamide (13.10 g, 25.97 mmol, 84.27% yield, 65% purity) was obtained as a light yellow solid which was confirmed by LC-MS.

A mixture of N-[1-[[4-chloro-3-(3-methoxypropoxy)phenyl]methyl]-2,2-dimethyl-propyl]formamide (3.10 g, 9.46 mmol, 1.00 eq) and POCl$_3$ (1.74 g, 11.35 mmol, 1.05 mL, 1.20 eq) in $CH_3CN$ (50.00 mL) was stirred at 60° C. for 2 h. After cooling to 0° C. by ice bath, the pH was adjusted to 8 by $NH_4OH$. The mixture was extracted with DCM (100 mL*2). The combined organic layers were concentrated under reduced pressure to give 3-tert-butyl-7-chloro-6-(3-methoxypropoxy)-3,4-dihydroisoquinoline (2.30 g, 7.42 mmol, 78.47% yield) as a brown oil which was used directly without further purification.

A mixture of 3-tert-butyl-7-chloro-6-(3-methoxypropoxy)-3,4-dihydroisoquinoline (2.30 g, 7.42 mmol, 1.00 eq) and ethyl (2E)-2-(methoxymethylene)-3-oxo-butanoate (5.11 g, 29.69 mmol, 4.00 eq) in EtOH (100.00 mL) was stirred at 100° C. for 22 h. After removal of the solvent, the residue was purified by silica gel chromatography eluted with PE:EA=10:1 to 1:1 to give crude ethyl 6-tert-butyl-10-chloro-9-(3-methoxypropoxy)-2-oxo-1,6,7,11b-tetrahydrobenzo[a]quinolizine-3-carboxylate (4.50 g, crude) as a brown oil which will be further purified together with EW5403-102 in EW5403-112 to give ethyl 6-tert-butyl-10-chloro-9-(3-methoxypropoxy)-2-oxo-1,6,7,11b-tetrahydrobenzo[a]quinolizine-3-carboxylate (4.78 g).

A mixture of ethyl 6-tert-butyl-10-chloro-9-(3-methoxypropoxy)-2-oxo-1,6,7,11b-tetrahydrobenzo[a]quinolizine-3-carboxylate (580.00 mg, 1.29 mmol, 1.00 eq) and 2,3,5,6-tetrachloro-1,4-benzoquinone (317.18 mg, 1.29 mmol, 1.00 eq) in DME (10.00 mL) was stirred at 70° C. for 1.5 h. After cooling to 30° C., $H_2O$ (60 mL) was added to the mixture. The mixture was extracted with DCM (50 mL*3). The combined organic layers were washed with sat. $NaHCO_3$ (100 mL), and concentrated under reduced pressure to give ethyl 6-tert-butyl-10-chloro-9-(3-methoxypropoxy)-2-oxo-6,7-dihydrobenzo[a]quinolizine-3-carboxylate (710.00 mg, crude) as a yellow solid which was used directly in the next step.

A mixture of ethyl 6-tert-butyl-10-chloro-9-(3-methoxypropoxy)-2-oxo-6,7-dihydrobenzo[a]-quinolizine-3-carboxylate (710.00 mg, 1.58 mmol, 1.00 eq) and NaOH (253.60 mg, 6.34 mmol, 4.00 eq) in MeOH (16.00 mL) and $H_2O$ (4.00 mL) was stirred at 30° C. for 40 min. The mixture was neutralized by aq. HCl (12 M in $H_2O$) to pH=7. The precipitate was filtered and dried to afford 6-tert-butyl-10-chloro-9-(3-methoxypropoxy)-2-oxo-6,7-dihydrobenzo[a] quinolizine-3-carboxylic acid (338.60 mg, 806.38 umol, 51.04% yield) as a light yellow solid which was confirmed by LC-MS and $^1$H NMR.

A mixture of 6-tert-butyl-10-chloro-9-(3-methoxypropoxy)-2-oxo-6,7-dihydrobenzo[a]quinolizine-3-carboxylic acid (400.00 mg, 952.61 umol, 1.00 eq), 1-(chloromethyl)-4-fluoro-1,4-diazoniabicyclo[2.2.2]octane; ditetrafluoroborate (401.59 mg, 1.13 mmol, 1.19 eq) were dissolved in the mixture of $CH_3CN$ (20 mL) and AcOH (2.10 g, 34.97 mmol, 2.00 mL, 36.71 eq). The mixture was stirred at 30° C. for 7 days. After removal of the solvent, the residue was purified by reverse phase column with HCOOH as additive, and then by Prep-HPLC (HCl) to give 6-(tert-butyl)-10-chloro-1-fluoro-9-(3-methoxypropoxy)-2-oxo-6, 7-dihydro-2H-pyrido[2,1-a]isoquinoline-3-carboxylic acid (13.50 mg, 3.24% yield) as an off-white solid. LC-MS: (M+H$^+$=438.0).$^1$H NMR: EW5403-147-P1B 400 MHz CDCl$_3$ δ 14.96 (s, 1H), 8.45 (s, 1H), 8.14 (s, 1H), 6.87 (s, 1H), 4.21-4.24 (m, 2H), 4.14 (s, 1H), 3.61-3.65 (m, 2H), 3.43-3.48 (m, 1H), 3.38 (s, 3H), 3.21-3.27 (m, 1H), 2.13-2.19 (m, 2H), 0.82 (s, 9H).

Example 2A and 2B: (+)-6-(tert-butyl)-10-chloro-1-fluoro-9-(3-methoxypropoxy)-2-oxo-6,7-dihydro-2H-pyrido[2,1-a]isoquinoline-3-carboxylic acid, and (−)-6-(tert-butyl)-10-chloro-1-fluoro-9-(3-methoxypropoxy)-2-oxo-6,7-dihydro-2H-pyrido[2,1-a]isoquinoline-3-carboxylic Acid

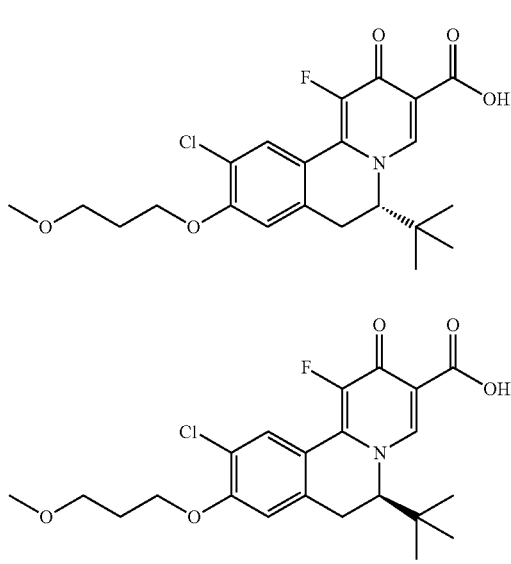

Separation of 6-(tert-butyl)-10-chloro-1-fluoro-9-(3-methoxypropoxy)-2-oxo-6,7-dihydro-2H-pyrido[2,1-a]isoquinoline-3-carboxylic acid by chiral HPLC provided (+)-6-(tert-butyl)-10-chloro-1-fluoro-9-(3-methoxypropoxy)-2-oxo-6,7-dihydro-2H-pyrido[2,1-a]isoquinoline-3-carboxylic acid, and (−)-6-(tert-butyl)-10-chloro-1-fluoro-9-(3-methoxypropoxy)-2-oxo-6,7-dihydro-2H-pyrido[2,1-a]isoquinoline-3-carboxylic acid.

2A: LC-MS: (M+H$^+$=438.0), [α]D$^{20}$=+51.23° (0.100%, CH$_3$CN). 2B: LC-MS: (M+H$^+$=438.0), [α]D$^{20}$=−56.347° (0.100%, CH$_3$CN).

Example 3: 6-(tert-butyl)-1,10-dichloro-9-(3-methoxypropoxy)-2-oxo-6,7-dihydro-2H-pyrido[2,1-a]isoquinoline-3-carboxylic Acid

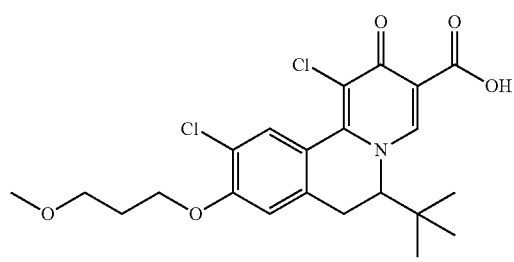

A mixture of 6-(tert-butyl)-10-chloro-9-(3-methoxypropoxy)-2-oxo-6,7-dihydro-2H-pyrido[2,1-a]isoquinoline-3-carboxylic acid (100.00 mg, 238.15 µmol, 1.00 eq) and NCS (95.40 mg, 714.45 µmol, 3.00 eq) in DCM (20.00 mL) was stirred at 15° C. for 3 days. After removal of the solvent, the residue was purified by Prep-HPLC (HCl as additive) to give 6-(tert-butyl)-1,10-dichloro-9-(3-methoxypropoxy)-2-oxo-6,7-dihydro-2H-pyrido[2,1-a]isoquinoline-3-carboxylic acid (4.10 mg, 9.02 µmol, 3.79% yield) as an off-white solid which was confirmed by LC-MS, $^1$H NMR and 2D NMRLC-MS: (M+H$^+$=454.1, M+2+H$^+$=456.1), 1HNMR: 400 MHz CDCl$_3$, δ 15.19 (s, 1H), 8.34 (s, 2H), 6.88 (s, 1H), 4.12-4.29 (m, 3H), 3.65-3.67 (m, 2H), 3.40 (s, 4H), 3.22-3.24 (m, 1H), 2.17-2.20 (m, 2H), 0.80 (s, 9H).

Example 4: 1-bromo-6-(tert-butyl)-10-chloro-9-(3-methoxypropoxy)-2-oxo-6,7-dihydro-2H-pyrido[2,1-a]isoquinoline-3-carboxylic Acid

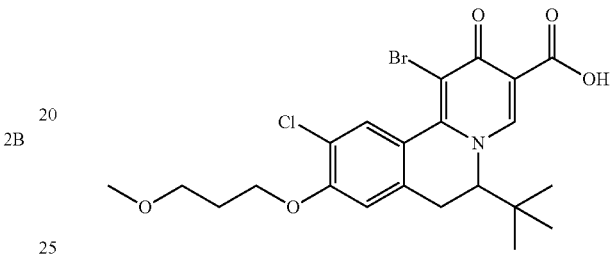

A mixture of 6-(tert-butyl)-10-chloro-9-(3-methoxypropoxy)-2-oxo-6,7-dihydro-2H-pyrido[2,1-a]isoquinoline-3-carboxylic acid (300.00 mg, 714.46 µmol, 1.00 eq) and NBS (254.32 mg, 1.43 mmol, 2.00 eq) in EA (10.00 mL) was stirred at 15° C. for 7 h After removal of the solvent, the residue was purified by Prep-HPLC (HCl as additive) to give 1-bromo-6-tert-butyl-10-chloro-9-(3-methoxypropoxy)-2-oxo-6,7-dihydrobenzo[a]quinolizine-3-carboxylic acid (52.00 mg, 104.25 µmol, 14.59% yield) as an off-white solid which was confirmed by LC-MS, $^1$H NMR and 2D NMR. LC-MS: (M+H$^+$=498.0, M+2+H$^+$=500.0), $^1$HNMR: 400 MHz CDCl$_3$, δ 8.61 (s, 1H), 8.54 (s, 1H), 6.86 (s, 1H), 4.28-4.30 (m, 2H), 4.20 (s, 1H), 3.63-3.67 (m, 2H), 3.41 (s, 4H), 3.22-3.24 (m, 1H), 2.15-2.21 (m, 2H), 0.79 (s, 9H).

Example 5: 6-(tert-butyl)-10-chloro-9-(3-methoxypropoxy)-1-methyl-2-oxo-6,7-dihydro-2H-pyrido[2,1-a]isoquinoline-3-carboxylic Acid

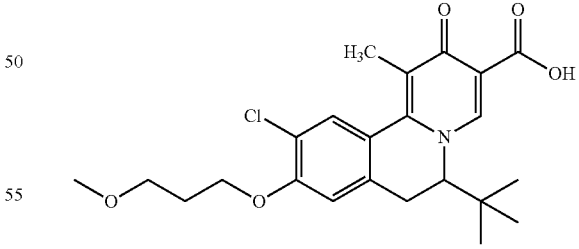

A mixture of 1-bromo-6-tert-butyl-10-chloro-9-(3-methoxypropoxy)-2-oxo-6,7-dihydrobenzo[a]quinolizine-3-carboxylic acid (55.00 mg, 110.27 µmol, 1.00 eq), 2,4,6-trimethyl-1,3,5,2,4,6-trioxatriborinane (138.42 mg, 1.10 mmol, 153.80 uL, 10.00 eq), Pd(PPh$_3$)$_4$ (127.42 mg, 110.27 µmol, 1.00 eq) and K$_2$CO$_3$ (76.20 mg, 551.33 µmol, 5.00 eq) in DMF (10.00 mL) was stirred at 110° C. for 11 h. After removal of the solvent, the residue was purified three times by Prep-TLC (EA) to give 6-(tert-butyl)-10-chloro-9-(3- methoxypropoxy)-1-methyl-2-oxo-6,7-dihydro-2H-pyrido[2,1-a]isoquinoline-3-carboxylic acid (2.80 mg, 6.45 umol, 5.85% yield) as a colorless oil which was confirmed by LC-MS and $^1$H NMR. LC-MS: (M+H$^+$=434.1), $^1$HNMR: 400 MHz CDCl$_3$, δ 8.71 (s, 1H), 7.84 (s, 1H), 7.23 (s, 1H), 4.22-4.31 (m, 2H), 3.61-3.65 (m, 3H), 3.37 (s, 3H), 3.35 (s, 1H), 2.90 (s, 1H), 2.44 (s, 3H), 2.27 (s, 1H), 2.09-2.13 (m, 2H), 0.75-0.77 (m, 9H).

Example 6: 6-(tert-butyl)-10-chloro-1-cyano-9-(3-methoxypropoxy)-2-oxo-6,7-dihydro-2H-pyrido[2,1-a]isoquinoline-3-carboxylic Acid

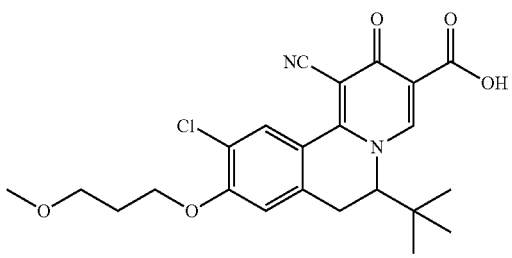

To a solution of ethyl 6-tert-butyl-10-chloro-9-(3-methoxypropoxy)-2-oxo-6,7-dihydrobenzo [a]quinolizine-3-carboxylate (1.50 g, 3.35 mmol, 1.00 eq) in EtOAc (20.00 mL), was added NBS (715.48 mg, 4.02 mmol, 1.20 eq). The mixture was stirred at 25° C. for 16 h. After removal of the solvent, the residue was purified by column chromatography (PE to PE/EA=0/1) to give ethyl 1-bromo-6-(tert-butyl)-10-chloro-9-(3-methoxypropoxy)-2-oxo-6,7-dihydro-2H-pyrido[2,1-a]isoquinoline-3-carboxylate (700.00 mg, 1.33 mmol, 39.70% yield) as a black brown solid which was was confirmed by LC-MS. (M+H$^+$=526.0, M+2+H$^+$=528.0)

To a solution of ethyl 1-bromo-6-tert-butyl-10-chloro-9-(3-methoxypropoxy)-2-oxo-6,7-dihydrobenzo[a]quinolizine-3-carboxylate (600 mg, 1.14 mmol, 1 eq) in DMF (30 mL), was added CuCN (122.40 mg, 1.37 mmol, 1.2 eq). The mixture was stirred at 170° C. for 3 h under N$_2$ atmosphere. After removal of the solvent, the residue was purified by column chromatography (PE to PE/EA=5/1) to give ethyl 6-(tert-butyl)-10-chloro-1-cyano-9-(3-methoxypropoxy)-2-oxo-6,7-dihydro-2H-pyrido[2,1-a]isoquinoline-3-carboxylate (502 mg, 1.06 mmol, 93.20% yield) as off-white oil which was confirmed by LC-MS. LC-MS: (M+H$^+$−14=459.1, note: the ethyl ester was exchanged to methyl ester in mass due to the solvent for mass was methanol)

To a solution of ethyl 6-(tert-butyl)-10-chloro-1-cyano-9-(3-methoxypropoxy)-2-oxo-6,7-dihydro-2H-pyrido[2,1-a]isoquinoline-3-carboxylate (502 mg, 1.06 mmol, 1 eq) in MeOH (30 mL) and H$_2$O (5 mL), was added NaOH (127.36 mg, 3.18 mmol, 3 eq). The mixture was stirred at 25° C. for 12 h. After removal of the solvent, the residue was purified by prep-HPLC (column: PhenomenexSynergi C18 150*25*10 μm; mobile phase: [water (0.05% HCl)-ACN]; B %: 48%-68%, 7.8 min) to give 6-(tert-butyl)-10-chloro-1-cyano-9-(3-methoxypropoxy)-2-oxo-6,7-dihydro-2H-pyrido[2,1-a]isoquinoline-3-carboxylic acid (58 mg, 130.36 μmol, 12.28% yield) as a light yellow solid which was confirmed by LC-MS and $^1$H NMR. (M+H$^+$=445.1). $^1$HNMR: 400 MHz CDCl$_3$, δ 14.42 (s, 1H), 8.76 (s, 2H), 6.90 (s, 1H), 4.05-4.28 (m, 3H), 3.62-3.63 (m, 2H), 3.28-3.39 (m, 4H), 2.17 (s, 1H), 2.02 (s, 2H), 0.82 (s, 9H).

Example 7: 6-isopropyl-10-methoxy-9-(3-methoxypropoxy)-1-nitro-2-oxo-6,7-dihydro-2H-pyrido[2,1-a]isoquinoline-3-carboxylic Acid

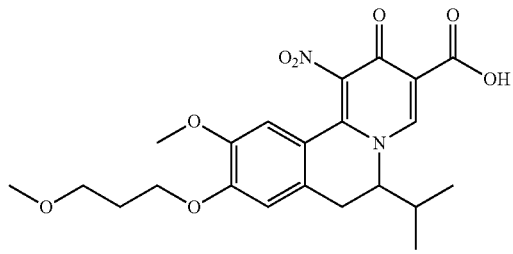 [SMILES: COCCCOc1cc2c(cc1OC)-c1c([N+](=O)[O-])c(=O)c(C(=O)O)cn1C(C(C)C)C2]

To a solution of 5-bromo-2-methoxy-phenol (67.00 g, 330.00 mmol, 1.00 eq) and 1-bromo-3-methoxy-propane (100.99 g, 660.00 mmol, 2.00 eq) in DMF (300.00 mL) was added K$_2$CO$_3$ (136.83 g, 990.00 mmol, 3.00 eq). The mixture was stirred at 25° C. for 8 h. Desired product was observed on LC-MS. The reaction mixture was concentrated in vacuo and extracted with ethyl acetate (40 mL*3). The crude product was purified by flash column (Petroleum ether/Ethyl acetate=5/1) to give 4-bromo-1-methoxy-2-(3-methoxypropoxy)benzene (90.00 g, 327.11 mmol, 99.12% yield) as a colorless oil. LC-MS: EW6108-59-P1Z (M+H$^+$=274.9, M+2+H$^+$=276.9)

To a solution of 4-bromo-1-methoxy-2-(3-methoxypropoxy)benzene (87.00 g, 316.20 mmol, 1.00 eq) and 3-methylbutan-2-one (27.23 g, 316.20 mmol, 33.62 mL, 1.00 eq) in dioxane (300.00 mL) was added Pd$_2$(dba)$_3$ (28.96 g, 31.62 mmol, 0.10 eq), Xantphos (36.59 g, 63.24 mmol, 0.20 eq) and t-BuONa (91.16 g, 948.61 mmol, 3.00 eq). The mixture was stirred at 100° C. for 4 h under N$_2$ atmosphere. After removal of the solvent, the mixture was added DCM (300 mL) and washed with H$_2$O (200 mL*3), and then concentrated under reduced pressure to give a residue. The crude was purified by flash column (Petroleum ether:Ethyl acetate=5:1) to give 1-(4-methoxy-3-(3-methoxypropoxy)phenyl)-3-methylbutan-2-one (34.25 g, 122.16 mmol, 38.64% yield) as brown oil and confirmed by LC-MS. LC-MS: EW6108-65-P1C1 (M+H$^+$=281.1)

To a solution of 1-(4-methoxy-3-(3-methoxypropoxy)phenyl)-3-methylbutan-2-one (35.00 g, 124.84 mmol, 1.00 eq) and CH$_3$COONH$_4$ (96.23 g, 1.25 mol, 10.00 eq) in MeOH (100.00 mL), was added NaBH$_3$CN (78.45 g, 1.25 mol, 10.00 eq). The mixture was stirred at 40° C. for 8 h. Desired product was observed on LC-MS. After removal of the solvent, the mixture was added EA (300 mL). The mixture was washed with H$_2$O (300 mL*3), and then concentrated under reduced pressure. The residue was purified by flash column (DCM:MeOH=50:1) to give 1-(4-methoxy-3-(3-methoxypropoxy)phenyl)-3-methylbutan-2-amine (24.12 g, 85.72 mmol, 68.66% yield) was obtained as yellow oil. LC-MS: EW6108-73-P1A1 (M+H$^+$=282.1)

A mixture of 1-(4-methoxy-3-(3-methoxypropoxy)phenyl)-3-methylbutan-2-amine (24.12 g, 85.72 mmol, 1.00 eq) and FORMIC ACID (39.46 g, 857.17 mmol, 32.34 mL, 10.00 eq) in dioxane (80.00 mL) was stirred at 100° C. for 6 h. Desired product was observed on LC-MS. The reaction mixture was concentrated in vacuo to give crude N-(1-(4-methoxy-3-(3-methoxypropoxy)phenyl)-3-methylbutan-2-yl)formamide (12.70 g, 41.05 mmol, 47.89% yield) as a yellow oil which was used directly in the next step. LC-MS: EW6108-74-P1Z01 (M+H$^+$=310.1)

To a solution of N-(1-(4-methoxy-3-(3-methoxypropoxy) phenyl)-3-methylbutan-2-yl)formamide (12.70 g, 41.05 mmol, 1.00 eq) in CH$_3$CN (100.00 mL), was added POCl$_3$ (31.47 g, 205.24 mmol, 19.07 mL, 5.00 eq). The mixture was stirred at 60° C. for 12 h. Desired product was observed on LC-MS. The reaction mixture was neutralized to pH=8 by NH$_4$OH and then extracted with DCM (100 mL*3). The organic layers were concentrated in vacuo to give a residue which was purified by reverse phase column with TFA as additive to give 3-isopropyl-7-methoxy-6-(3-methoxypropoxy)-3,4-dihydroisoquinoline (11.25 g, 38.61 mmol, 94.05% yield) as a yellow oil. LC-MS: EW6108-76-P1Z (M+H$^+$=292.1)

A mixture of 3-isopropyl-7-methoxy-6-(3-methoxypropoxy)-3,4-dihydroisoquinoline (11.25 g, 38.61 mmol, 1.00 eq) and ethyl (2E)-2-(ethoxymethylene)-3-oxo-butanoate (7.19 g, 38.61 mmol, 1.00 eq) in EtOH (30.00 mL) was stirred at 100° C. for 4 days. Desired product was observed on LC-MS. The reaction mixture was concentrated in vacuo to give a residue. The residue was purified by flash column (Ethyl acetate) to give ethyl 6-isopropyl-10-methoxy-9-(3-methoxypropoxy)-2-oxo-2,6,7,11b-tetrahydro-1H-pyrido[2,1-a]isoquinoline-3-carboxylate (12.25 g, 28.39 mmol, 73.53% yield) as a brown oil. LC-MS: EW6108-79-P1B (M+H$^+$=432.1)

To a solution of ethyl 6-isopropyl-10-methoxy-9-(3-methoxypropoxy)-2-oxo-2,6,7,11b-tetrahydro-1H-pyrido[2,1-a]isoquinoline-3-carboxylate (12.25 g, 28.39 mmol, 1.00 eq) in DME (50.00 mL) was added 2,3,5,6-tetrachloro-1,4-benzoquinone (13.96 g, 56.78 mmol, 2.00 eq). The mixture was stirred at 70° C. for 5 h. Desired product was observed on LC-MS. The reaction mixture was concentrated in vacuo to give a residue which was purified by flash column (DCM:MeOH=30:1) to give ethyl 6-isopropyl-10-methoxy-9-(3-methoxypropoxy)-2-oxo-6,7-dihydro-2H-pyrido[2,1-a]isoquinoline-3-carboxylate (8.10 g, 18.86 mmol, 66.43% yield) as a yellow oil. LC-MS: EW6108-82-P1A (M+H$^+$=430.1)

To a solution of ethyl 6-isopropyl-10-methoxy-9-(3-methoxypropoxy)-2-oxo-6,7-dihydro-2H-pyrido[2,1-a]isoquinoline-3-carboxylate (1.00 g, 2.33 mmol, 1.00 eq) in MeOH (5.00 mL) and H$_2$O (3.00 mL), was added NaOH (372.52 mg, 9.32 mmol, 4.00 eq). The mixture was stirred at 30° C. for 12 h. The reaction mixture was neutralized by HCl (12 M in H$_2$O) to pH=7. The solid was filtered out, and washed with H$_2$O (20 mL). The solid was purified by Prep-TLC (DCM:MeOH=15:1) to give 6-isopropyl-10-methoxy-9-(3-methoxypropoxy)-2-oxo-6,7-dihydro-2H-pyrido[2,1-a]isoquinoline-3-carboxylic acid (409.12 mg, 1.02 mmol, 43.74% yield) as an off-white solid and confirmed by LC-MS and $^1$H NMR. LC-MS: EW6108-83-P1M1 (M+H$^+$=402.2), $^1$HNMR: EW6108-83-P1M 400 MHz CDCl$_3$, δ 8.37 (s, 1H), 7.10 (s, 1H), 6.98 (s, 1H), 6.71 (s 1H), 4.12-4.09 (m, 2H), 3.86 (s, 3H), 3.81-3.75 (m, 1H), 3.56-3.47 (m, 2H), 3.32-3.23 (m, 4H), 3.03-2.96 (m, 1H) 2.12-2.04 (m, 2H), 1.80-1.70 (m, 1H), 0.85-0.9 (m, 3H), 0.80-0.70 (m, 3H).

To a solution of 6-isopropyl-10-methoxy-9-(3-methoxypropoxy)-2-oxo-6,7-dihydro-2H-pyrido[2,1-a]isoquinoline-3-carboxylic acid (100 mg, 249.10 μmol, 1 eq) in AcOH (20 mL) was added KNO$_3$ (25.18 mg, 249.10 μmol, 1 eq) and H$_2$SO$_4$ (1.84 g, 18.76 mmol, 1 mL, 75.31 eq). The mixture was stirred at 25° C. for 16 h. The reaction mixture was added to ice-water (300 mL), and extracted with DCM (50 mL*3), the combined organic layers were concentrated under reduced pressure to give a residue. The residue was purified by Prep-HPLC (column: PhenomenexSynergi C$_{18}$ 150*25*10 μm; mobile phase: [water (0.05% HCl)-ACN]; B %: 40%-60%, 7.8 min) to give 6-isopropyl-10-methoxy-9-(3-methoxypropoxy)-1-nitro-2-oxo-6,7-dihydro-2H-pyrido[2,1-a]isoquinoline-3-carboxylic acid (3.1 mg, 6.88 μmol, 2.76% yield) as black brown solid which was confirmed by LC-MS and $^1$H NMR. LC-MS: (M+H$^+$=447.1), 1HNMR: 400 MHz CDCl$_3$, δ 15.67 (s, 1H), 8.51 (s, 1H), 6.97 (s, 1H), 6.80 (s, 1H), 4.25-4.26 (m, 2H), 3.63-3.99 (m, 4H), 3.60-3.61 (m, 2H), 3.17-3.39 (m, 4H), 2.02-2.18 (m, 2H), 1.77-1.79 (m, 2H), 0.93-0.95 (m, 6H)

Example 8: 6-(tert-butyl)-10-chloro-9-(3-methoxypropoxy)-2-oxo-6,7-dihydro-2H-pyrido[2,1-a] phthalazine-3-carboxylic Acid

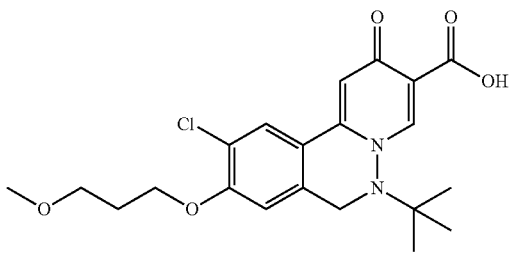 [SMILES: COCCCOc1cc2c(cc1Cl)-c1cc(=O)c(C(=O)O)cn1N(C(C)(C)C)C2]

Into a 250-mL 3-necked round-bottom flask, was placed a solution of methyl 3-chloro-4-hydroxybenzoate (10.0 g, 53.59 mmol, 1.00 equiv) in N,N-dimethylformamide (100 mL), 1-bromo-3-methoxypropane (12.3 g, 80.38 mmol, 1.50 equiv), potassium carbonate (22.3 g, 161.35 mmol, 3.00 equiv). The resulting solution was stirred for 3 h at 50° C. The reaction was then quenched by the addition of 100 mL of water. The resulting solution was extracted with 3×70 mL of ethyl acetate and the organic layers combined. The resulting mixture was washed with 3×100 mL of water and 1×100 mL of sodium chloride. The mixture was dried over anhydrous sodium sulfate. The solids were filtered out. The resulting mixture was concentrated under vacuum. The residue was applied onto a silica gel column with ethyl acetate/petroleum ether (1:2). This resulted in 13.1 g (94%) of methyl 3-chloro-4-(3-methoxypropoxy)benzoate as a orange solid. $^1$H NMR: PHNW-1-2-1 (300 MHz, DMSO) δ 7.91-7.87 (m, 2H), 7.25 (d, J=8.4 Hz, 1H), 4.19 (t, J=6.0 Hz, 2H), 3.86 (s, 3H), 3.50 (t, J=6.3 Hz, 2H), 3.25 (s, 3H), 2.04-2.00 (m, 2H).

Into a 250-mL round-bottom flask, was placed a solution of methyl 3-chloro-4-(3-methoxypropoxy)benzoate (13.1 g, 50.64 mmol, 1.00 equiv) in tetrahydrofuran/H$_2$O (120/40 mL), sodium hydroxide (4.06 g, 101.50 mmol, 2.00 equiv). The resulting solution was stirred overnight at 50° C. The resulting mixture was concentrated under vacuum. The pH value of the solution was adjusted to 5 with hydrogen chloride (3 mol/L). The solids were collected by filtration. This resulted in 11.1 g (90%) of 3-chloro-4-(3-methoxypropoxy)benzoic acid as a white solid. $^1$H NMR: PHNW-1-2-2 (300 MHz, DMSO), δ 12.97 (s, 1H), 7.92-7.86 (m, 2H), 7.24 (d, J=8.4 Hz, 1H), 4.19 (t, J=6.3 Hz, 2H), 3.50 (t, J=6.3 Hz, 2H), 3.25 (s, 3H), 2.04-1.96 (m, 2H).

Into a 250-mL 3-necked round-bottom flask purged and maintained with an inert atmosphere of nitrogen, was placed a solution of 3-chloro-4-(3-methoxypropoxy)benzoic acid (10.5 g, 42.91 mmol, 1.00 equiv) in CH$_2$Br$_2$ (150 mL), Pd(OAc)$_2$ (963.2 mg, 4.29 mmol, 0.10 equiv), K$_2$HPO$_4$ (15.0 g, 86.26 mmol, 2.00 equiv). The resulting solution was stirred overnight at 110° C. The resulting mixture was concentrated under vacuum. The residue was applied onto a silica gel column with ethyl acetate/petroleum ether (1:1). This resulted in 3.0 g (27%) of 6-chloro-5-(3-methoxypropoxy)-1,3-dihydro-2-benzofuran-1-one as a white solid. $^1$H NMR: PHNW-1-2-3 (300 MHz, DMSO), δ7.89 (s, 1H), 7.45 (s, 1H), 5.35 (s, 2H), 4.23 (t, J=6.3 Hz, 2H), 3.52 (t, J=6.3 Hz, 2H), 3.25 (s, 3H), 2.08-1.99 (m, 2 h).

Into a 100-mL round-bottom flask, was placed a solution of 6-chloro-5-(3-methoxypropoxy)-1,3-dihydro-2-benzofuran-1-one (3.0 g, 11.69 mmol, 1.00 equiv) in methanol (30 mL), potassium hydroxide (788 mg, 14.04 mmol, 1.20 equiv). The resulting solution was stirred overnight at 75° C. The resulting mixture was concentrated under vacuum. To the above was added TBDPS-Cl (6.42 g, 24.81 mmol, 2.00 equiv), 1H-imidazole (2.4 g, 35.25 mmol, 3.00 equiv), N,N-dimethylformamide (20 mL). The resulting solution was stirred 5 h at room temperature. The reaction was then quenched by the addition of 20 mL of water. The resulting solution was extracted with 3×30 mL of ethyl acetate and the organic layers combined. The resulting mixture was washed with 3×20 mL of water and 1×20 mL of sodium chloride. The mixture was dried over anhydrous sodium sulfate. The solids were filtered out. The resulting mixture was concentrated under vacuum. The residue was applied onto a silica gel column with ethyl acetate/petroleum ether (1:2). This resulted in 3.0 g (50%) of 2-[[(tert-butyldiphenylsilyl)oxy]methyl]-5-chloro-4-(3-methoxypropoxy)benzoic acid as a white solid. $^1$H NMR: PHNW-1-2-4 (300 MHz, DMSO), δ 12.89 (s, 1H), 7.90 (s, 1H), 7.66-7.64 (m, 5H), 7.51-7.41 (m, 6H), 5.13 (s, 2H), 4.20 (t, J=6.3 Hz, 2H), 3.50 (t, J=6.3 Hz, 2H), 3.25 (s, 3H), 2.07-1.99 (m, 2H), 1.08 (s, 9H).

Into a 250-mL round-bottom flask, was placed a solution of 2-[[(tert-butyldiphenylsilyl)oxy]methyl]-5-chloro-4-(3-methoxypropoxy)benzoic acid (5.0 g, 9.74 mmol, 1.00 equiv) in dichloromethane (50 mL), N,N-dimethylformamide (7 mg, 0.10 mmol, 0.01 equiv), oxalic dichloride (1.85 g, 14.58 mmol, 1.50 equiv). The resulting solution was stirred for 1 h at 0° C. The resulting mixture was concentrated under vacuum. This resulted in 5.0 g (crude) of 2-[[(tert-butyldiphenylsilyl)oxy]methyl]-5-chloro-4-(3-methoxypropoxy)benzoyl chloride as colorless oil.

Into a 250-mL 3-necked round-bottom flask purged and maintained with an inert atmosphere of nitrogen, was placed a solution of LDA (12.3 mL, 1.50 equiv, 1.2 mol/L) in tetrahydrofuran (50 mL). This was followed by the addition of a solution of tert-butyl (2Z)-2-[(dimethylamino)methylidene]-3-oxobutanoate (2.5 g, 11.72 mmol, 1.20 equiv) in tetrahydrofuran (20 mL) at −70° C. To this was added a solution of 2-[[(tert-butyldiphenylsilyl)oxy]methyl]-5-chloro-4-(3-methoxypropoxy)benzoyl chloride (5.2 g, 9.78 mmol, 1.00 equiv) in tetrahydrofuran (30 mL) at −70° C. in 30 min. To the mixture was added AcOH (25 mL), tert-butylhydrazine hydrochloride (2.43 g, 19.50 mmol, 2.00 equiv). The resulting solution was stirred overnight at 60° C. The resulting mixture was concentrated under vacuum. The residue was applied onto a silica gel column with ethyl acetate/petroleum ether (1:1). This resulted in 1.1 g (15%) of tert-butyl 1-(tert-butylamino)-6-(2-[[(tert-butyldiphenylsilyl)oxy]methyl]-5-chloro-4-(3-methoxypropoxy)phenyl)-4-oxo-1,4-dihydropyridine-3-carboxylate as brown oil. $^1$H NMR: PHNW-1-2-6 (300 MHz, CDCl$_3$) δ8.26 (s, 1H), 7.65-7.63 (m, 4H), 7.49-7.37 (m, 7H), 7.24 (s, 1H), 6.50 (s, 1H), 4.78 (s, 2H), 4.14 (t, J=6.3 Hz, 2H), 3.62 (t, J=6.3 Hz, 2H), 3.40 (s, 3H), 2.17-2.09 (m, 2H), 1.59 (s, 9H), 1.09 (s, 9H).

Into a 100-mL round-bottom flask, was placed a solution of tert-butyl 1-(tert-butylamino)-6-(2-[[(tert-butyldiphenylsilyl)oxy]methyl]-5-chloro-4-(3-methoxypropoxy)phenyl)-4-oxo-1,4-dihydropyridine-3-carboxylate (1.1 g, 1.50 mmol, 1.00 equiv) in tetrahydrofuran (10 mL), TBAF/THF (2.25 mL, 1 mol/L, 1.50 equiv). The resulting solution was stirred for 2 h at room temperature. The resulting mixture was concentrated under vacuum. The residue was applied onto a silica gel column with ethyl acetate/petroleum ether (2:1). This resulted in 510 mg (69%) of tert-butyl 1-(tert-butylamino)-6-[5-chloro-2-(hydroxymethyl)-4-(3-methoxypropoxy)phenyl]-4-oxo-1,4-dihydropyridine-3-carboxylate as colorless oil. $^1$H NMR: PHNW-1-2-7 (300 MHz, DMSO), δ 8.35 (s, 1H), 7.72 (s, 1H), 7.54 (s, 1H), 5.76 (s, 1H), 5.39 (t, J=5.1 Hz, 1H), 4.97 (s, 2H), 4.70 (d, J=5.4 Hz, 2H), 4.23 (t, J=6.3 Hz, 2H), 3.52 (t, J=6.3 Hz, 2H), 3.27 (s, 3H), 2.08-1.99 (m, 2H), 1.55 (m, 9H), 1.36 (s, 9H).

Into a 50-mL round-bottom flask, was placed a solution of tert-butyl 1-(tert-butylamino)-6-[5-chloro-2-(hydroxymethyl)-4-(3-methoxypropoxy)phenyl]-4-oxo-1,4-dihydropyridine-3-carboxylate (510 mg, 1.03 mmol, 1.00 equiv) in dichloromethane (5 mL), TEA (156.4 mg, 1.55 mmol, 1.50 equiv), methanesulfonyl chloride (129.5 mg, 1.13 mmol, 1.10 equiv). The resulting solution was stirred overnight at 25° C. The resulting mixture was concentrated under vacuum. The residue was applied onto a silica gel column with ethyl acetate/petroleum ether (1:1). This resulted in 210 mg (43%) of tert-butyl 6-tert-butyl-10-chloro-9-(3-methoxypropoxy)-2-oxo-2H,6H,7H-pyrido[2,1-a]phthalazine-3-carboxylate as a light yellow solid. $^1$H NMR: PHNW-1-2-8 (300 MHz, DMSO) δ 8.14 (s, 1H), 7.66 (s, 1H), 7.29 (s, 1H), 6.06 (s, 1H), 5.28 (s, 2H), 4.16 (t, J=6.3 Hz, 2H), 3.53-3.47 (m, 2H), 3.26 (s, 3H), 2.05-1.97 (m, 2H), 1.59 (s, 9H), 1.32 (s, 9H).

Into a 50-mL round-bottom flask, was placed a solution of tert-butyl 6-tert-butyl-10-chloro-9-(3-methoxypropoxy)-2-oxo-2H,6H,7H-pyrido[2,1-a]phthalazine-3-carboxylate (100 mg, 0.21 mmol, 1.00 equiv) in dichloromethane (2.5 mL), trifluoroacetic acid (0.5 mL). The resulting solution was stirred overnight at room temperature. The resulting mixture was concentrated under vacuum. The crude product was purified by Prep-HPLC with the following conditions (SHIMADZU(HPLC-10)): Column, X Bridge Prep C18 OBD Column 19*150 mm 5 μm C-0013; mobile phase, A: Water (it contains 0.1% FA); B: CH3CN; Gradient: 14 min in 80% B to 95% B (Flow rate: 20 mL/min) Detector: 254 nm. This resulted in 20 mg (23%) of 6-tert-butyl-10-chloro-9-(3-methoxypropoxy)-2-oxo-2H,6H,7H-pyrido[2,1-a]phthalazine-3-carboxylic acid as a white solid. $^1$H NMR: PHNW-1-2-0 (300 MHz, DMSO) δ11.78 (br, 1H), 8.14 (s, 1H), 7.69 (s, 1H), 7.26 (s, 1H), 6.06 (s, H), 5.26 (s, 2H), 4.16 (t, J=6.3 Hz, 2H), 3.51 (t, J=6.3 Hz, 2H), 3.26 (s, 3H), 2.05-1.97 (m, 2H), 1.59 (s, 9H), 1.55 (s, 1H).

Example 9: (S)-1-fluoro-6-isopropyl-10-methoxy-9-(3-methoxypropoxy)-2-oxo-6,7-dihydro-2H-pyrido[2,1-a]isoquinoline-3-carboxylic Acid

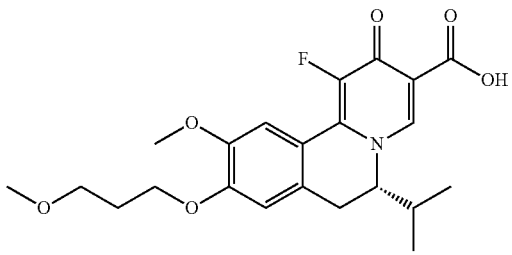 [SMILES: COCCCOc1cc2c(cc1OC)-c1c(F)c(=O)c(C(=O)O)cn1[C@H](C(C)C)C2]

Into a 100-mL round-bottom flask, was placed a solution of ethyl 10-methoxy-9-(3-methoxypropoxy)-2-oxo-6-(propan-2-yl)-2H,6H,7H-pyrido[2,1-a]isoquinoline-3-carboxylate (900 mg, 2.10 mmol, 1.00 equiv) in acetic acid (20 mL). This was followed by the addition of F-TEDA-BF4 (4.5 g, 12.71 mmol, 6.00 equiv), in portions. The resulting solution was stirred for 72 h at 50° C. in an oil bath. The resulting mixture was concentrated under vacuum. The crude product was purified by Prep-HPLC with the following conditions (Waters XBridge): Column, RP18 19*150 mm, 5 μm; mobile phase, A: 0.05% $NH_3.H_2O$ B: ACN; Detector, UV254 nm & 220 nm. This resulted in 70 mg (7%) of ethyl 1-fluoro-6-isopropyl-10-methoxy-9-(3-methoxypropoxy)-2-oxo-6,7-dihydro-2H-pyrido[2,1-a]isoquinoline-3-carboxylate as a white solid. LC-MS (M+1): 448; RT=1.78 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Into a 50-mL round-bottom flask, was placed a solution of ethyl 1-fluoro-6-isopropyl-10-methoxy-9-(3-methoxypropoxy)-2-oxo-6,7-dihydro-2H-pyrido[2,1-a]isoquinoline-3-carboxylate (70 mg, 0.16 mmol, 1.00 equiv) in methanol (5 mL). The resulting solution was purified by Chiral-Prep-HPLC with the following conditions (SHIMADZU LC-20AD): Column, CHIRALPAK AD-3; Phase A: ethanol; Phase B: Methanol; Detector, SPD-M20A, 190 nm-500 nm. This resulted in 28 mg (38%) of ethyl (S)-1-fluoro-6-isopropyl-10-methoxy-9-(3-methoxypropoxy)-2-oxo-6,7-dihydro-2H-pyrido[2,1-a]isoquinoline-3-carboxylate as a white solid. LC-MS (M+1): 448; RT=1.33 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Into a 50-mL round-bottom flask, was placed a solution of ethyl (S)-1-fluoro-6-isopropyl-10-methoxy-9-(3-methoxypropoxy)-2-oxo-6,7-dihydro-2H-pyrido[2,1-a]isoquinoline-3-carboxylate (28 mg, 0.07 mmol, 1.00 equiv) in methanol/$H_2O$ (2/0.2 mL). This was followed by the addition of sodium hydroxide (10 mg, 0.25 mmol, 4.00 equiv), in portions. The resulting solution was stirred for 2 h at 40° C. in an oil bath. The resulting mixture was concentrated under vacuum. The resulting solution was diluted with 3 mL of water. The pH value of the solution was adjusted to 6-5 with acetic acid (100%). The resulting solution was extracted with 3×10 mL of ethyl acetate and the organic layers combined. The organic layer was dried over anhydrous sodium sulfate and concentrated under vacuum. This resulted in 18 mg (66%) of (S)-1-fluoro-6-isopropyl-10-methoxy-9-(3-methoxypropoxy)-2-oxo-6,7-dihydro-2H-pyrido[2,1-a]isoquinoline-3-carboxylic acid as a white solid. LC-MS (M+1): 420; RT=1.37 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (300 MHz, CDCl3, ppm): δ 15.0 (bs, 1H), 8.46 (s, 1H), 7.65 (s, 1H), 6.84 (s, 1H), 4.26-4.23 (m, 2H), 3.94-3.90 (m, 4H), 3.63-3.61 (m, 2H), 3.39-3.35 (m, 4H), 3.11-3.06 (m, 1H), 2.19-2.11 (m, 2H), 1.86-1.82 (m, 1H), 0.96 (d, J=8.4 Hz, 3H), 0.86 (d, J=8.4 Hz, 3H).

Example 10: (R)-1-fluoro-6-isopropyl-10-methoxy-9-(3-methoxypropoxy)-2-oxo-6,7-dihydro-2H-pyrido[2,1-a]isoquinoline-3-carboxylic Acid

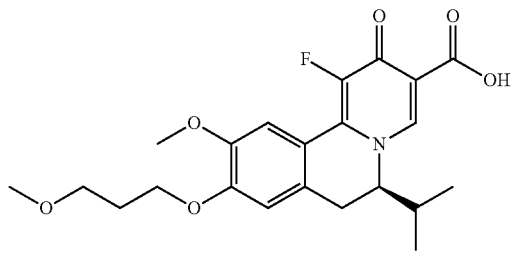 [SMILES: COCCCOc1cc2c(cc1OC)-c1c(F)c(=O)c(C(=O)O)cn1[C@@H](C(C)C)C2]

Into a 50-mL round-bottom flask, was placed a solution of ethyl 1-fluoro-6-isopropyl-10-methoxy-9-(3-methoxypropoxy)-2-oxo-6,7-dihydro-2H-pyrido[2,1-a]isoquinoline-3-carboxylate (70 mg, 0.16 mmol, 1.00 equiv) in methanol (5 mL). The resulting solution was purified by Chiral-Prep-HPLC with the following conditions (SHIMADZU LC-20AD): Column, CHIRALPAK AD-3; Phase A: ethanol; Phase B: Methanol; Detector, SPD-M20A, 190 nm-500 nm. This resulted in 28 mg (38%) of ethyl (R)-1-fluoro-6-isopropyl-10-methoxy-9-(3-methoxypropoxy)-2-oxo-6,7-dihydro-2H-pyrido[2,1-a]isoquinoline-3-carboxylate as a white solid. LC-MS (M+1): 448; RT=1.33 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Into a 50-mL round-bottom flask, was placed a solution of ethyl (R)-1-fluoro-6-isopropyl-10-methoxy-9-(3-methoxypropoxy)-2-oxo-6,7-dihydro-2H-pyrido[2,1-a]isoquinoline-3-carboxylate (28 mg, 0.07 mmol, 1.00 equiv) in methanol/$H_2O$ (2/0.2 mL). This was followed by the addition of sodium hydroxide (10 mg, 0.25 mmol, 4.00 equiv), in portions. The resulting solution was stirred for 2 h at 40° C. in an oil bath. The resulting mixture was concentrated under vacuum. The resulting solution was diluted with 3 mL of water. The pH value of the solution was adjusted to 6-5 with acetic acid (100%). The resulting solution was extracted with 3×10 mL of ethyl acetate and the organic layers combined. The organic layer was dried over anhydrous sodium sulfate and concentrated under vacuum. This resulted in 18 mg (66%) of (R)-1-fluoro-6-isopropyl-10-methoxy-9-(3-methoxypropoxy)-2-oxo-6,7-dihydro-2H-pyrido[2,1-a]isoquinoline-3-carboxylic acid as a white solid. LC-MS (M+1): 420; RT=1.37 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (300 MHz, CDCl3, ppm): δ 15.0 (bs, 1H), 8.46 (s, 1H), 7.65 (s, 1H), 6.84 (s, 1H), 4.26-4.23 (m, 2H), 3.94-3.90 (m, 4H), 3.63-3.61 (m, 2H), 3.39-3.35 (m, 4H), 3.11-3.06 (m, 1H), 2.19-2.11 (m, 2H), 1.86-1.82 (m, 1H), 0.96 (d, J=8.4 Hz, 3H), 0.86 (d, J=8.4 Hz, 3H).

Example 11: 1-hydroxy-6-isopropyl-10-methoxy-9-(3-methoxypropoxy)-2-oxo-6,7-dihydro-2H-pyrido[2,1-a]isoquinoline-3-carboxylic Acid

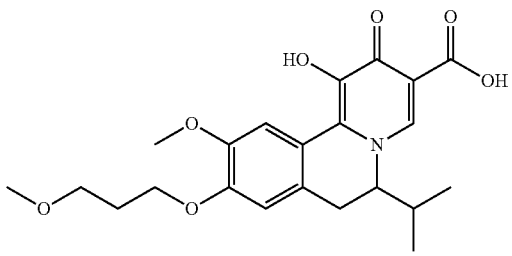 [SMILES: COCCCOc1cc2c(cc1OC)-c1c(O)c(=O)c(C(=O)O)cn1C(C(C)C)C2]

Into a 100-mL round-bottom flask, was placed a solution of ethyl 10-methoxy-9-(3-methoxypropoxy)-2-oxo-6-(propan-2-yl)-2H,6H,7H-pyrido[2,1-a]isoquinoline-3-carboxylate (900 mg, 2.10 mmol, 1.00 equiv) in acetic acid (20 mL). This was followed by the addition of F-TEDA-BF4 (4.5 g, 12.71 mmol, 6.00 equiv), in portions. The resulting solution was stirred for 72 h at 50° C. in an oil bath. The resulting mixture was concentrated under vacuum. The crude product was purified by Prep-HPLC with the following conditions (Waters XBridge): Column, RP18 19*150 mm, 5 μm; mobile phase, A: 0.05% NH₃.H₂O B: ACN; Detector, UV254 nm & 220 nm. This resulted in 100 mg (10%) of ethyl 1-acetoxy-6-isopropyl-10-methoxy-9-(3-methoxypropoxy)-2-oxo-6,7-dihydro-2H-pyrido[2,1-a]isoquinoline-3-carboxylate as a white solid. LC-MS (M+1): 488; RT=1.67 min. The measurements of the retention were done with a reversed phase column (C18). Shimadzu LCMS 2020; 50*3.0 Shim-pack XR-ODS, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min.

Into a 50-mL round-bottom flask, was placed a solution of ethyl 1-acetoxy-6-isopropyl-10-methoxy-9-(3-methoxypropoxy)-2-oxo-6,7-dihydro-2H-pyrido[2,1-a]isoquinoline-3-carboxylate (100 mg, 0.21 mmol, 1.00 equiv) in methanol/H₂O (2/0.2 mL). This was followed by the addition of sodium hydroxide (33 mg, 0.84 mmol, 4.00 equiv), in portions. The resulting solution was stirred for 2 h at 40° C. in an oil bath. The resulting mixture was concentrated under vacuum. The resulting solution was diluted with 3 mL of water. The pH value of the solution was adjusted to 6-5 with acetic acid (100%). The resulting solution was extracted with 3×10 mL of ethyl acetate and the organic layers combined. The organic layer was dried over anhydrous sodium sulfate and concentrated under vacuum. This resulted in 30 mg (33%) of 1-hydroxy-6-isopropyl-10-methoxy-9-(3-methoxypropoxy)-2-oxo-6,7-dihydro-2H-pyrido[2,1-a]isoquinoline-3-carboxylic acid as a white solid. LC-MS [M+1]: 420; RT=1.66 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-(DMSO, ppm): δ 10.23 (bs, 1H), 8.72 (s, 1H), 8.80 (s, 1H), 6.68 (s, 1H), 4.37-4.35 (m, 1H), 4.13-4.05 (m, 2H), 3.74 (s, 3H), 3.53-3.49 (m, 2H), 3.19 (s, 3H), 3.11-3.06 (m, 2H), 2.02-1.98 (m, 2H), 1.62-1.59 (m, 1H), 0.88 (d, J=8.4 Hz, 3H), 0.71 (d, J=8.4 Hz, 3H).

Example 12: (S)-10-chloro-1-fluoro-6-isopropyl-9-(3-methoxypropoxy)-2-oxo-6,7-dihydro-2H-pyrido[2,1-a]isoquinoline-3-carboxylic acid, and (R)-10-chloro-1-fluoro-6-isopropyl-9-(3-methoxypropoxy)-2-oxo-6,7-dihydro-2H-pyrido[2,1-a]isoquinoline-3-carboxylic Acid

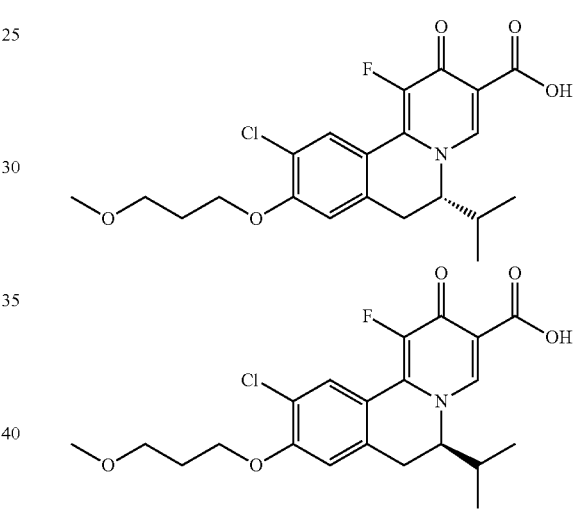

A mixture of 5-bromo-2-chloro-phenol (10.00 g, 48.20 mmol, 1.00 eq), 1-bromo-3-methoxy-propane (14.75 g, 96.41 mmol, 2.00 eq) and K₂CO₃ (19.99 g, 144.61 mmol, 3.00 eq) in acetone (100.00 mL) was stirred at 50° C. for 15 h. After filtration, the filtrate was concentrated under reduced pressure. The residue was purified by silica gel chromatography eluted with PE to PE:EA=5:1. 4-bromo-1-chloro-2-(3-methoxypropoxy)benzene (13.40 g, 47.93 mmol, 99.44% yield) was obtained as a colorless oil which was confirmed by LC-MS and used directly in the next step. LC-MS: EW5403-239-P1Z0 (M+H⁺=278.9, M+2+H⁺=280.9)

A mixture of 4-bromo-1-chloro-2-(3-methoxypropoxy)benzene (5.00 g, 17.89 mmol, 1.00 eq), 3-methylbutan-2-one (3.08 g, 35.77 mmol, 3.80 mL, 2.00 eq), Pd(dba)₂ (1.03 g, 1.79 mmol, 0.10 eq), Xantphos (2.07 g, 3.58 mmol, 0.20 eq) and t-BuONa (5.16 g, 53.67 mmol, 3.00 eq) in dioxane (100.00 mL) was stirred at 100° C. for 3 h. After filtration, the filtrate was concentrated under reduced pressure. Crude 1-[4-chloro-3-(3-methoxypropoxy)phenyl]-3-methyl-butan-2-one (7.10 g, crude) was obtained as a brown oil which was confirmed by LC-MS and used directly in the next step. LC-MS: EW5403-247-P1A2 (M+H⁺=285.2)

A mixture of crude 1-[4-chloro-3-(3-methoxypropoxy)phenyl]-3-methyl-butan-2-one (7.10 g, 24.93 mmol, 1.00 eq), $CH_3COONH_4$ (19.22 g, 249.32 mmol, 10.00 eq) and $NaBH_3CN$ (15.67 g, 249.32 mmol, 10.00 eq) in MeOH (300.00 mL) was stirred at 15° C. for 56 h. The mixture was extracted with DCM (100 mL*3), and the combined organic layers were concentrated under reduced pressure. The crude product was purified by reverse phase column with TFA as additive to give 1-[4-chloro-3-(3-methoxypropoxy)phenyl]-3-methylbutan-2-amine (3.00 g, 10.50 mmol, 42.10% yield) as a yellow oil which was confirmed by LC-MS (EW5403-249-P1A0). LC-MS: EW5403-249-P1A0 (M+H$^+$=286.1)

A mixture of 1-[4-chloro-3-(3-methoxypropoxy)phenyl]-3-methylbutan-2-amine (3.00 g, 10.50 mmol, 1.00 eq) and formic acid (3.87 g, 84.00 mmol, 3.17 mL, 8.00 eq) in dioxane (100.00 mL) was stirred at 100° C. for 48 h. After removal of the solvent, the residue was purified by silica gel chromatography eluted with PE to EA to afford N-[1-[[4-chloro-3-(3-methoxypropoxy)phenyl]methyl]-2-methyl-propyl]formamide (2.10 g, 6.69 mmol, 63.73% yield) as a light yellow solid which was confirmed by LC-MS. LC-MS: EW5403-257-P1A2 (M+H$^+$=314.1)

A mixture of N-(1-(4-chloro-3-(3-methoxypropoxy)phenyl)-3-methylbutan-2-yl)formamide (2.00 g, 6.37 mmol, 1.00 eq) and $POCl_3$ (2.93 g, 19.11 mmol, 1.78 mL, 3.00 eq) in MeCN (50.00 mL) was stirred at 60° C. for 1 h. After removal of the solvent, the crude was purified by silica gel chromatography eluted with PE to PE:EA=1:1 to give 7-chloro-3-isopropyl-6-(3-methoxypropoxy)-3,4-dihydroisoquinoline (1.3 g) as a black oil which was confirmed by LC-MS. LC-MS: EW5403-263-P1A3 (M+H$^+$=296.2)

A mixture of 7-chloro-3-isopropyl-6-(3-methoxypropoxy)-3,4-dihydroisoquinoline (510.00 mg, 1.72 mmol, 1.00 eq) and ethyl (2E)-2-(methoxymethylene)-3-oxo-butanoate (1.48 g, 8.62 mmol, 5.00 eq) in EtOH (10.00 mL) was stirred at 100° C. for 4 days. After removal of the solvent, the residue was purified by reverse phase column with $NH_4OH$ as additive to give ethyl 10-chloro-6-isopropyl-9-(3-methoxypropoxy)-2-oxo-2,6,7,1 b-tetrahydro-1H-pyrido[2,1-a]isoquinoline-3-carboxylate (140.00 mg, 279.40 μmol, 16.24% yield, 87% purity) as a yellow oil which was confirmed by LC-MS. LC-MS: EW5403-267-P1A1 (M+H$^+$=436.0)

To a solution of ethyl 10-chloro-6-isopropyl-9-(3-methoxypropoxy)-2-oxo-2,6,7,11b-tetrahydro-1H-pyrido[2,1-a]isoquinoline-3-carboxylate (150.00 mg, 344.08 μmol, 1.00 eq) in DME (20.00 mL), was added 2,3,5,6-tetrachloro-1,4-benzoquinone (169.21 mg, 688.17 μmol, 2.00 eq). The mixture was stirred at 70° C. for 5 h. The reaction mixture was concentrated in vacuo to give a residue. The residue was purified by flash column (DCM:MeOH=30:1). Compound ethyl 10-chloro-6-isopropyl-9-(3-methoxypropoxy)-2-oxo-6,7-dihydro-2H-pyrido[2,1-a]isoquinoline-3-carboxylate (50.24 mg, 115.78 μmol, 33.65% yield) was obtained as brown oil and confirmed by LC-MS. LC-MS: EW6108-43-P1A3 (M+H$^+$=434.1).

Into a 100-mL round-bottom flask, was placed a solution of ethyl 10-chloro-9-(3-methoxypropoxy)-2-oxo-6-(propan-2-yl)-2,6H,7H-pyrido[2,1-a]isoquinoline-3-carboxylate (1.5 g, 3.46 mmol, 1.00 equiv) in methanol (5 mL). The crude product was purified by Chiral-Prep-HPLC with the following conditions: Column, DAICEL CHIRALPAK IC 20*250 mm, 5 um; mobile phase, phase A:n-Hexane/DCM=5/1, phase B: Ethanol, A/B=50/50; Detector, 220 nm. This resulted in 580 mg (39%) of ethyl (S)-10-chloro-6-isopropyl-9-(3-methoxypropoxy)-2-oxo-6,7-dihydro-2H-pyrido[2,1-a]isoquinoline-3-carboxylate as a white solid. And 580 mg (39%) of ethyl (R)-10-chloro-6-isopropyl-9-(3-methoxypropoxy)-2-oxo-6,7-dihydro-2H-pyrido[2,1-a]isoquinoline-3-carboxylate as a white solid.

Into a 40-mL round-bottom flask, was placed a solution of ethyl (S)-10-chloro-6-isopropyl-9-(3-methoxypropoxy)-2-oxo-6,7-dihydro-2H-pyrido[2,1-a]isoquinoline-3-carboxylate (300 mg, 0.69 mmol, 1.00 equiv) in methanol/$H_2O$ (3/1 mL), sodium hydroxide (111 mg, 2.77 mmol, 4.00 equiv). The resulting solution was stirred for overnight at room temperature. The resulting solution was diluted with 40 mL of $H_2O$. The pH value of the solution was adjusted to 6 with AcOH. The solids were collected by filtration. This resulted in 200 mg (71%) of (S)-10-chloro-6-isopropyl-9-(3-methoxypropoxy)-2-oxo-6,7-dihydro-2H-pyrido[2,1-a]isoquinoline-3-carboxylic acid as a white solid. LC-MS-PH-PHNW-1-12-S-0: (ES, m/z): M+1=406, RT=1.46 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR-PH-PHNW-1-12-S-0: (CDCl3, 300 ppm): 8.48 (s, 1H), 7.75 (s, 1H), 7.04 (s, 1H), 6.83 (s, 1H), 4.27-4.20 (m, 2H), 3.90-3.88 (m, 1H), 3.63-3.56 (m, 2H), 3.48 (s, 4H), 3.18-3.09 (m, 1H), 2.18-2.10 (m, 2H), 1.93-1.91 (m, 1H), 0.96-0.80 (m, 6H).

Into a 40-mL round-bottom flask, was placed a solution of ethyl (R)-10-chloro-6-isopropyl-9-(3-methoxypropoxy)-2-oxo-6,7-dihydro-2H-pyrido[2,1-a]isoquinoline-3-carboxylate (300 mg, 0.69 mmol, 1.00 equiv) in methanol/$H_2O$ (3/1 mL), sodium hydroxide (111 mg, 2.77 mmol, 4.00 equiv). The resulting solution was stirred for 1 overnight at room temperature. The resulting solution was diluted with 40 mL of H2O. The pH value of the solution was adjusted to 6 with AcOH. This resulted in 200 mg (71%) of (R)-10-chloro-6-isopropyl-9-(3-methoxypropoxy)-2-oxo-6,7-dihydro-2H-pyrido[2,1-a]isoquinoline-3-carboxylic acid as a white solid (ES, m/z): M+1=406, RT=1.45 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient. H-NMR (CDCl3, 300 ppm): 8.48 (s, 1H), 7.75 (s, 1H), 7.04 (s, 1H), 6.83 (s, 1H), 4.27-4.20 (m, 2H), 3.90-3.88 (m, 1H), 3.63-3.56 (m, 2H), 3.48 (s, 4H), 3.18-3.09 (m, 1H), 2.18-2.10 (m, 2H), 1.93-1.91 (m, 1H), 0.96-0.80 (m, 6H).

Into a 40-mL round-bottom flask, was placed a solution of (S)-10-chloro-6-isopropyl-9-(3-methoxypropoxy)-2-oxo-6,7-dihydro-2H-pyrido[2,1-a]isoquinoline-3-carboxylic acid (385 mg, 0.95 mmol, 1.00 equiv) in $CH_3CN$/AcOH (20/2 mL), F-TEDA-$BF_4$ (1 g, 2.83 mmol, 3.00 equiv). The resulting solution was stirred for 48 h at 30° C. The reaction was then quenched by the addition of 100 mL of water. The solid was collected by filtration. This resulted in 400 mg (crude) of (S)-10-chloro-1-fluoro-6-isopropyl-9-(3-methoxypropoxy)-2-oxo-6,7-dihydro-2H-pyrido[2,1-a]isoquinoline-3-carboxylic acid as a white solid.

Into a 25-mL 3-necked round-bottom flask, was placed a solution of (S)-10-chloro-1-fluoro-6-isopropyl-9-(3-methoxypropoxy)-2-oxo-6,7-dihydro-2H-pyrido[2,1-a]isoquinoline-3-carboxylic acid (400 mg, 0.94 mmol, 1.00 equiv) in methanol/DCM (4/2 mL). This was followed by the addition of TMS-$CHN_2$ (2M) (2.8 mL, 6.00 equiv) dropwise with stirring. The resulting solution was stirred for 5 h at room temperature. The reaction was then quenched by the addition of 5 mL of water. The resulting solution was extracted with 3×20 mL of dichloromethane. The organic layers were combined, dried over anhydrous sodium sulfate and concentrated under vacuum. The crude product was purified by Prep-HPLC with the following conditions (Prep-HPLC-007): Column, SunFire Prep C18 OBD Column, 19*150 mm 5 um 10 nm; mobile phase, Water (0.1% FA) and ACN (48.0% ACN up to 53.0% in 7 min, hold 95.0% in 1 min, down to 48.0% in 1 min, hold 48.0% in 1 min); Detector, UV 220 nm. This resulted in 125 mg (30% for two steps) of methyl (S)-10-chloro-1-fluoro-6-isopropyl-9-(3-methoxypropoxy)-2-oxo-6,7-dihydro-2H-pyrido[2,1-a]isoquinoline-3-carboxylate as a white solid. LC-MS: (ES, m/z): M+1=438, R, T=1.03 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 2 minutes; Oven temperature 40° C.; flow: 1.5 mL/min.

Into a 8-mL round-bottom flask, was placed a solution of methyl (S)-10-chloro-1-fluoro-6-isopropyl-9-(3-methoxypropoxy)-2-oxo-6,7-dihydro-2H-pyrido[2,1-a]isoquinoline-3-carboxylate (35 mg, 0.08 mmol, 1.00 equiv) in methanol/H$_2$O (1/0.5 mL), sodium hydroxide (12.8 mg, 0.32 mmol, 4.00 equiv). The resulting solution was stirred for overnight at room temperature. The pH value of the solution was adjusted to 6 with AcOH (1M). The solid was collected by filtration. This resulted in 23.3 mg (68.8%) of (S)-10-chloro-1-fluoro-6-isopropyl-9-(3-methoxypropoxy)-2-oxo-6,7-dihydro-2H-pyrido[2,1-a]isoquinoline-3-carboxylic acid as a white solid. LC-MS– (ES, m/z): M+1=424, R, T=2.58 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (300 MHz, CDCl3, ppm): 8.48 (s, 1H), 8.15 (s, 1H), 6.80 (s, 1H), 4.28-4.21 (m, 2H), 3.91-3.84 (m, 1H), 3.75-3.62 (m, 2H), 3.48-3.37 (m, 4H), 3.19-3.09 (m, 1H), 2.15-2.01 (m, 2H), 1.51-1.35 (m, 2H), 0.94-0.75 (m, 6H).

Into a 40-mL round-bottom flask, was placed a solution of (R)-10-chloro-6-isopropyl-9-(3-methoxypropoxy)-2-oxo-6,7-dihydro-2H-pyrido[2,1-a]isoquinoline-3-carboxylic acid (385 mg, 0.95 mmol, 1.00 equiv) in CH$_3$CN/AcOH (20/2 mL), F-TEDA-BF$_4$ (1 g, 2.83 mmol, 3.00 equiv). The resulting solution was stirred for 48 h at 30° C. The reaction was then quenched by the addition of 100 mL of water. The solid was collected by filtration. This resulted in 400 mg (crude) of (R)-10-chloro-1-fluoro-6-isopropyl-9-(3-methoxypropoxy)-2-oxo-6,7-dihydro-2H-pyrido[2,1-a]isoquinoline-3-carboxylic acid as a white solid.

Into a 25-mL 3-necked round-bottom flask, was placed a solution of (R)-10-chloro-1-fluoro-6-isopropyl-9-(3-methoxypropoxy)-2-oxo-6,7-dihydro-2H-pyrido[2,1-a]isoquinoline-3-carboxylic acid (400 mg, 0.94 mmol, 1.00 equiv) in methanol/DCM (4/2 mL). This was followed by the addition of TMS-CHN$_2$ (2M) (2.8 mL, 6.00 equiv) dropwise with stirring. The resulting solution was stirred for 5 h at room temperature. The reaction was then quenched by the addition of 5 mL of water. The resulting solution was extracted with 3×20 mL of dichloromethane. The organic layers were combined, dried over anhydrous sodium sulfate and concentrated under vacuum. The crude product was purified by Prep-HPLC with the following conditions (Prep-HPLC-007): Column, SunFire Prep C18 OBD Column, 19*150 mm 5 um 10 nm; mobile phase, Water (0.1% FA) and ACN (48.0% ACN up to 53.0% in 7 min, hold 95.0% in 1 min, down to 48.0% in 1 min, hold 48.0% in 1 min); Detector, UV 220 nm. This resulted in 125 mg (30% for two steps) of methyl (R)-10-chloro-1-fluoro-6-isopropyl-9-(3-methoxypropoxy)-2-oxo-6,7-dihydro-2H-pyrido[2,1-a]isoquinoline-3-carboxylate as a white solid. LC-MS: (ES, m/z): M+1=438, R, T=1.03 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 2 minutes; Oven temperature 40° C.; flow: 1.5 mL/min.

Into a 8-mL round-bottom flask, was placed a solution of methyl (R)-10-chloro-1-fluoro-6-isopropyl-9-(3-methoxypropoxy)-2-oxo-6,7-dihydro-2H-pyrido[2,1-a]isoquinoline-3-carboxylate (35 mg, 0.08 mmol, 1.00 equiv) in methanol/H$_2$O (1/0.5 mL), sodium hydroxide (12.8 mg, 0.32 mmol, 4.00 equiv). The resulting solution was stirred for overnight at room temperature. The pH value of the solution was adjusted to 6 with AcOH (1M). The solid was collected by filtration. This resulted in 23.3 mg (68.8%) of (R)-10-chloro-1-fluoro-6-isopropyl-9-(3-methoxypropoxy)-2-oxo-6,7-dihydro-2H-pyrido[2,1-a]isoquinoline-3-carboxylic acid as a white solid. LC-MS– (ES, m/z): M+1=424, R, T=2.58 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.5 minutes; Oven temperature 40° C.; flow: 1.5 mL/min. H-NMR: (300 MHz, CDCl3, ppm): 8.48 (s, 1H), 8.15 (s, 1H), 6.80 (s, 1H), 4.28-4.21 (m, 2H), 3.91-3.84 (m, 1H), 3.75-3.62 (m, 2H), 3.48-3.37 (m, 4H), 3.19-3.09 (m, 1H), 2.15-2.01 (m, 2H), 1.51-1.35 (m, 2H), 0.94-0.75 (m, 6H).

Example 13: (S)-6-(tert-butyl)-1-fluoro-10-methoxy-9-(3-methoxypropoxy)-2-oxo-6,7-dihydro-2H-pyrido[2,1-a]isoquinoline-3-carboxylic acid, and (R)-6-(tert-butyl)-1-fluoro-10-methoxy-9-(3-methoxypropoxy)-2-oxo-6,7-dihydro-2H-pyrido[2,1-a]isoquinoline-3-carboxylic Acid

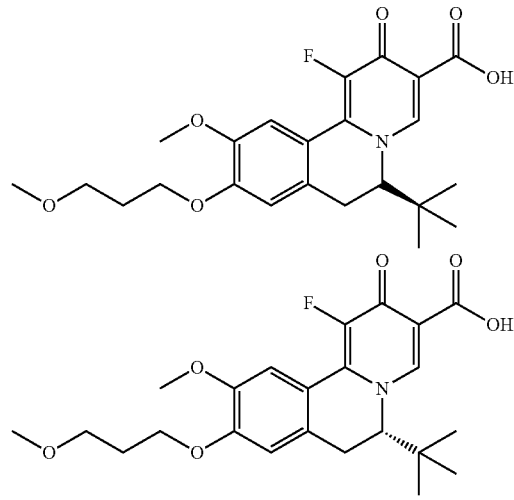

Into a 50-mL round-bottom flask, was placed methanol (25 mL), borane sodium (1.9 g, 51.60 mmol, 1.00 equiv). The resulting solution was stirred for 14 h at room temperature. The resulting mixture was concentrated under vacuum. The resulting mixture was washed with 2×15 mL of ether. This resulted in 5 g NaB(OCH$_3$)$_4$ (61%) of as a white solid. H-NMR: (300 MHz, CD$_3$OD, ppm): δ·3.34 (s, 12H).

Into a 50-mL round-bottom flask purged and maintained with an inert atmosphere of nitrogen, was placed methyl 6-tert-butyl-10-chloro-1-fluoro-9-(3-methoxypropoxy)-2-oxo-2H,6H,7H-pyrido[2,1-a]isoquinoline-3-carboxylate (400 mg, 0.89 mmol, 1.00 equiv), NaB(OCH$_3$)$_4$ (420 mg, 2.66 mmol, 3.00 equiv), Pd$_2$(dba)$_3$ (81.1 mg, 0.09 mmol, 0.10 equiv), t-Buxphos (75 mg, 0.18 mmol, 0.20 equiv), N,N-dimethylformamide (10 mL). The resulting solution was stirred for 1 h at 80° C. in an oil bath. The resulting solution was diluted with 50 mL of H$_2$O. The resulting solution was extracted with 3×15 mL of ethyl acetate and the organic layers combined. The resulting mixture was washed with 1×10 mL of water and 1×10 mL of brine. The resulting mixture was dried by Na$_2$SO$_4$ and filtrated, filtrate concentrated under vacuum. The residue was applied onto a silica gel column with dichloromethane/methanol (10:1). This resulted in 180 mg (45%) of methyl 6-(tert-butyl)-1-fluoro-10-methoxy-9-(3-methoxypropoxy)-2-oxo-6,7-dihydro-2H-pyrido[2,1-a]isoquinoline-3-carboxylate as a light brown solid. LC-MS (M+1): 448; RT=1.35 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.5 mL/min.:

The methyl 6-(tert-butyl)-1-fluoro-10-methoxy-9-(3-methoxypropoxy)-2-oxo-6,7-dihydro-2H-pyrido[2,1-a]isoquinoline-3-carboxylate (100 mg) was purified by Chiral-Prep-HPLC with the following conditions (Chiral-A (IC) 001IC00CE-LC020): Column, Chiralpak IC4.6*250 mm, 5 um; mobile phase, methanol:EtOH=1:1; Detector, 254 nm. This resulted in 40 mg (40%) of methyl (S)-6-(tert-butyl)-1-fluoro-10-methoxy-9-(3-methoxypropoxy)-2-oxo-6,7-dihydro-2H-pyrido[2,1-a]isoquinoline-3-carboxylate as a white solid. and 50 mg (50%) of methyl (R)-6-(tert-butyl)-1-fluoro-10-methoxy-9-(3-methoxypropoxy)-2-oxo-6,7-dihydro-2H-pyrido[2,1-a]isoquinoline-3-carboxylate as a white solid.

Into a 8-mL vial, was placed methyl (S)-6-(tert-butyl)-1-fluoro-10-methoxy-9-(3-methoxypropoxy)-2-oxo-6,7-dihydro-2H-pyrido[2,1-a]isoquinoline-3-carboxylate (40 mg, 0.09 mmol, 1.00 equiv), methanol (1 mL, 2.00 equiv), water (0.2 mL, 3.00 equiv), sodium hydroxide (14 mg, 0.35 mmol, 4.00 equiv). The resulting solution was stirred for 14 h at room temperature. The resulting mixture was concentrated under vacuum. The pH value of the solution was adjusted to 6 with acetic acid. The solids were collected by filtration. This resulted in 16.4 mg (42%) of (S)-6-(tert-butyl)-1-fluoro-10-methoxy-9-(3-methoxypropoxy)-2-oxo-6,7-dihydro-2H-pyrido[2,1-a]isoquinoline-3-carboxylic acid as a white solid. LC-MS [M+1]: 434; RT=1.41 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 3.0 minutes; Oven temperature 40° C.; flow: 1.5 mL/min. H-NMR-PH-PHNW-1-11-S-0: (300 MHz, CDCl$_3$, ppm): δ 8.43 (s, 1H), 7.60 (s, 1H), 6.79 (s, 1H), 4.30-4.12 (m, 2H), 4.11-3.98 (m, 1H), 3.91 (s, 3H), 3.67-3.52 (m, 2H), 3.50-3.30 (m, 4H), 3.17 (d, J=16.8 Hz, 1H), 2.22-2.10 (m, 2H), 081 (s, 9H).

Into a 8-mL vial, was placed methyl (R)-6-(tert-butyl)-1-fluoro-10-methoxy-9-(3-methoxypropoxy)-2-oxo-6,7-dihydro-2H-pyrido[2,1-a]isoquinoline-3-carboxylate (50 mg, 0.11 mmol, 1.00 equiv), methanol (1 mL), water (0.2 mL), sodium hydroxide (17.8 mg, 0.45 mmol, 4.00 equiv). The resulting solution was stirred for 14 h at room temperature. The resulting mixture was concentrated under vacuum. The pH value of the solution was adjusted to 6 with acetic acid. The solids were collected by filtration. This resulted in 22.2 mg (46%) of (R)-6-(tert-butyl)-1-fluoro-10-methoxy-9-(3-methoxypropoxy)-2-oxo-6,7-dihydro-2H-pyrido[2,1-a]isoquinoline-3-carboxylic acid as a white solid. LC-MS (M+1): 434; RT=2.26 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 5.0 minutes; Oven temperature 40° C.; flow: 1.5 mL/min. H-NMR: (300 MHz, CDCl$_3$, ppm): δ 8.43 (s, 1H), 7.60 (s, 1H), 6.79 (s, 1H), 4.30-4.12 (m, 2H), 4.11-3.98 (m, 1H), 3.91 (s, 3H), 3.67-3.52 (m, 2H), 3.50-3.30 (m, 4H), 3.17 (d, J=17.1 Hz, 1H), 2.22-2.10 (m, 2H), 081 (s, 9H).

Example 14: (S)-6-(tert-butyl)-1-fluoro-10-(methoxy-d3)-9-(3-methoxypropoxy)-2-oxo-6,7-dihydro-2H-pyrido[2,1-a]isoquinoline-3-carboxylic Acid

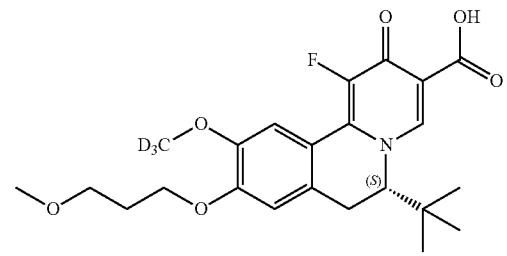

Into a 50-mL round-bottom flask, was placed borane sodium (1.15 g, 31.23 mmol, 1.00 equiv), CD$_3$OD (15 mL). The resulting solution was stirred for 14 h at room temperature. The resulting mixture was concentrated under vacuum. The resulting solution was diluted with 20 mL of ether. The solids were collected by filtration. This resulted in 3.5 g (66%) of NaB(OCD$_3$)$_4$ as a white solid. B-NMR (300 MHz, CD$_3$OD, ppm): δ.2.99 (s, 1 B).

Into a 50-mL round-bottom flask purged and maintained with an inert atmosphere of nitrogen, was placed methyl methyl (S)-6-(tert-butyl)-10-chloro-1-fluoro-9-(3-methoxypropoxy)-2-oxo-6,7-dihydro-2H-pyrido[2,1-a]isoquinoline-3-carboxylate (100 mg, 0.22 mmol, 1.00 equiv), NaB (OCD$_3$)$_4$ (150.7 mg, 0.89 mmol, 4.00 equiv), DMA (5 mL), Pd$_2$(dba)$_3$ (20.2 mg, 0.02 mmol, 0.10 equiv), t-Buxphos (18.8 mg, 0.04 mmol, 0.20 equiv). The resulting solution was stirred for 5 h at 110° C. in an oil bath. The reaction mixture was cooled to room temperature. The resulting solution was diluted with 50 mL of H$_2$O. The resulting solution was extracted with 3×15 mL of ethyl acetate and the organic layers combined. The resulting mixture was washed with 1×15 mL of water and 1×15 mL of brine. Combined organic phase and dried by Na$_2$SO$_4$, filtrated, concentrated. The residue was applied onto a silica gel column with dichloromethane/methanol (10:1) to give crude product, the crude product was purified by Prep-HPLC with the following conditions (Waters 2767): Column, SunFire Prep C18 OBD, 19×150 mm, 5 um; mobile phase, Mobile Phase A: Water/0.05% TFA, Mobile Phase B: ACN; (34% up to 51% in 6 min, 6 min, 20 ml/min; Detector, 220 nm. This resulted in 20 mg (20%) of methyl-d3 (S)-6-(tert-butyl)-1-fluoro-10-(methoxy-d3)-9-(3-methoxypropoxy)-2-oxo-6,7-dihydro-2H-pyrido[2,1-a]isoquinoline-3-carboxylate as a light yellow solid. LC-MS-PH-PHNW-1-14-S-2: (ES, m/z): LC-MS (M+1): 454; RT=1.38 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 2.6 minutes; Oven temperature 40° C.; flow: 1.5 mL/min.

Into a 8-mL round-bottom flask, was placed methyl-d3 (S)-6-(tert-butyl)-1-fluoro-10-(methoxy-d3)-9-(3-methoxypropoxy)-2-oxo-6,7-dihydro-2H-pyrido[2,1-a]isoquinoline-3-carboxylate (20 mg, 0.04 mmol, 1.00 equiv), methanol (1 mL), water (0.2 mL), sodium hydroxide (7 mg, 0.17 mmol, 4.00 equiv). The resulting solution was stirred for 14 h at room temperature. The resulting mixture was concentrated under vacuum. The pH value of the solution was adjusted to 6 with acetic acid. The solids were collected by filtration. This resulted in 6.4 mg (33%) of (S)-6-(tert-butyl)-1-fluoro-10-(methoxy-d3)-9-(3-methoxypropoxy)-2-oxo-6,7-dihydro-2H-pyrido[2,1-a]isoquinoline-3-carboxylic acid as a white solid. LC-MS (M+1): 437; RT=3.01 min. The measurements of the retention were done with a reversed phase column (C18). Shimadzu LCMS 2020; 50*3.0 Kinetex 2.6 u XB-C18, 2.6 microm; Eluent A: water (0.05% TFA); Eluent B: Acetonitrile; linear gradient from 5% acetonitrile to 100% acetonitrile in 7.0 minutes; Oven temperature 40° C.; flow: 1.5 mL/min. H-NMR: (300 MHz, CDCl$_3$, ppm): δ 8.3 (s, 1H), 7.60 (s, 1H), 6.79 (s, 1H), 4.28-4.11 (m, 2H), 4.10-3.96 (m, 1H), 3.65-3.50 (m, 2H), 3.50-3.28 (m, 4H), 3.17 (d, J=13.5 Hz, 1H), 2.20-2.10 (m, 2H), 081 (s, 9H).

Example 15: (S)-1-fluoro-6-isopropyl-10-(methoxy-d3)-9-(3-methoxypropoxy)-2-oxo-6,7-dihydro-2H-pyrido[2,1-a]isoquinoline-3-carboxylic Acid

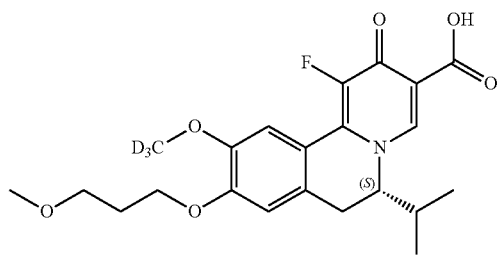

Into a 25-mL round-bottom flask purged and maintained with an inert atmosphere of nitrogen, was placed methyl (6S)-10-chloro-1-fluoro-9-(3-methoxypropoxy)-2-oxo-6-(propan-2-yl)-2H,6H,7H-pyrido[2,1-a]isoquinoline-3-carboxylate (100 mg, 0.23 mmol, 1.00 equiv), DMF (3 mL), Pd$_2$(dba)$_3$ (20 mg, 0.02 mmol, 0.10 equiv), t-Buxphos (19 mg, 0.04 mmol, 0.20 equiv), NaB(OCD$_3$)$_4$ (194 mg, 1.14 mmol, 5.00 equiv). The resulting solution was stirred for 1 h at 100° C. in an oil bath. The reaction mixture was cooled to room temperature. The resulting solution was diluted with 15 mL of H$_2$O. The resulting solution was extracted with 3×10 mL of ethyl acetate and the organic layers combined. The resulting mixture was washed with 1×10 mL of water and 1×10 mL of brine. The residue was purified by Prep-TLC with dichloromethane/methanol (10:1) twice. This resulted in a mixture (25 mg) of ($^2$H$_3$)methyl (6S)-1-fluoro-10-($^2$H$_3$)methoxy-9-(3-methoxypropoxy)-2-oxo-6-(propan-2-yl)-2H,6H,7H-pyrido[2,1-a]isoquinoline-3-carboxylate and ($^2$H$_3$)methyl (6S)-1,10-bis($^2$H$_3$)methoxy-9-(3-methoxypropoxy)-2-oxo-6-(propan-2-yl)-2H,6H,7H-pyrido[2,1-a]isoquinoline-3-carboxylate as a brown solid. LC-MS-PH-PHNW-1-15-S-1: (ES, m/z): LC-MS (M+1): 440; RT=2.26 min. LC-MS-PH-PHNW-1-15-S-1BP: (ES, m/z): LC-MS (M+1): 455; RT=2.24 min. The measurements of the retention were done with a reversed phase column (C18). Shimadzu LCMS 2020; 50*3.0 Kinetex 2.6 u XR-ODS 0.6 microm; Eluent A: water (0.05% TFA); Eluent B: Acetonitrile; linear gradient from 5% acetonitrile to 100% acetonitrile in 5.0 minutes; Oven temperature 40° C.; flow: 1.5 mL/min.

Into a 8-mL round-bottom flask, was placed the mixture of ($^2$H$_3$)methyl (6S)-1-fluoro-10-($^2$H$_3$)methoxy-9-(3-methoxypropoxy)-2-oxo-6-(propan-2-yl)-2H,6H,7H-pyrido[2,1-a]isoquinoline-3-carboxylate and ($^2$H$_3$)methyl (6S)-1,10-bis($^2$H$_3$)methoxy-9-(3-methoxypropoxy)-2-oxo-6-(propan-2-yl)-2H,6H,7H-pyrido[2,1-a]isoquinoline-3-carboxylate (25 mg), sodium hydroxide (11 mg), MeOH (1 mL) and water (0.2 mL). The resulting solution was stirred for 3 h at room temperature. The pH value of the solution was adjusted to 6 with acetic acid. The resulting mixture was concentrated under vacuum. The resulting crude product was purified by Prep-HPLC with the following conditions (Prep-HPLC-013): Column, SunFire Prep C18 OBD Column, 19×150 mm 5 um 10 nm; mobile phase, Water (0.05% TFA) and ACN (41.0% ACN up to 46.0% in 6 min); Detector, UV 220 nm. This resulted in 4.3 mg of (6S)-1-fluoro-10-($^2$H$_3$)methoxy-9-(3-methoxypropoxy)-2-oxo-6-(propan-2-yl)-2H,6H,7H-pyrido[2,1-a]isoquinoline-3-carboxylic acid as a brown solid. LC-MS-PH-PHNW-1-15-S-0: (ES, m/z): LC-MS (M+1): 423; RT=0.97 min. The measurements of the retention were done with a reversed phase column (C18). Shimadzu LCMS 2020; 50*3.0 Kinetex 2.6 u XR-ODS 0.6 microm; Eluent A: water (0.05% ammonia water); Eluent B: Acetonitrile; linear gradient from 5% acetonitrile to 100% acetonitrile in 3.5 minutes; Oven temperature 40° C.; flow: 1.0 mL/min. H-NMR: (300 MHz, CD$_3$OD, ppm): δ 8.70 (s, 1H), 7.68 (s, 1H), 7.09 (s, 1H), 4.39-4.10 (m, 3H), 3.70-3.60 (m, 2H), 3.64 (s, 3H), 3.29-3.21 (m, 1H), 2.18-2.08 (m, 2H), 1.80-1.60 (m, 1H), 1.05-0.90 (m, 3H), 0.90-0.78 (m, 3H).

Example 16: (S)-6-isopropyl-1,10-bis(methoxy-d3)-9-(3-methoxypropoxy)-2-oxo-6,7-dihydro-2H-pyrido[2,1-a]isoquinoline-3-carboxylic Acid

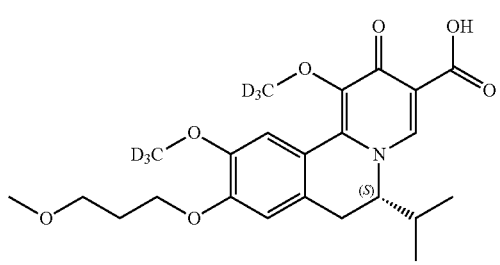

Into a 8-mL round-bottom flask, was placed the mixture of ($^2$H$_3$)methyl (6S)-1-fluoro-10-($^2$H$_3$)methoxy-9-(3-methoxypropoxy)-2-oxo-6-(propan-2-yl)-2H,6H,7H-pyrido[2,1-a]isoquinoline-3-carboxylate and ($^2$H$_3$)methyl (6S)-1,10-bis($^2$H$_3$)methoxy-9-(3-methoxypropoxy)-2-oxo-6-(propan-2-yl)-2H,6H,7H-pyrido[2,1-a]isoquinoline-3-carboxylate (25 mg), sodium hydroxide (11 mg, 0.28 mmol), MeOH (1 mL) and water (0.2 mL). The resulting solution was stirred for 3 h at room temperature. The pH value of the solution was adjusted to 6 with acetic acid. The resulting mixture was concentrated under vacuum. The resulting crude product was purified by Prep-HPLC with the following conditions (Prep-HPLC-013): Column, SunFire Prep C18 OBD Column, 19×150 mm 5 um 10 nm; mobile phase, Water (0.05% TFA) and ACN (41.0% ACN up to 46.0% in 6 min); Detector, UV 220 nm. (6S)-1,10-bis($^2$H$_3$)methoxy-9-(3-methoxypropoxy)-2-oxo-6-(propan-2-yl)-2H,6H,7H-pyrido[2,1-a]isoquinoline-3-carboxylic acid as a brown solid. LC-MS-PH-PHNW-1-15-S-0: (ES, m/z): LC-MS (M+1): 438; RT=1.01 min. The measurements of the retention were done with a reversed phase column (C18). Shimadzu LCMS 2020; 50*3.0 Kinetex 2.6 u XR-ODS 0.6 microm; Eluent A: water (0.05% ammonia water); Eluent B: Acetonitrile; linear gradient from 5% acetonitrile to 100% acetonitrile in 3.5 minutes; Oven temperature 40° C.; flow: 1.0 mL/min. H-NMR: (300 MHz, CD$_3$OD, ppm): δ 8.63 (s, 1H), 8.10 (s, 1H), 7.04 (s, 1H), 4.30-4.12 (m, 2H), 3.70-3.60 (m, 2H), 3.38 (s, 3H), 3.29-3.11 (m, 1H), 2.18-2.05 (m, 2H), 1.80-1.60 (m, 1H), 1.01-0.90 (m, 3H), 0.90-0.78 (m, 3H).

Example A

The compounds below are prepared by methods substantially identical, similar, or analogous to those disclosed in Scheme A-E, Scheme I-V, and above examples

| Example | Structure | m/z (MH$^+$) |
| --- | --- | --- |
| A-1 | 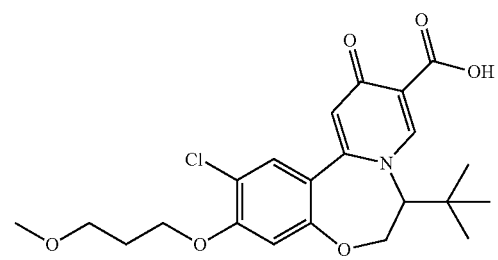 [SMILES: COCCCOc1cc2c(cc1Cl)-c1cc(=O)c(C(=O)O)cn1C(C(C)(C)C)CO2] | 436 |
| A-2 | 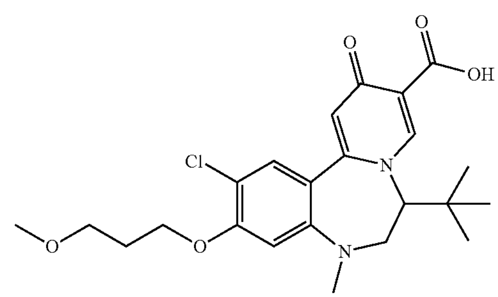 [SMILES: COCCCOc1cc2c(cc1Cl)-c1cc(=O)c(C(=O)O)cn1C(C(C)(C)C)CN2C] | 449 |
| A-3 | 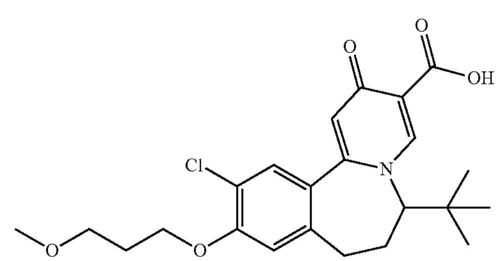 [SMILES: COCCCOc1cc2c(cc1Cl)-c1cc(=O)c(C(=O)O)cn1C(C(C)(C)C)CC2] | 434 |
| A-4 | 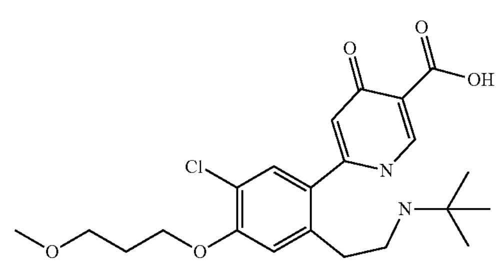 [SMILES: COCCCOc1cc(CCNC(C)(C)C)c(-c2cc(=O)c(C(=O)O)c[nH]2)cc1Cl] | 435 |

| Example | Structure | m/z (MH+) |
|---|---|---|
| A-8 | 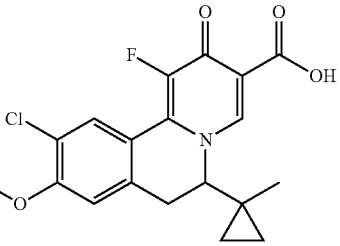 | 436 |
| A-9 | 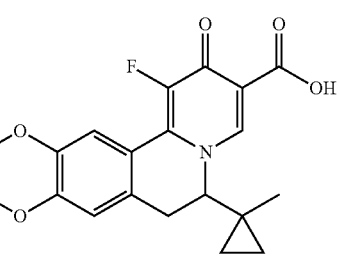 | 432 |
Example B
The compounds below are prepared by methods substantially identical, similar, or analogous to those disclosed in Scheme A-E, Scheme I-V, and above examples
| Example | Structure | m/z (MH+) |
|---|---|---|
| B-1 | 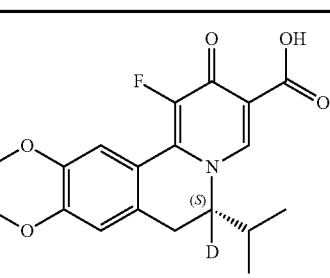 | 421 |
| B-3 | 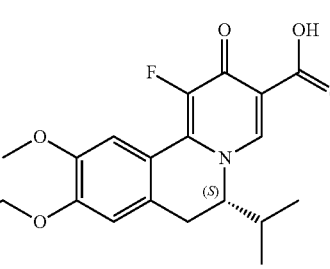 | 423 |
| B-4 | 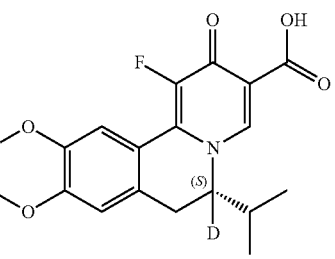 | 424 |

| Example | Structure | m/z (MH+) |
|---------|-----------|-----------|
| B-5 | 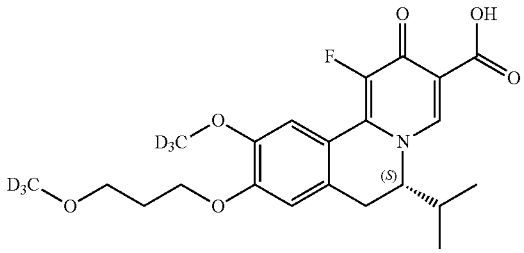 | 426 |
| B-6 | 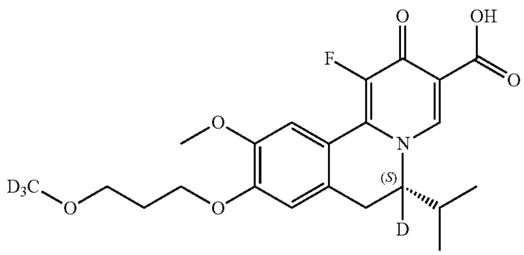 | 424 |
| B-7 | 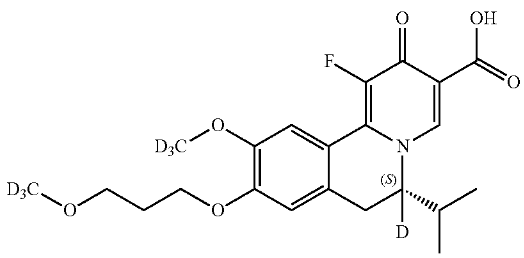 | 427 |
| B-8 | 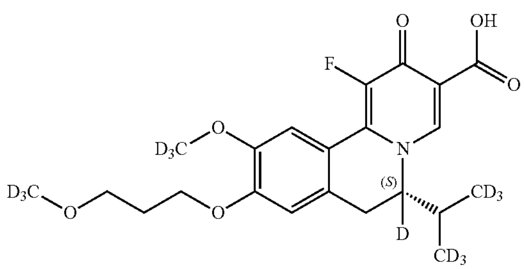 | 433 |

Example C

The compounds below are prepared by methods substantially identical, similar, or analogous to those disclosed in Scheme A-E, Scheme I-V, and above examples

| Example | Structure | m/z (MH+) |
|---------|-----------|-----------|
| C-1 | 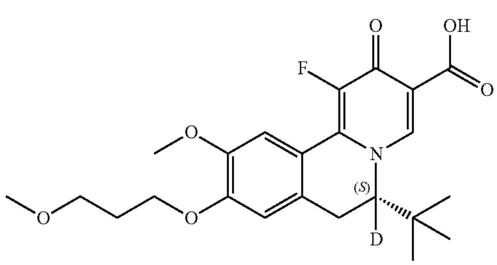 | 435 |

-continued

| Example | Structure | m/z (MH+) |
|---|---|---|
| C-3 | 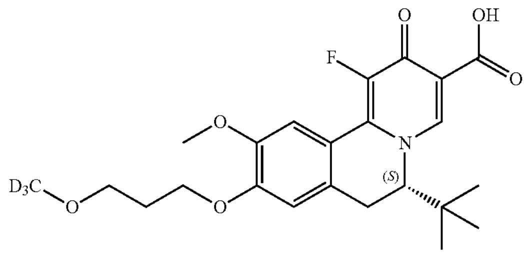 | 437 |
| C-4 | 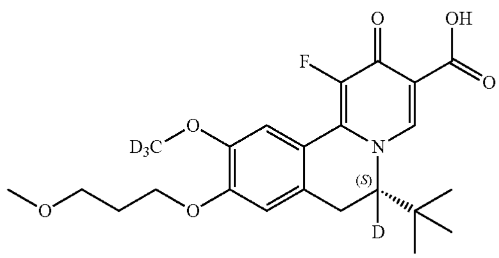 | 438 |
| C-5 | 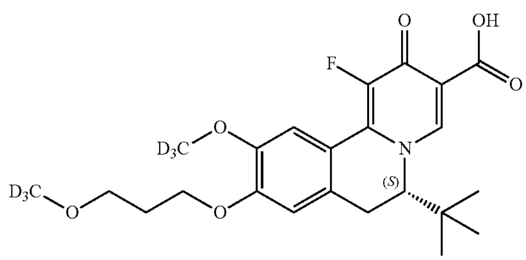 | 440 |
| C-6 | 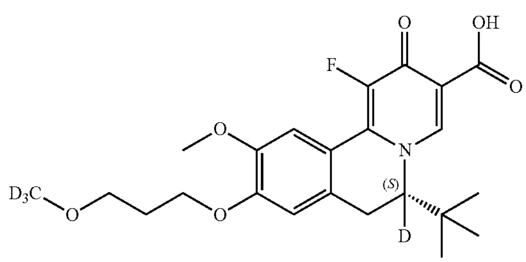 | 438 |
| C-7 | | 441 |
| C-7 | | 450 |

-continued

| Example | Structure | m/z (MH+) |
|---|---|---|
| C-8 | (structure) | 446 |

Example D

The compounds below are prepared by methods substantially identical, similar, or analogous to those disclosed in Scheme A-E, Scheme I-V, and above examples

| Example | Structure | m/z (MH+) |
|---|---|---|
| D-1 | (structure) | 425 |
| D-2 | (structure) | 427 |
| D-3 | (structure) | 428 |
| D-4 | (structure) | 434 |

Example E

The compounds below are prepared by methods substantially identical, similar, or analogous to those disclosed in Scheme A-E, Scheme I-V, and above examples

| Example | Structure | m/z (MH+) |
|---|---|---|
| E-1 | 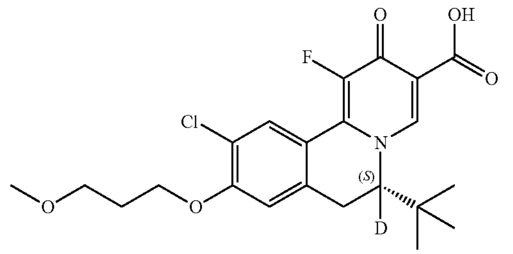 | 439 |
| E-2 | 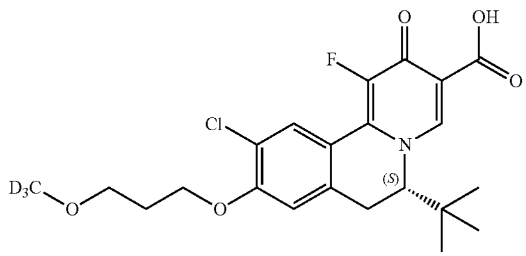 | 441 |
| E-3 | 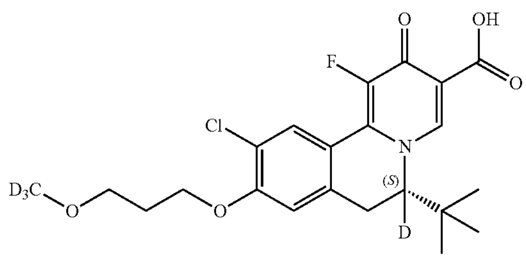 | 442 |
| E-4 | 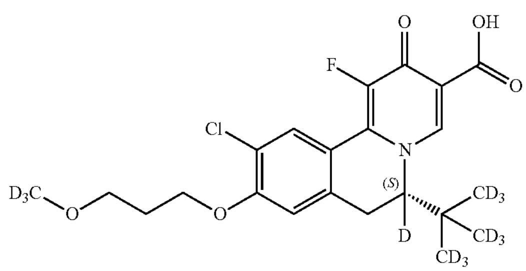 | 451 |
| E-5 | 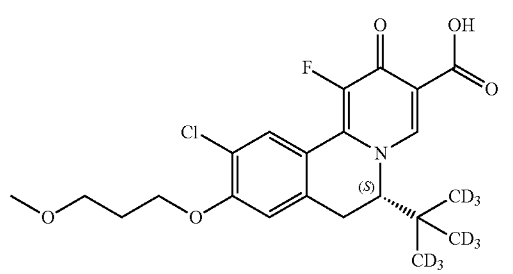 | 447 |

Biological Example 1: HBsAg Assay

HepG2.2.15 cells (Acs et al. Proc Natl Acad Sci USA, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% CO2 at 37° C. HepG2.2.15 cells were seeded in duplicate into white, 96-well plates at 1.5×10⁴ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL03 1 0-2) was used to measure the levels of secreted HBV antigens semi-quantitatively. For the detection 50

µL/well culture supernatant was used and HBsAg was quantified using HBsAg chemiluminescence immunoassay (CLIA) kit (Autobio Diagnostics Co., Zhengzhou, China, Catalog number: CL0310-2), 50 µL of the supernatant was transferred to the CLIA assay plate and 50 uL of enzyme conjugate reagent was added into each well. The plates were sealed and gently agitated for 1 hour at room temperature. The supernatant-enzyme-mixture was discarded and wells were washed 6 times with 300 µL of PBS. The residual liquid was removed by plating the CLIA plate right side down on absorbent tissue paper. 25 µL of substrates A and B were added to each well. Luminance was measured using a lmninometer (Mithras LB 940 Multimode Microplate Reader) after 10 minutes incubation. Dose-response curves were generated and the IC50 value was extrapolated by using the E-WorkBook Suite (ID Business Solutions Ltd., Guildford, UK). The IC50 was defined as the compound concentration (or conditioned media log dilution) at which HBsAg secretion was reduced by 50% compared to the no drug control. The compounds of the present invention were tested for their capacity to inhibit HBsAg as described herein.

Biological Example 2: HBV DNA Assay

The assay employs real-time qPCR (TaqMan) to directly measure extracellular HBV DNA copy number. HepG2.2.15 cells were plated in 96-well microtiter plates. Only the interior wells were utilized to reduce "edge effects" observed during cell culture, the exterior wells were filled with complete medium to help minimize sample evaporation. On the following day, the HepG2.2.15 cells were washed and the medium was replaced with complete medium containing various concentrations of a test compound in triplicate. 3TC was used as the positive control, while media alone was added to cells as a negative control (virus control, VC). Three days later, the culture medium was replaced with fresh medium containing the appropriately diluted drug. Six days following the initial administration of the test compound, the cell culture supernatant was collected, treated with pronase and then used in a real-time qPCR/TaqMan assay to determine HBV DNA copy numbers. TDF (tenofovir disoproxil fumarate) is used as a positive control reference. Antiviral activity was calculated from the reduction in HBV DNA levels (IC50). The results, as shown in the Table below, show that the Example 2A are highly potent anti-HBV agent.

| | Structure | $EC_{50}$ |
|---|---|---|
| Example 2A | 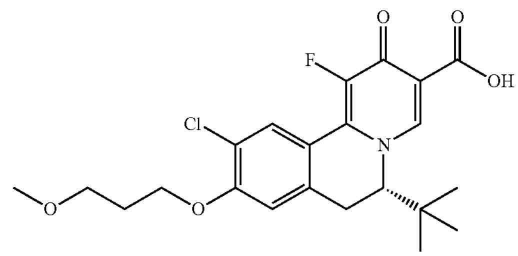 [SMILES: COCCCOc1cc2c(cc1Cl)-c1c(F)c(=O)c(C(=O)O)cn1[C@H](C(C)(C)C)C2] | <1 nM |
| Compound 203 in WO2015113990 | 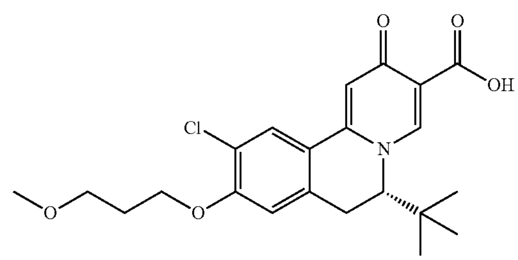 [SMILES: COCCCOc1cc2c(cc1Cl)-c1cc(=O)c(C(=O)O)cn1[C@H](C(C)(C)C)C2] | <1 nM |
| Tenofovir Disoproxil Fumarate | | 29.3 nM |

Biological Example 3: Compound Cytotoxicity Assay

Compounds are diluted with DMSO in 3-fold, 11-point scheme: top conc. of test compound is 30 mM. Add 0.25 µL titrated compounds with Echo 550 to 384-well cytotoxicity assay plates. Add 50 µl HepG2.2.15 cells to each well (4,000 cells per well). The final top conc. is 150 µM after cell addition. For solvent control well (0% effect, ZPE), 0.25 µL DMSO is added (final DMSO conc. is 0.5%). Incubate for 4 days in 37° C., 5% CO2 incubator. After 4 day incubation compound cytotoxicity is measured by Promega CellTiter-Glo reagents, briefly:
 Equilibrate the Celltiter-Glo reagent to room temperature
 Equilibrate the cytotoxicity plates to RT for 20 minutes.
 Add 50 µl of CellTiter-Glo Reagent to each well.
 Shake 2 minutes on a shaker.
 Incubate at room temperature in dark for 10 minutes.
 Read plate on Envision Plate reader (0.1 sec integration time/well)

Such assays, carried out with a range of doses of test compounds, allow the determination of the cellular $IC_{50}$ of the compounds of the present invention. The results, as shown in the Table below, show that the Example 2A has less cytotoxicity.

| Structure | IC$_{50}$ |
|---|---|
| Compound 203 in WO2015113990 | 120 uM |
| Example 2A | >150 uM |

Biological Example 4: hERG Assay (Automated Patch-Clamp)

The human ether-a-go-go related gene (hERG) encodes the inward rectifying voltage gated potassium channel in the heart ($I_{Kr}$) which is involved in cardiac repolarization. Inhibition of the hERG current causes QT interval prolongation resulting in potentially fatal ventricular tachyarrhythmia called Torsade de Pointes. A number of drugs have been withdrawn from late stage clinical trials due to these cardiotoxic effects, therefore it is important to identify inhibitors early in drug discovery.

The degree of inhibition (%) was obtained by measuring the tail current amplitude, which is induced by a one second test pulse to −40 mV after a two second pulse to +20 mV, before and after drug incubation (the difference current was normalized to control and multiplied by 100 to obtain the percent of inhibition). Concentration (log) response curves were fitted to a logistic equation (three parameters assuming complete block of the current at very high test compound concentrations) to generate estimates of the 10% inhibitory concentration (IC$_{10}$). The concentration-response relationship of each compound was constructed from the percentage reductions of current amplitude by sequential concentrations. The results, as shown in the Table below, show that the Example 2A has less cardiac toxicity.

| Structure | IC$_{10}$ |
|---|---|
| Compound 203 in WO2015113990 | 1 uM |
| Example 2A | 10 uM |

Biological Example 5: Rat PK Study

The pharmacokinetics of compounds were evaluated in female Sprague-Dawley rats via Intravenous and Oral Administration. The iv dose was administered as a slow bolus in the Jugular vein, and oral doses were administered by gavage. The formulation for IV dosing is 20% DMSO and 60% PEG 400 in water, and the PO formulation (suspension) is 1% MC, 0.4% Kolliphor EL in water. The PK time point for the IV arm is 5, 15, 30 min, 1, 2, 4, 6, 8, 12, 24 hours post dose, and for PO arm is 15, 30 min, 1, 2, 4, 6, 8, 12, 24 hours post dose. Approximately 0.2 mL blood will be collected at each time point. Blood of each sample will be transferred into plastic micro centrifuge tubes containing EDTA-K2 and collect plasma within 15 min by centrifugation at 4000 g for 5 minutes in a 4° C. centrifuge. Plasma samples will be stored in polypropylene tubes. The samples will be stored in a freezer at −75±15° C. prior to analysis. Concentrations of compounds in the plasma samples will be analyzed using a LC-MS/MS method. WinNonlin (Phoenix™, version 6.1) or other similar software will be used for pharmacokinetic calculations. The following pharmacokinetic parameters will be calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data will be described using descriptive statistics such as mean, standard deviation. Additional pharmacokinetic or statistical analysis may be performed at the discretion of the contributing scientist, and will be documented in the data summary.

The results of oral dosing of 20 mg/kg, as shown in the Table below, show that the Example 2A has better oral PK profile than Compound 203 reported in WO2015113990.

|  | Example 2A 20 mg/kg, oral dosing | Compound 203 in WO2015113990, 20 mg/kg |
|---|---|---|
| t ½ (hour) | 4.47 | 3.73 |
| $C_{max}$ (ng/mL) | 7,547 | 2,473 |
| $AUC_{last}$ (h*ng/mL) | 39,633 | 16,680 |
| oral Bioavailability | 58.6% | 40.0% |

The results of oral dosing of 10 mg/kg, as shown in the Table below, show that the Deuterium analogue Example 14 has much better oral PK profile than Example 13. The possible reason of improved PK is that the deuterium-carbon bonds are stronger than hydrogen-carbon bonds, thus the isotope would help the compounds better withstand drug-metabolizing enzymes such as the cytochrome P450s.

What is claimed is:

1. A compound or pharmaceutically acceptable salt thereof, wherein the compound is

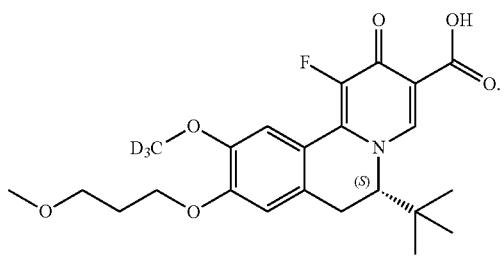

2. A pharmaceutical composition comprising a compound of claim 1, or a pharmaceutically acceptable salt thereof, and a pharmaceutically acceptable diluent or carrier.

3. A method of treatment of HBV, comprising administering to a subject in need thereof an effective amount of a compound of claim 1, or a pharmaceutically acceptable salt thereof.

* * * * *

| Example 13 10 mg/kg, oral dosing | Example 14 10 mg/kg, oral dosing |
|---|---|
| 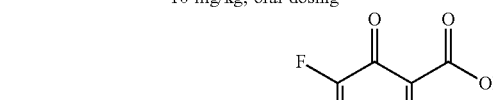 | 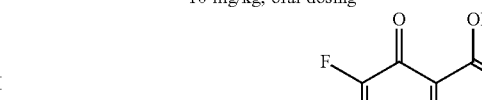 |
| $AUC_{last}$ (h*ng/mL) 5,838 | 9,053 |
| oral Bioavailability 24.1% | 61.1% |